(12) United States Patent
Beretta et al.

(10) Patent No.: US 7,745,106 B2
(45) Date of Patent: *Jun. 29, 2010

(54) METHODS AND DEVICES FOR SEPARATING LIQUID COMPONENTS

(75) Inventors: Roberto C. Beretta, Milan (IT);
Nicholas A. Grippi, Wayne, NJ (US)

(73) Assignee: Cascade Medical Enterprises, LLC, Wayne, NJ (US)

( * ) Notice: Subject to any disclaimer, the term of this patent is extended or adjusted under 35 U.S.C. 154(b) by 616 days.

This patent is subject to a terminal disclaimer.

(21) Appl. No.: 10/607,580

(22) Filed: Jun. 26, 2003

(65) Prior Publication Data

US 2004/0071786 A1 Apr. 15, 2004

Related U.S. Application Data

(63) Continuation-in-part of application No. 10/053,247, filed on Jan. 15, 2002, now Pat. No. 6,979,307, which is a continuation-in-part of application No. 09/446,729, filed as application No. PCT/IT98/00173 on Jun. 24, 1998, now Pat. No. 6,368,298.

(60) Provisional application No. 60/392,669, filed on Jun. 27, 2002.

(30) Foreign Application Priority Data

Jun. 24, 1997 (IT) ............... MI97A1490

(51) Int. Cl.
*A01N 1/02* (2006.01)
*B01L 3/00* (2006.01)
*C12M 1/00* (2006.01)
*B01D 43/00* (2006.01)

(52) U.S. Cl. ............... 435/2; 435/4; 435/283.1; 435/286.5; 210/515; 210/516; 210/519; 210/782; 210/529; 422/100; 422/101; 604/7; 604/416

(58) Field of Classification Search ............... 435/2, 435/6, 4, 283.1, 286.5; 422/72, 73, 100, 422/101; 73/1.87; 210/519, 515, 516, 782, 210/529; 604/7, 416
See application file for complete search history.

(56) References Cited

U.S. PATENT DOCUMENTS

| | | | |
|---|---|---|---|
| 1,593,814 A | 7/1926 | Vogel | |
| 2,006,451 A | 7/1935 | Glidden | |
| 3,604,410 A | 9/1971 | Whitacre | |
| 3,628,974 A | 12/1971 | Battista | |
| 3,654,925 A | 4/1972 | Holderith | |
| 3,883,574 A | 5/1975 | Axen et al. | |
| 3,939,822 A | 2/1976 | Markowitz | |
| 3,948,875 A | 4/1976 | Cohen et al. | |
| 4,050,451 A | 9/1977 | Columbus | |
| 4,091,802 A | 5/1978 | Columbus | |
| D253,190 S | 10/1979 | Bixler et al. | |
| 4,177,261 A | 12/1979 | Dietze et al. | |
| 4,251,510 A | 2/1981 | Tankersley | |
| 4,272,521 A | 6/1981 | Zuffi | |
| 4,272,523 A | 6/1981 | Kotitschke et al. | |
| 4,273,871 A | 6/1981 | Tolbert et al. | |
| 4,277,185 A | 7/1981 | Thompson | |
| 4,287,180 A | 9/1981 | Thomas | |
| 4,287,184 A | 9/1981 | Young | |
| 4,294,826 A | 10/1981 | Feldman | |
| 4,296,100 A | 10/1981 | Franco | |
| 4,298,598 A | 11/1981 | Schwarz et al. | |
| 4,322,298 A | 3/1982 | Persidsky | |
| 4,342,341 A | 8/1982 | Lee | |
| 4,350,687 A | 9/1982 | Lipton et al. | |
| 4,356,958 A | 11/1982 | Kolobow et al. | |
| 4,369,117 A | 1/1983 | White | |
| 4,378,374 A | 3/1983 | Reggio et al. | |
| 4,419,089 A | 12/1983 | Kolobow et al. | |
| 4,427,650 A | 1/1984 | Stroetmann | |
| 4,427,651 A | 1/1984 | Stroetmann | |

(Continued)

FOREIGN PATENT DOCUMENTS

EP 0105014 4/1984

(Continued)

OTHER PUBLICATIONS

Malkin, A.Y. (1994). Rheology Fundamentals. (pp. 95, 104 and 245). (ChemTec Publishing: Ontario, Canada). Online version available at: http:/www.knovel.com/knovel2/Toc.jsp?BookID=322 &VerticalID=0; downloaded on Jun. 23, 2006.*

(Continued)

*Primary Examiner*—Sandra Saucier
*Assistant Examiner*—Susan Hanley
(74) *Attorney, Agent, or Firm*—Michael Best & Friedrich LLP

(57) ABSTRACT

Methods and devices for preparing a solid-fibrin web are provided. One method may include drawing blood from a patient, separating plasma from the blood, contacting the plasma with a calcium-coagulation activator and concurrently coagulating and axially centrifuging the plasma to form the solid-fibrin web. The solid-fibrin web may be suitable for regenerating body tissue in a living organism. Devices used in the methods may also be provided.

7 Claims, 25 Drawing Sheets

U.S. PATENT DOCUMENTS

| | | |
|---|---|---|
| 4,431,582 A | 2/1984 | Stenn |
| 4,444,760 A | 4/1984 | Thomas |
| 4,465,669 A | 8/1984 | Wissler et al. |
| 4,470,968 A | 9/1984 | Mitra et al. |
| 4,470,969 A | 9/1984 | Pancham et al. |
| 4,471,053 A | 9/1984 | Comi et al. |
| 4,479,896 A | 10/1984 | Antoniades |
| 4,479,938 A | 10/1984 | Thomas |
| 4,485,096 A | 11/1984 | Bell |
| 4,503,038 A | 3/1985 | Banda et al. |
| 4,512,977 A | 4/1985 | Lundy |
| 4,514,387 A | 4/1985 | Wissler |
| 4,529,590 A | 7/1985 | LeVeen et al. |
| 4,564,359 A | 1/1986 | Ruhland |
| 4,621,052 A | 11/1986 | Sugimoto |
| 4,639,316 A | 1/1987 | Eldegheidy |
| 4,727,137 A | 2/1988 | Vallee et al. |
| 4,861,477 A | 8/1989 | Kimura |
| 4,865,733 A | 9/1989 | Tsuru et al. |
| 4,957,638 A * | 9/1990 | Smith ............ 210/782 |
| 5,030,215 A | 7/1991 | Morse et al. |
| 5,037,549 A | 8/1991 | Ballies |
| 5,065,768 A | 11/1991 | Coleman et al. |
| 5,066,286 A | 11/1991 | Ryan |
| 5,163,582 A | 11/1992 | Godolphin et al. |
| 5,165,938 A | 11/1992 | Knighton |
| 5,185,001 A | 2/1993 | Galanakis |
| 5,211,310 A | 5/1993 | Godolphin et al. |
| 5,246,666 A | 9/1993 | Vogler et al. |
| 5,257,633 A | 11/1993 | Vogler et al. |
| 5,275,731 A * | 1/1994 | Jahn ............ 210/518 |
| 5,322,515 A | 6/1994 | Karas et al. |
| 5,326,535 A | 7/1994 | Vogler et al. |
| 5,354,483 A | 10/1994 | Furse |
| 5,378,431 A | 1/1995 | Vogler et al. |
| 5,389,265 A | 2/1995 | Luoma, II |
| 5,413,246 A | 5/1995 | Godolphin et al. |
| 5,419,835 A | 5/1995 | Adams et al. |
| 5,455,009 A | 10/1995 | Volger et al. |
| 5,456,885 A | 10/1995 | Coleman et al. |
| 5,533,518 A | 7/1996 | Vogler |
| 5,555,920 A | 9/1996 | Godolphin et al. |
| 5,560,830 A | 10/1996 | Coleman et al. |
| 5,578,459 A | 11/1996 | Gordon et al. |
| 5,585,007 A | 12/1996 | Antanavich et al. |
| 5,588,946 A | 12/1996 | Graham et al. |
| 5,599,718 A | 2/1997 | Gorog |
| 5,634,474 A | 6/1997 | Grippi |
| 5,634,893 A | 6/1997 | Rishton |
| 5,643,192 A | 7/1997 | Hirsh et al. |
| 5,667,963 A * | 9/1997 | Smith et al. ............ 435/2 |
| 5,674,458 A | 10/1997 | Holm |
| 5,733,545 A | 3/1998 | Hood, III |
| 5,736,033 A | 4/1998 | Coleman et al. |
| 5,738,670 A | 4/1998 | Grippi |
| 5,739,288 A | 4/1998 | Edwardson et al. |
| 5,763,410 A | 6/1998 | Edwardson et al. |
| 5,772,643 A | 6/1998 | Howell et al. |
| 5,795,489 A * | 8/1998 | Holm ............ 210/782 |
| 5,795,571 A | 8/1998 | Cederholm-Williams et al. |
| 5,853,600 A | 12/1998 | McNeal et al. |
| 5,935,051 A | 8/1999 | Bell |
| 5,962,420 A | 10/1999 | Edwardson et al. |
| 6,010,627 A | 1/2000 | Hood, III |
| 6,063,297 A | 5/2000 | Antanavich et al. |
| 6,083,383 A | 7/2000 | Huang et al. |
| 6,114,135 A * | 9/2000 | Goldstein ............ 435/13 |
| 6,153,104 A | 11/2000 | Robertson |
| 6,225,123 B1 | 5/2001 | Cohen et al. |
| 6,234,948 B1 | 5/2001 | Yavilevich |
| 6,238,578 B1 | 5/2001 | Fiehler |
| 6,277,060 B1 | 8/2001 | Neumann |
| 6,368,298 B1 | 4/2002 | Beretta |
| 6,406,671 B1 | 6/2002 | DiCesare et al. |
| 6,544,751 B1 * | 4/2003 | Brandwein et al. ............ 435/7.1 |
| 6,569,204 B1 | 5/2003 | Aldecoa |
| 6,811,777 B2 | 11/2004 | Mishra |
| 6,979,307 B2 * | 12/2005 | Beretta et al. ............ 604/6.01 |
| 2006/0074394 A1 | 4/2006 | Beretta et al. |
| 2008/0190857 A1 | 8/2008 | Beretta et al. |
| 2008/0199513 A1 | 8/2008 | Beretta et al. |

FOREIGN PATENT DOCUMENTS

| | | |
|---|---|---|
| EP | 0128849 | 12/1984 |
| EP | 0190018 | 8/1986 |
| EP | 0 580 094 A1 | 1/1994 |
| EP | 0 592 242 A1 | 4/1994 |
| EP | 0 580 094 B1 | 10/1996 |
| EP | 0 740 155 A1 | 10/1996 |
| EP | 0 512 612 B1 | 2/1998 |
| FR | 2533438 | 3/1984 |
| GB | 2146335 | 4/1985 |
| IT | 01 292 410 | 2/1999 |
| JP | 61200903 | 9/1986 |
| JP | 2504915 | 5/1994 |
| JP | 10277143 | 10/1998 |
| JP | 2000178201 | 6/2000 |
| WO | 8605683 | 10/1986 |
| WO | 8701728 | 3/1987 |
| WO | 91/09573 | 7/1991 |
| WO | WO 94/22503 | 10/1994 |
| WO | 95/05849 | 3/1995 |
| WO | WO 95/12371 | 5/1995 |
| WO | WO 96/17871 | 6/1996 |
| WO | WO 96/27397 | 9/1996 |
| WO | WO 98/11925 | 3/1998 |
| WO | WO 98/58689 | 12/1998 |
| WO | 00/07659 | 2/2000 |
| WO | 01/60424 | 8/2001 |
| WO | 02/34110 | 5/2002 |
| WO | 02/45767 | 6/2002 |

OTHER PUBLICATIONS

Franklin JD, Lynch JB, "Effects of topical application of epidermal growth factor on wound healing", *Plastics and Reconstructive Surgery*, Dec. 1979, pp. 766-770.

Buckley A, Davidson JM, "Sustained release of epidermal growth factor accelerates wound repair", *Proceeding National Academy Science USA*, vol. 82, pp. 7340-7344, Nov. 1985.

Sporn MB, Roberts AB, "Polypeptide transforming growth factors isolated from bovine sources and used for wound healing in vivo", *Science*, vol. 219, pp. 1329-1331, Mar. 18, 1983.

Canalis E, "Effect of Platelet-derived growth factor on DNA and protein synthesis in cultured rat calvaria", *Metabolism*, vol. 30, No. 10, pp. 970-975, Oct. 1981.

Niewiarowski S, Markiewicz, "Inhibition of the platelet-dependent fibrin retraction by the fibrin stabilizing factor (FSF, factor XIII)", M, *Journal of Laboratory and Clinical Medicine*, vol. 81, No. 6, pp. 641-650, May 1973.

Li AKC, Koroly MJ, "Mechanical and humoral factors in wound healing", *British Journal of Surgery*, vol. 68, pp. 738-743, 1981.

Niewiarowski S, Millman M, "Potentiation of the thrombin induced platelet release reaction by fibrin", *Thrombosis Research*, vol. 9, No. 2, pp. 181-190, 1976.

Carroll RC, Gerrard JM, "Clot retraction facilitates clot lysis", *Blood*, vol. 57, No. 1, pp. 44-48, Jan. 1981.

Joist JH, Niewiarowski S, "Retention of platelet fibrin stabilziing factor during the platelet release reaction and clot retraction", *Thrombos. Diathes. Haemorrh.*, vol. 29, pp. 679-683, 1973.

Niall M, Ryan GB, "The effect of epidermal growth factor on wound healing in mice", *Journal of Surgical Research*, vol. 33, No. 2, pp. 164-169, Aug. 1982.

Cazenave JP, Packham MA, "Inhibition of platelet adherence to a collagen-coated surface by agents that inhibit platelet shape change and clot retraction", *Journal of Laboratory and Clinical Medicine*, vol. 84, No. 4, pp. 483-493, Oct. 1974.

Niewiarowski S, Stewart GJ, "Effect of ADP and thrombin on fibrin retraction induced by human platelets and fibroblasts", *Thromb Diathes Haemorrh*, vol. 34, pp. 316-317, Oct. 1974.

Niewiarowski S, Goldstein S, "Fibrin clot retraction by human skin fibroblasts: effects of ADP and thrombin", *Proceedings of the Society for Experimental Biology and Medicine*, vol. 151, pp. 253-256, 1976.

Cohen I, Gabbay J, "Fibrin-blood platelet interaction in a contracting clot", *Thromb Diath Haemorrh*, vol. 34, No. 2, pp. 559, Nov. 15, 1975.

Dhall TZ, Shah GA, "Fibrin network structure: modification by platelets", *Thrombosis and Haemostasis*, vol. 49, No. 1, pp. 42-46, 1983.

Niewiarowski S, Gegoeczi E, "Platelet interaction with fibrinogen and fibrin: comparison of the interaction of platelets with that of fibroblasts, leukocytes and erythrocytes", *Ananls of the New York Academy of Sciences*, vol. 201, pp. 72-83, 1972.

Knighton DR, Hunt TK, "Role of platelets and fibrin in the healing sequence: an in vivo study of angiogenesis and collagen synthesis", *Annals of Surgery*, vol. 196, No. 4, pp. 379-388, Oct. 1982.

Doni MG, Fantin G, "Thrombin-induced calcium and magnesium platelet release and clot retraction", *Haematologica*, vol. 60, No. 3, pp. 286-299, Sep. 1975.

Jelenska M, Kopec M, "Blood platelets cause retraction of collagen gel", *Thrombosis and Haemostasis*, vol. 44, No. 3, pp. 161-164, 1980.

Lundblad RL, "A rapid method for the purification of bovine thrombin and the inhibition of the purified enzyme with phenylmethylsulfonyl fluoride", *Biochemistry*, vol. 10, No. 13, pp. 2501-2506, Jun. 22, 1971.

Chao FC, Tullis JL, "Concentration effects of platelets, fibrinogen and thrombin on platelet aggregation and fibrin clotting", *Thromb Diathes Haemorrh*, vol. 32, No. 1, Sep. 30, 1974.

Solum, "Platelet aggregation during fibrin polymerization", *Scandinavian Journal of Clinical & laboratory Investigation*, vol. 18, No. 6, pp. 577-587, 1966.

Tashjian, "Platelet-derived growth factor stimulates bone resorption via a prostaglandin-mediated mechanism", *Endocrinology*, vol. 111, No. 1, pp. 118-124, 1982.

Mustard JF, Perry DW, "Factors responsible for ADP-induced release reaction of human platelets", *American Journal of Physiology*, vol. 228, No. 6, Jun. 1975.

Day HJ, Ang G, "Platelet release reaction during clotting of native human platelet-rich plasma", *Proceedings of the Society of Experimental and Biological Medicine*, vol. 139, No. 3, pp. 717-721, Mar. 1972.

Niewiarowski S, Stewart GJ, "ADP, thrombin and Bothrops atrox thrombin like enzyme in platelet-dependent fibrin retraction", *American Journal of Physiology*, vol. 229, No. 3, pp. 737-745, Sep. 1975.

Mustard JF, Perry DW, "Preparation of suspensions of washed platelets from humans", *British Journal of Haematology*, vol. 22, No. 2, pp. 193-204, Feb. 1972.

Packham MA, Guccione MA, "Platelet aggregation and release: effects of low concentrations of thrombin or collagen", *American Journal of Physiology*, vol. 225, No. 1, pp. 38-47, Jul. 1973.

Niewiarowski S, Thomas DP, "Platelet aggregation by ADP and thrombin", *Nature*, vol. 212, pp. 1544-1547, Dec. 31, 1966.

Thorton JW, Hess CA, "Epidermal growth factor In the healing of second degree burns: a controlled animal study", *Burns*, vol. 8, No. 3, pp. 156-160, 1983.

Holmsen H, Day HJ, "The blood platelet release reaction", *Scandinavian Journal of Haematology (Supplement K)*, pp. 3-21, 1969.

Rosenthal AR, Harbury C, "Use of a platelet-fibrinogen-thrombin mixture as a corneal adhesive: experiments in sutureless lamellar keratoplasty in the rabbit", *Investigative Ophthalmology*, vol. 14, No. 11, pp. 872-875, Nov. 1975.

Schulte W, "Centrifuged autologous blood for filling large bone defects: a modification to the autologous blood method", *Zentrifugiertes Eigenblut (Centrifuged Autologous Blood) DZZ 24*, vol. 10, pp. 854-857, 1969.

Schulte W, "Autologous Blood Filing: A new method in the treatment of major bone defects following oral surgery", *Eigenblutfullung Grosserer Knochendefekte DZZ 15*, vol. 12, pp. 910-914, 1960.

Rosenthal AR, Egbert PR, "Use of Platelet-Fibrinogen-Thrombin mixture to seal experimental penetrating corneal wounds", *Graefes Archiv Ophthalmologie*, vol. 207, pp. 111-115, 1978.

Silverberg GD, Harbury CB, "A physiological sealant for cerebrospinal fluid leaks", *Journal of Neurosurgery*, vol. 46, pp. 215-219, Feb. 1977.

Pearl RM, Wustrack KO, "Microvascular Anastomosis using a blood product sealant-adhesive", *Surgery, Gynecology & Obstetrics*, vol. 144, pp. 227-231, Feb. 1977.

Bernstein, Lori R., et al., "Migration of Cultured Vascular Cells in Response to Plasma and Platelet-Derived Factors", Department of Physiology and Surgery, Harvard Medical School, Children's Hospital Medical Center, J. Cell Sci. 56, 1982, pp. 71-82.

Zetter, Bruce R., et al., "Stimulation of Human Vascular Endothelia Cell Growth by a Platelet Derived Growth Factor and Thrombin", Journal of Supramolecular Structure 11, 1979, pp. 361-370.

Knighton, David R., et al., "Platelet-Derived Angiogenesis: Initiator of Healing Sequence", Department of Surgery, School of Medicine, University of California, San Francisco, 1986, pp. 226-228.

Seppä, Heikki, et al., "Platelet-derived Growth Factor is Chemotactic for Fibroblasts", The Journal of Cell Biology, vol. 92, Feb. 1982 pp. 584-588.

Senior, Robert, M., "Chemotactic Activity of Platelet Alpha Granule Proteins for Fibroblasts", The Journal of Cell Biology, vol. 96, Feb. 1983, pp. 382-385.

Gospodarowicz, Denis, "Humoral Control of Cell Proliferation: The Role of Fibroblast Growth Factor in Regeneration, Angiogenesis, Wound Healing, and Neoplastic Growth", Department of Molecular Endocrinology, Salk Institute for Biological Studies, San Diego, California, 1976, pp. 1-19.

Office Action from U.S. Appl. No. 10/053,247, dated Nov. 3, 2004 (9 pages).

Office Action from U.S. Appl. No. 12/032,346, dated Oct. 14, 2008 (8 pages).

Office Action from U.S. Appl. No. 11/284,584, dated Jun. 1, 2007 (9 pages).

Office Action from U.S. Appl. No. 11/284,584, dated Sep. 12, 2006 (7 pages).

03796273.5 European Office Action, 4 pages, dated Jun. 23, 2008.

03796273.5 European Office Action, 3 pages, dated Nov. 30, 2006.

06027028.7 European Office Action, 6 pages, dated Dec. 23, 2008.

03703826.2 European Office Action, 6 pages, dated Dec. 12, 2005.

PCT/US03/01226 International Search Report, 6 pages, dated Sep. 11, 2003.

PCT/US03/20163 Written Opinion, 4 pages, dated Jun. 22, 2004.

Japanese Patent Application No. 2003-559565 Office Action, 14 pages, Nov. 21, 2008.

Japanese Patent Application No. 2004-557099 Office Action, 13 pages, dated May 1, 2009.

Office Action from Japanese Patent Office for Application No. 2003-559565 dated Jun. 15, 2009 (12 pages).

Arch Otorhinolaryngol, vol. 237, 1983, G. Wolf, "Der konzentrierte autologe Gewebekleber", p. 276-p. 283; p. 280; paragraphs 3-6; p. 281, paragraphs 1-3.

Wolf, Der Knozentrierte autologe Gewebekleber, Spring 1983, Arch Otorhinolaryngol, 237: pp. 279-283.

\* cited by examiner

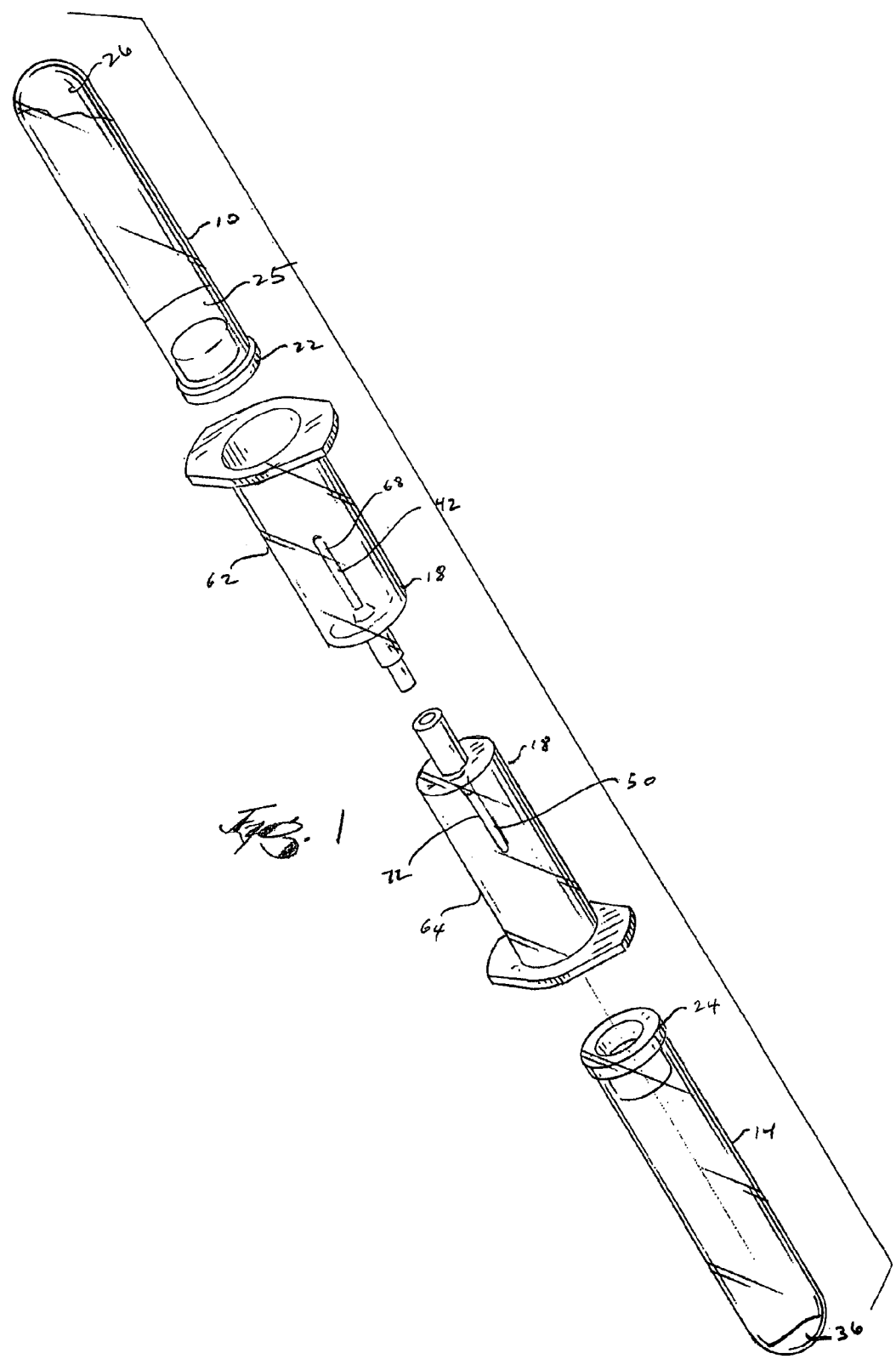

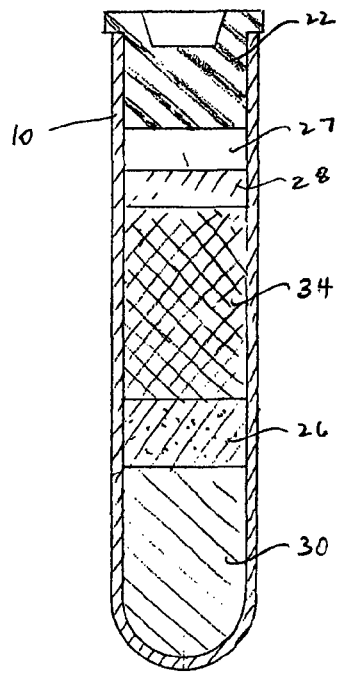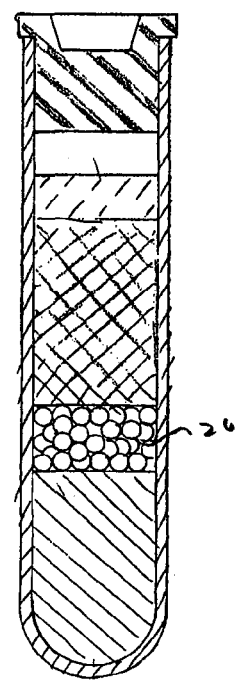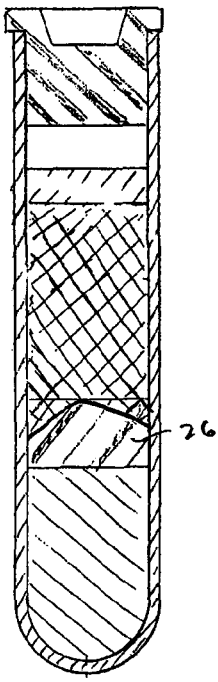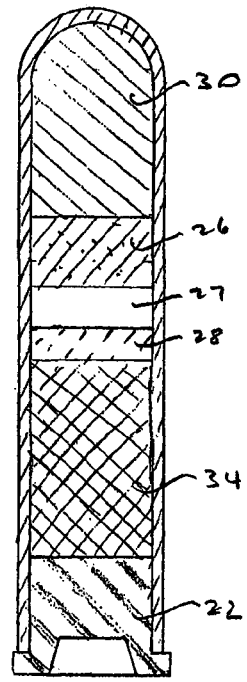

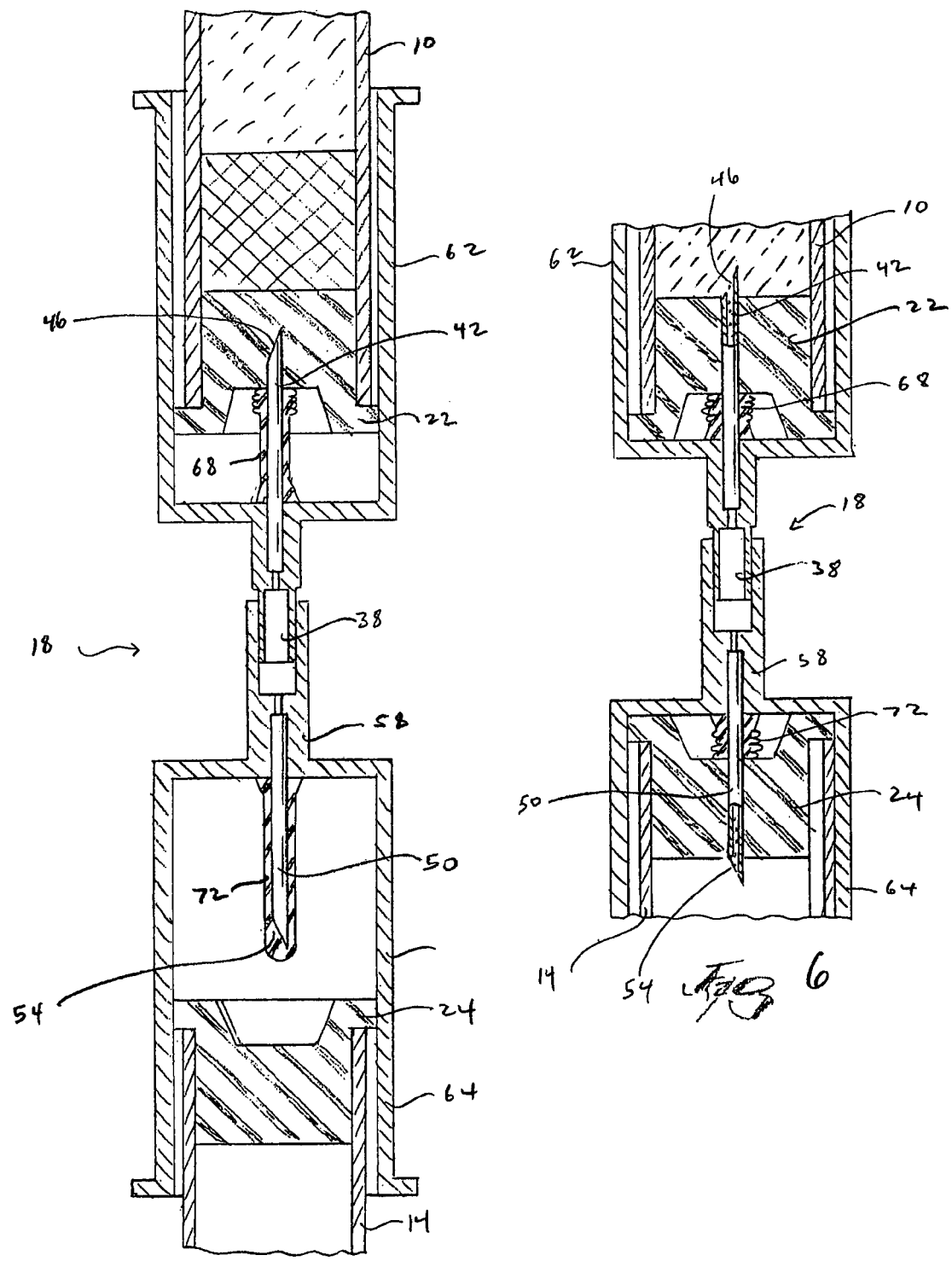

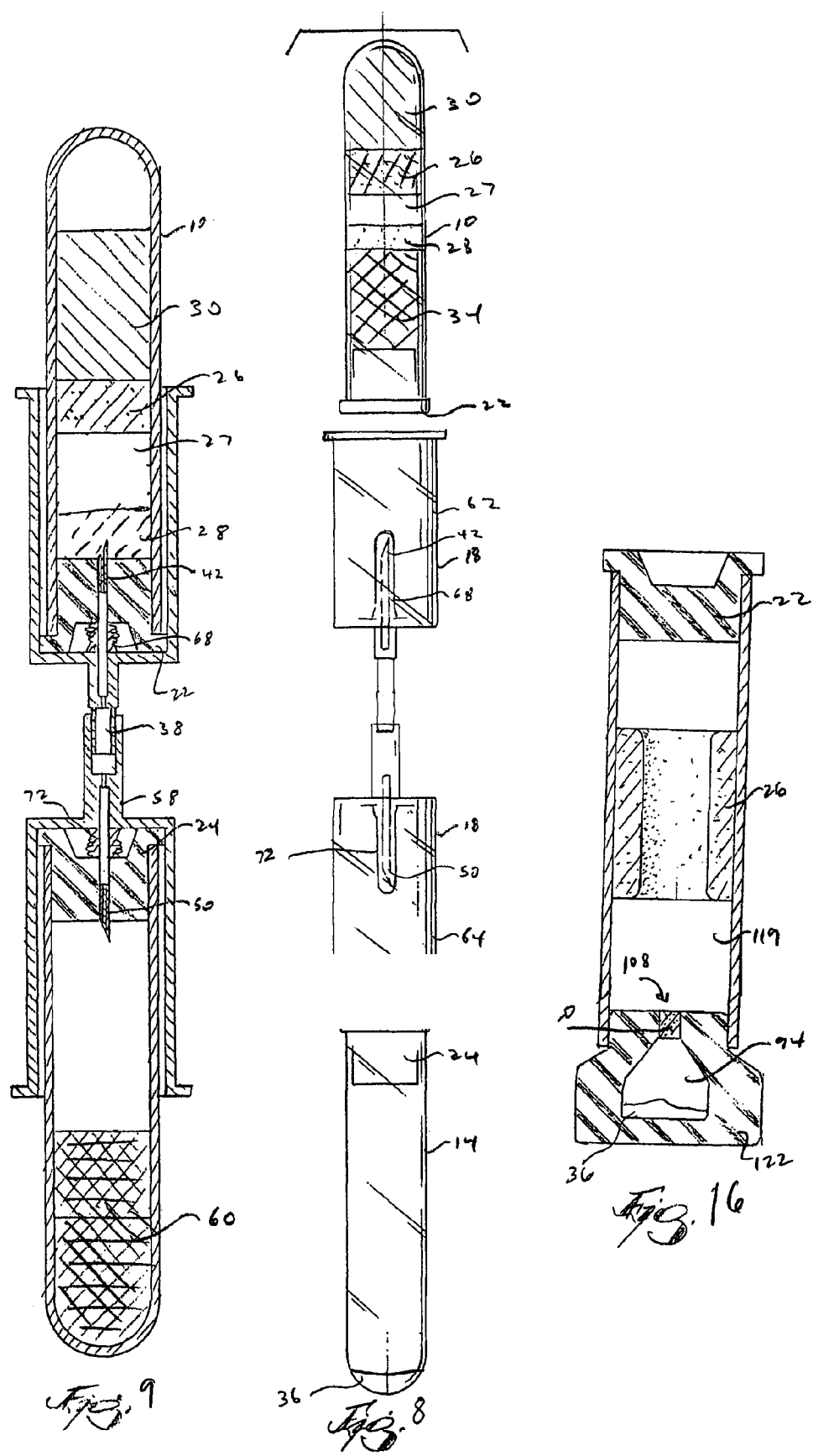

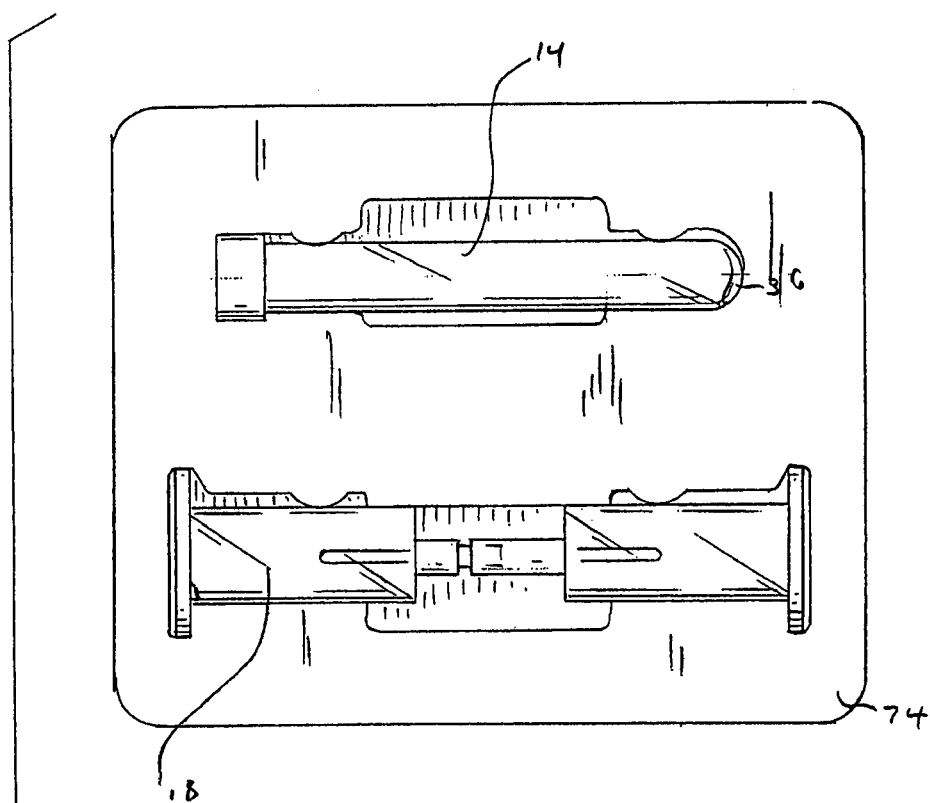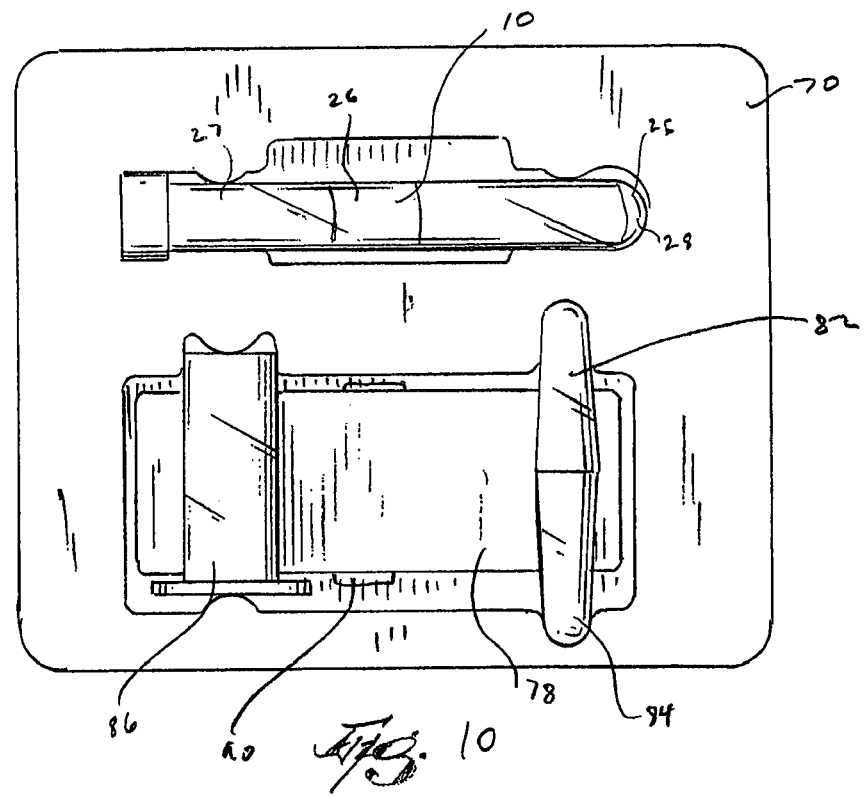
Fig. 10

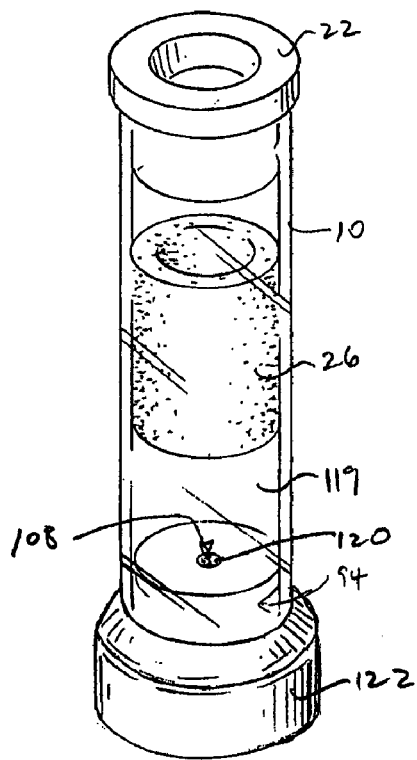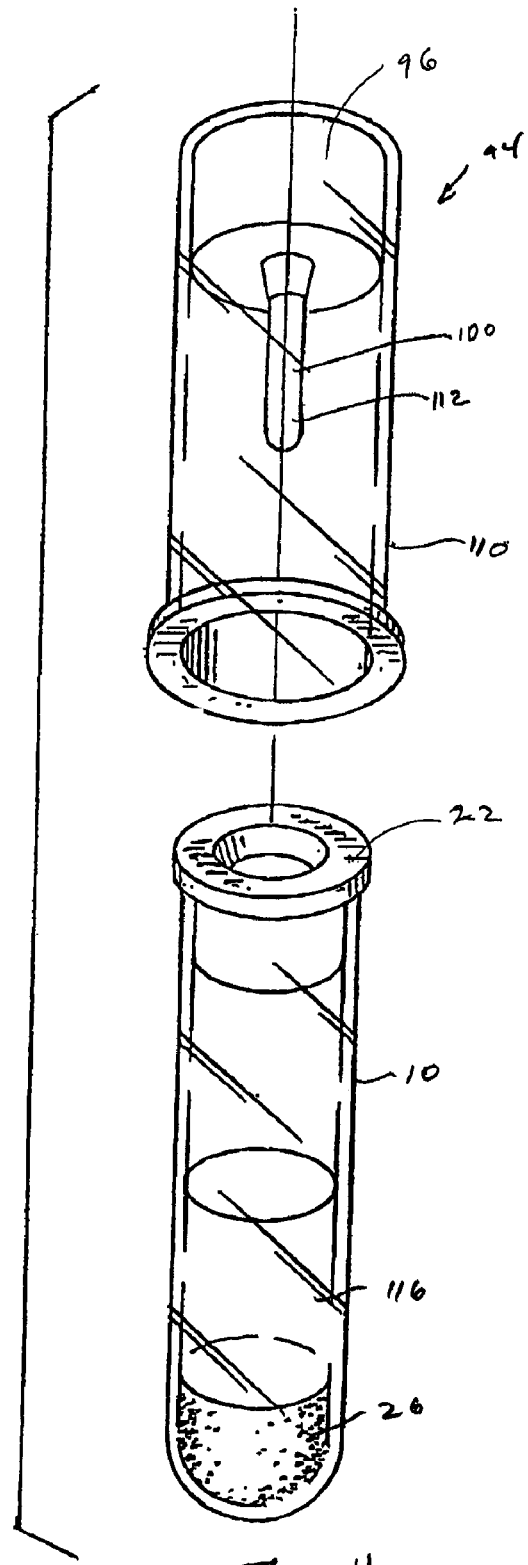

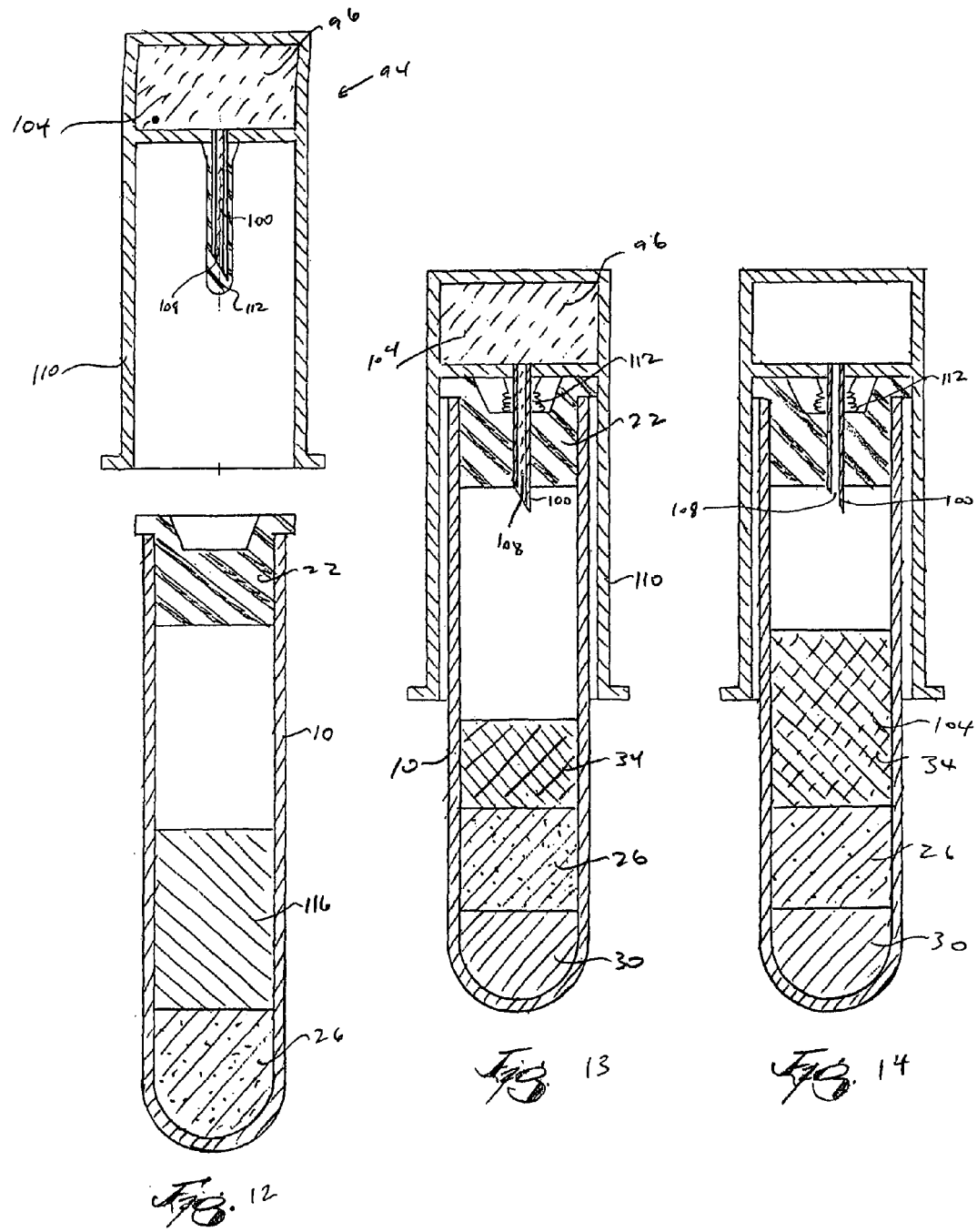

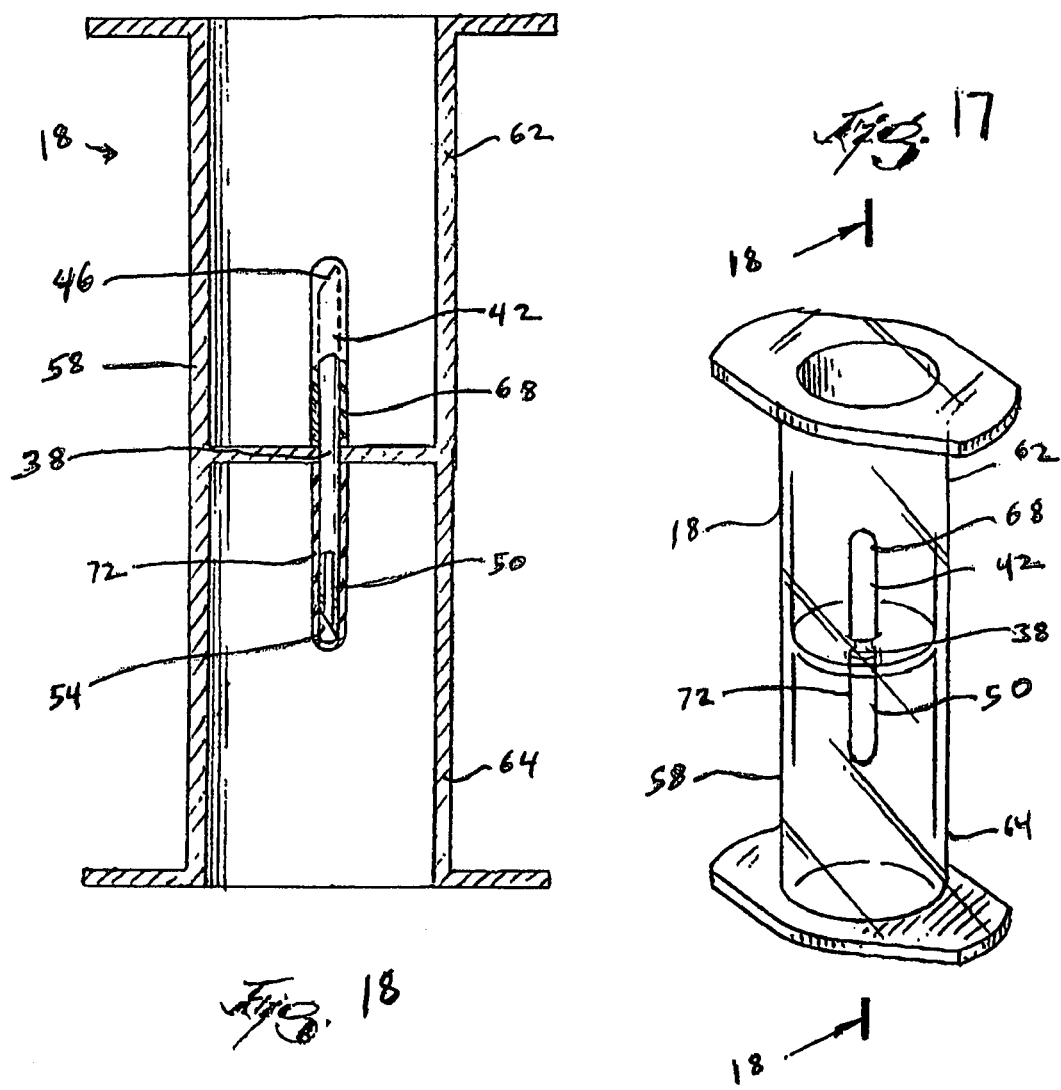

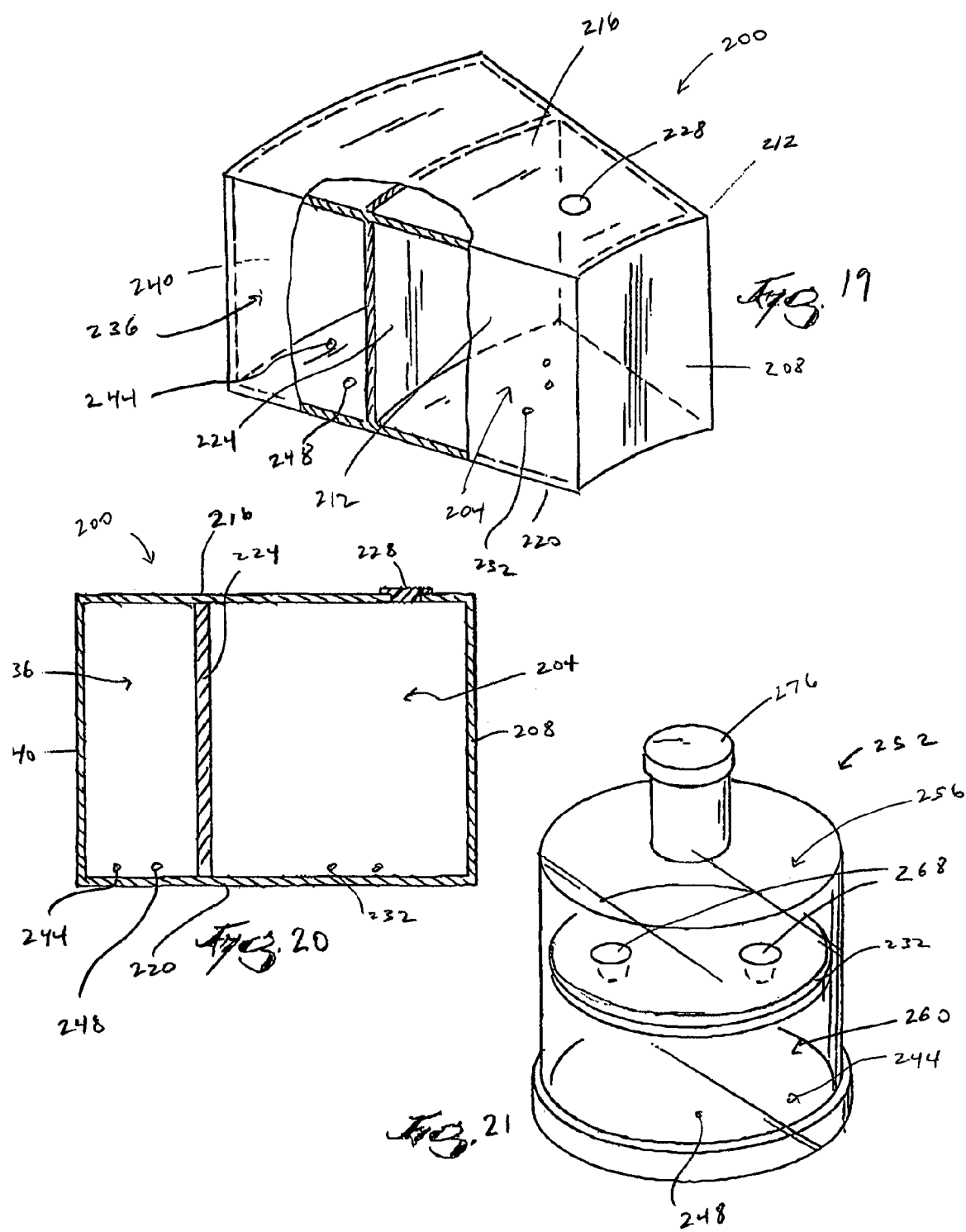

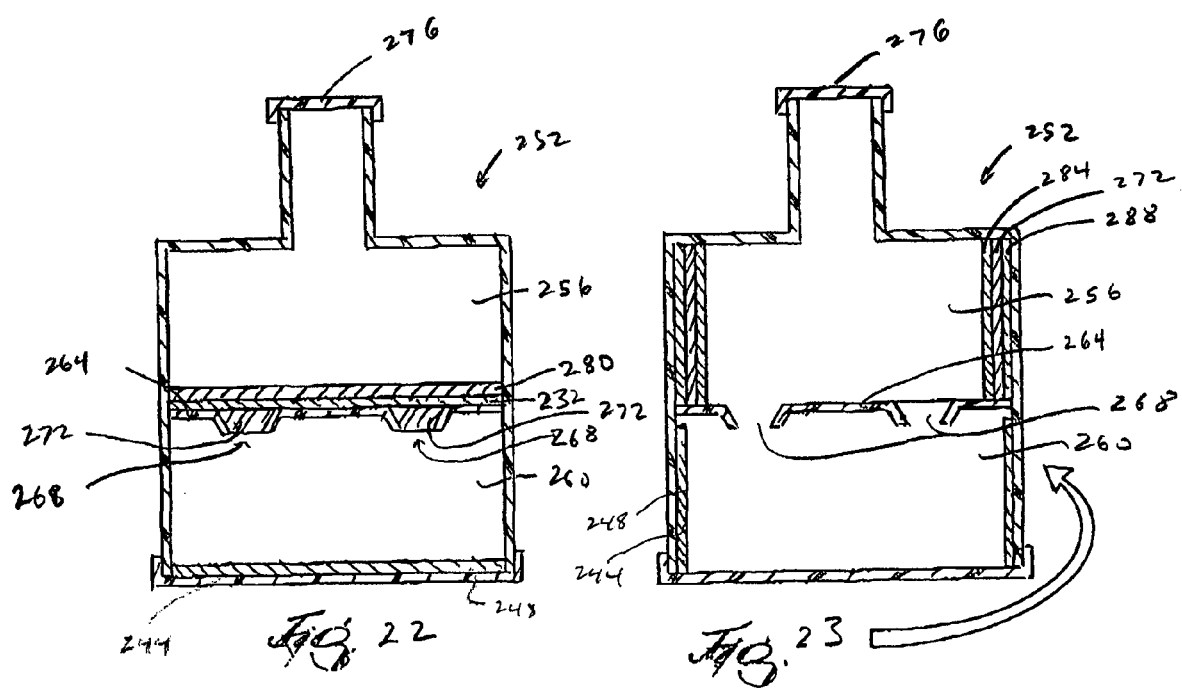
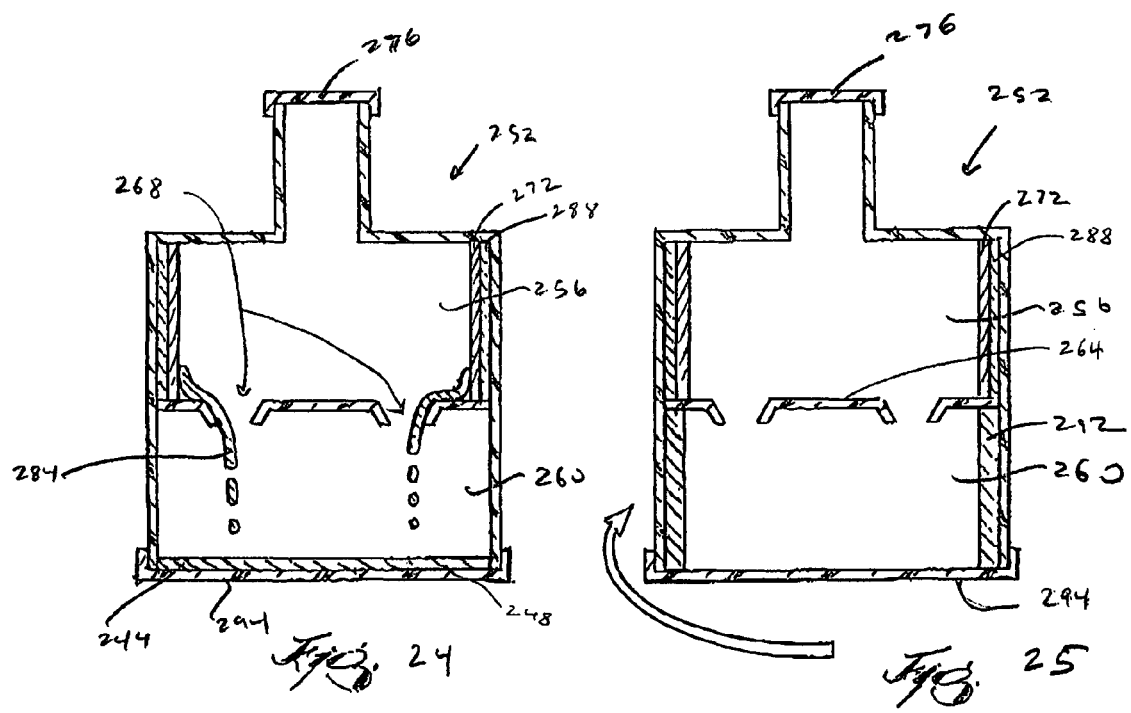

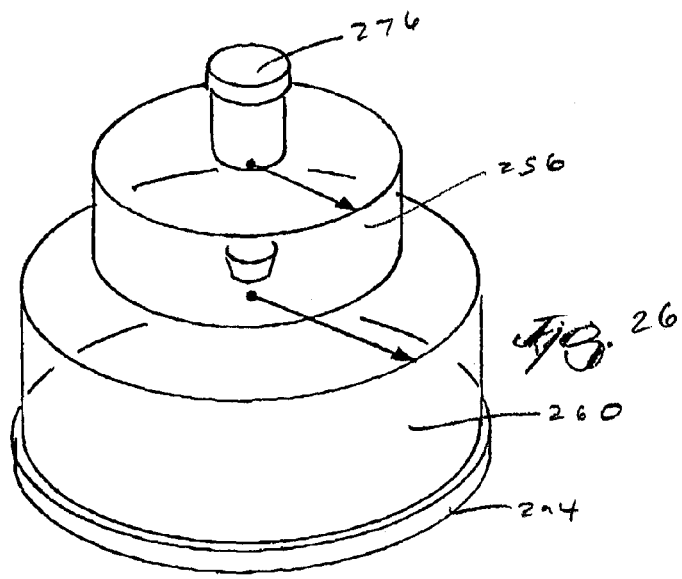
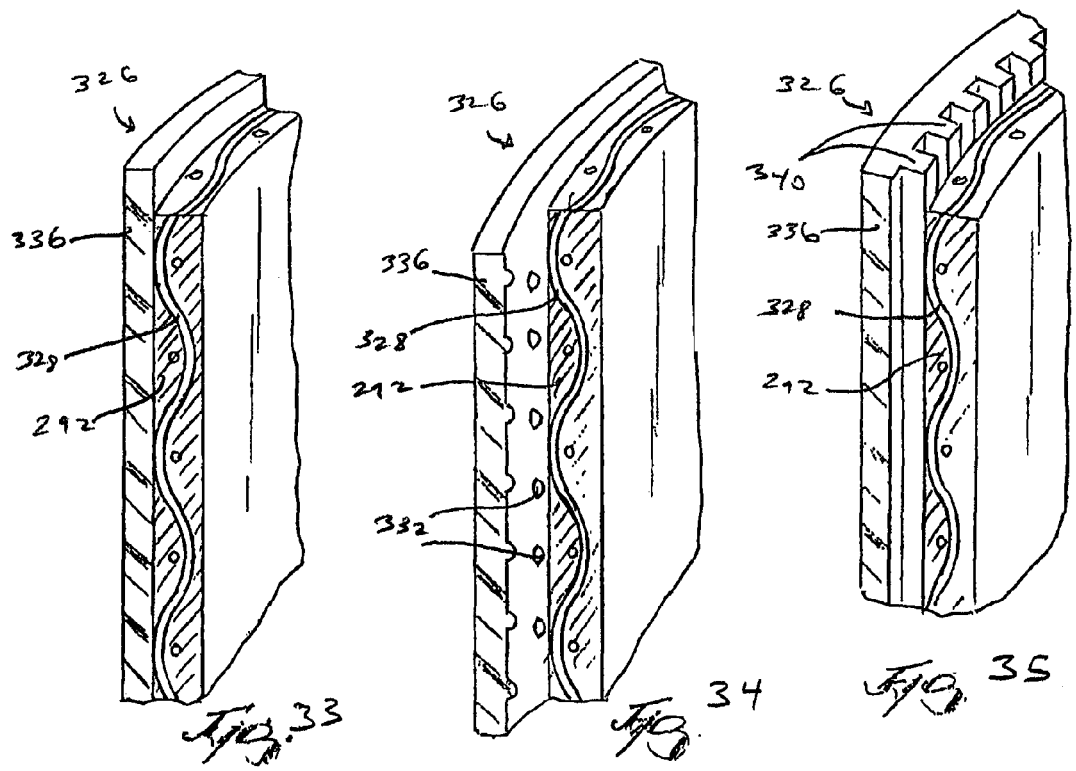

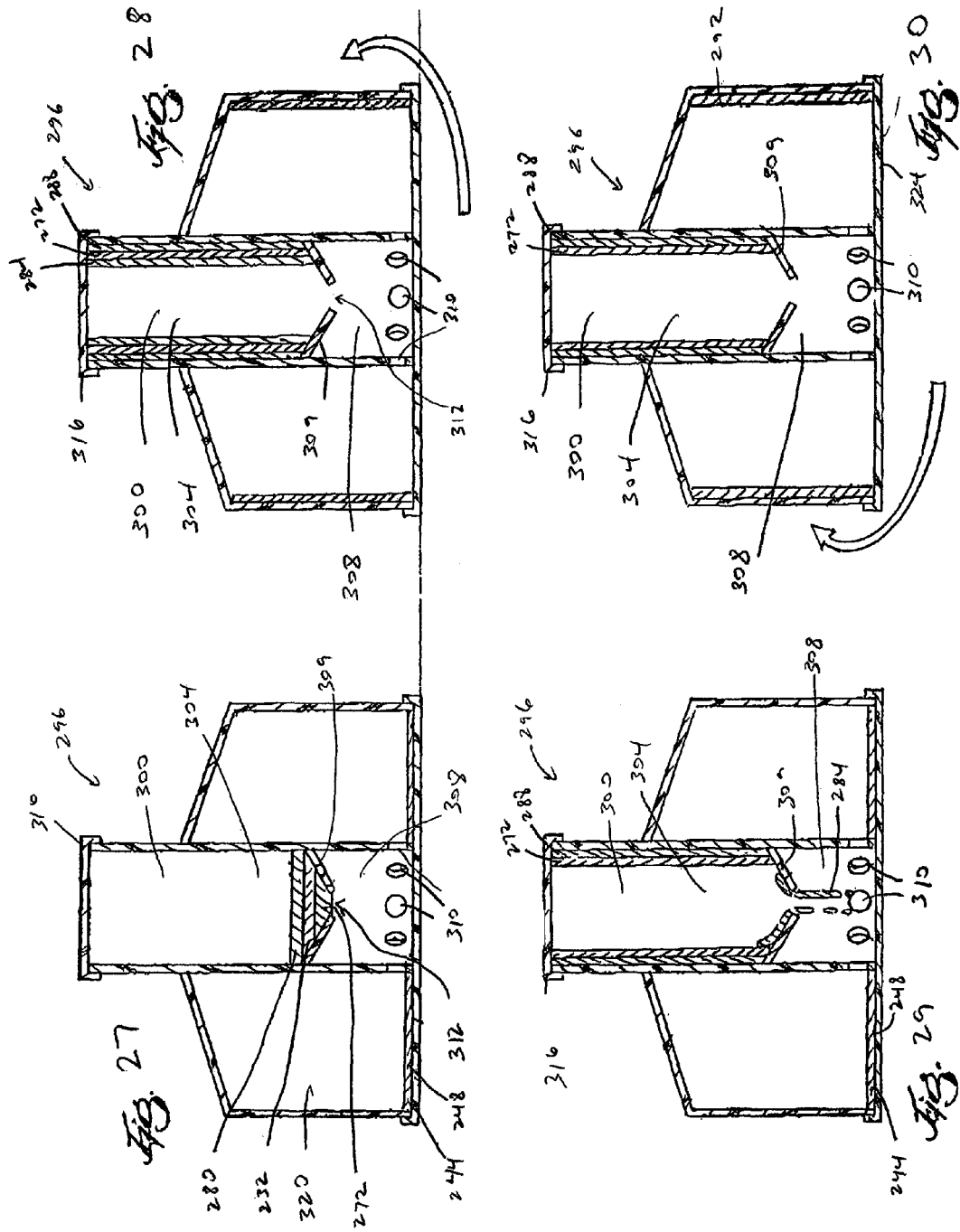

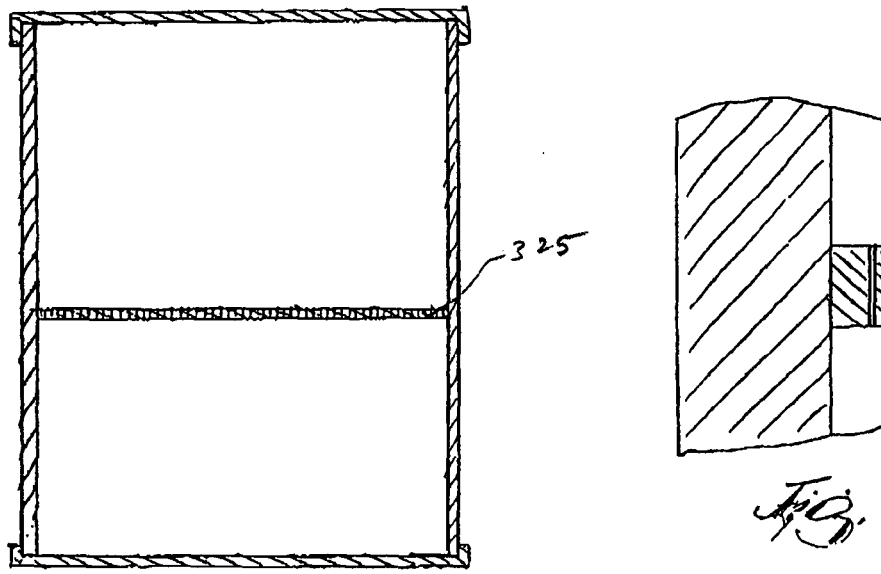
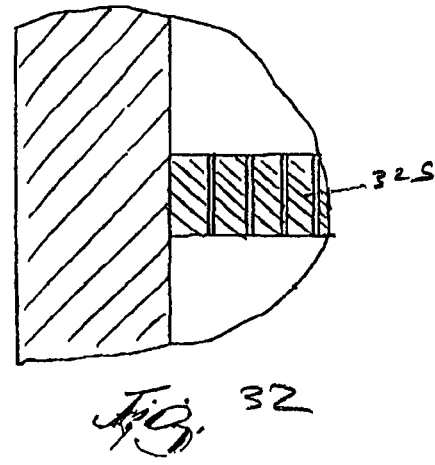
Fig. 31
Fig. 32
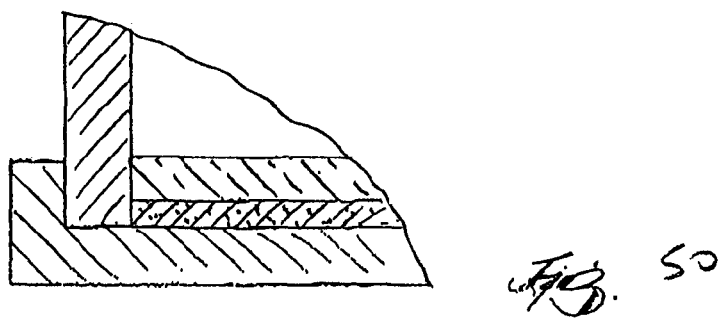
Fig. 50
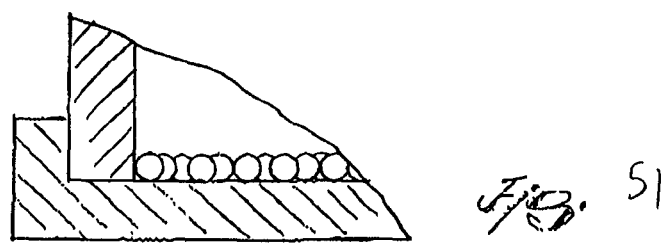
Fig. 51

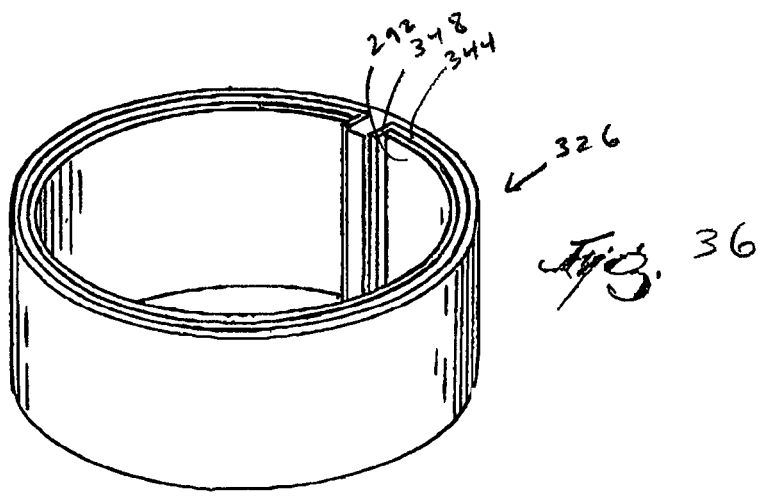
Fig. 36
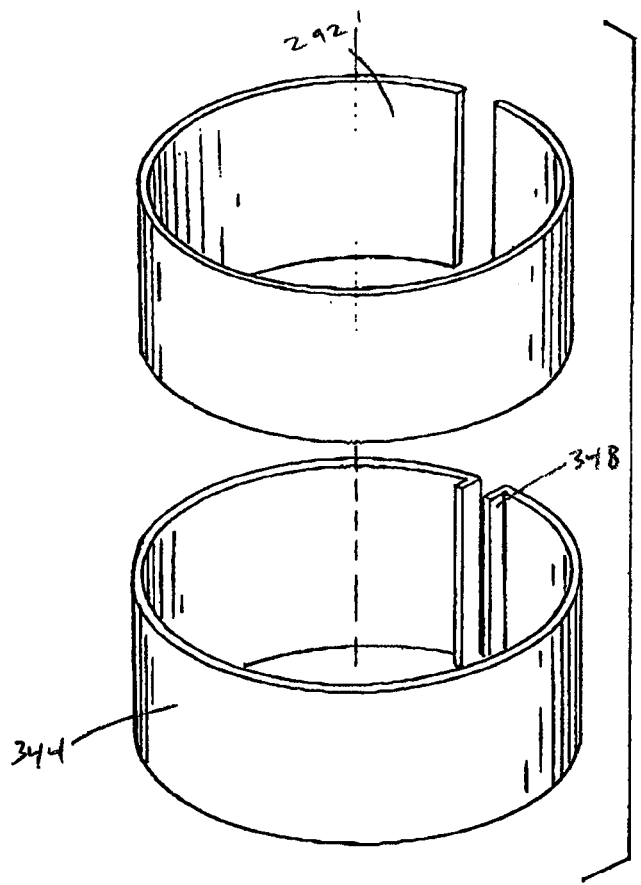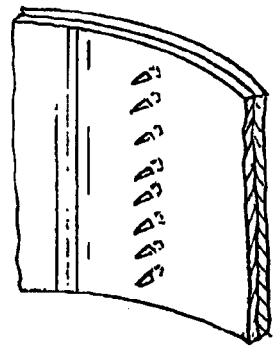
Fig. 37

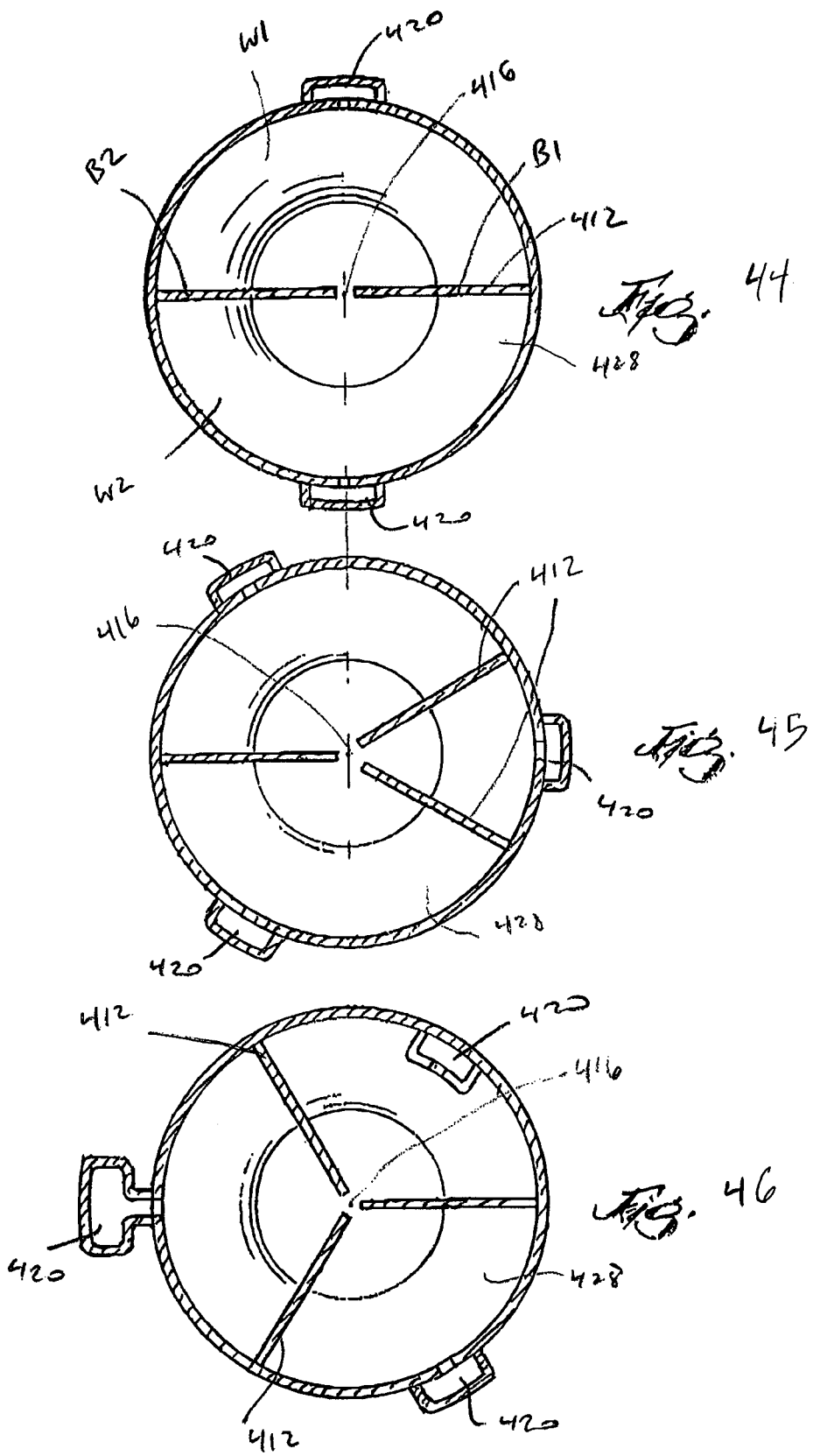

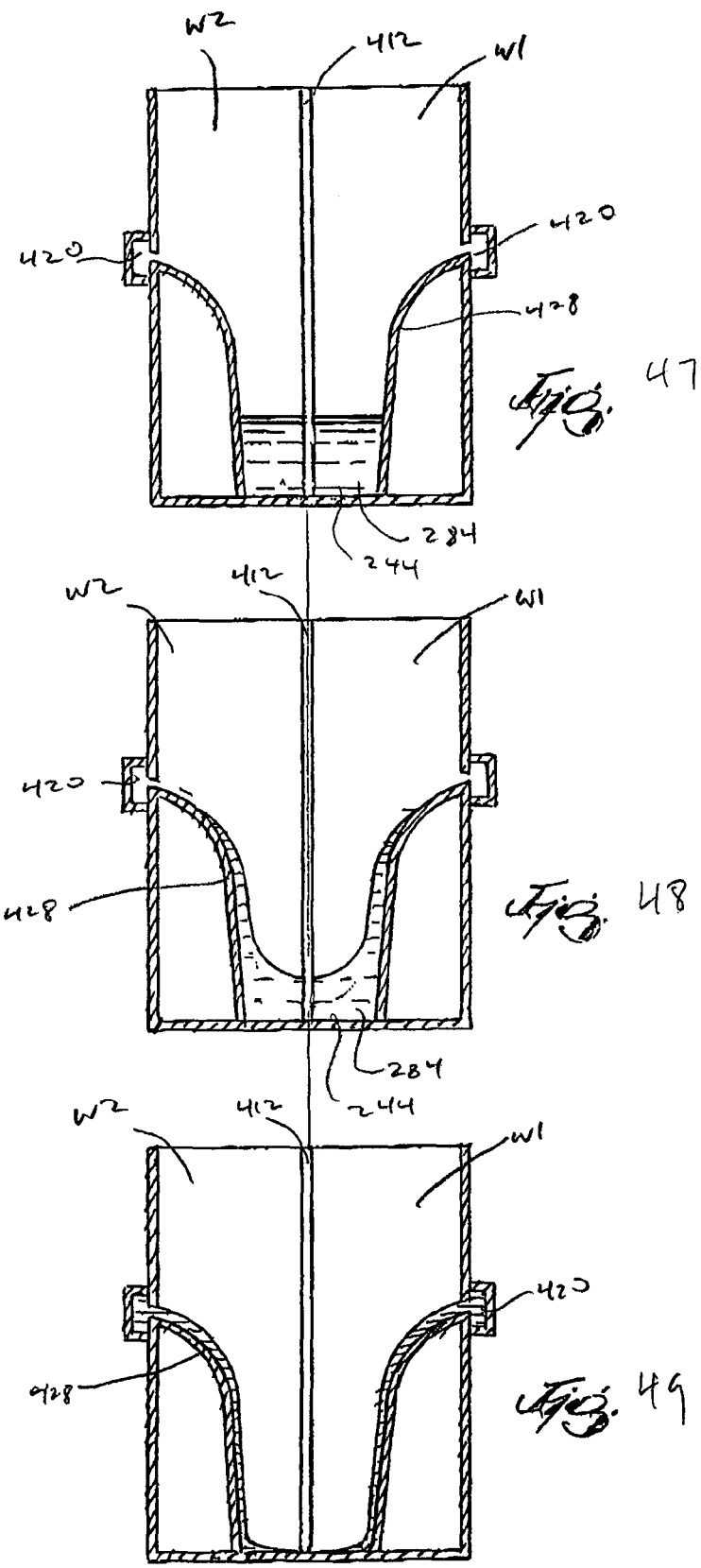

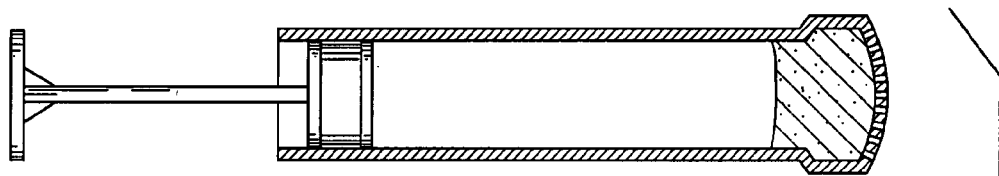
*Fig. 54e*
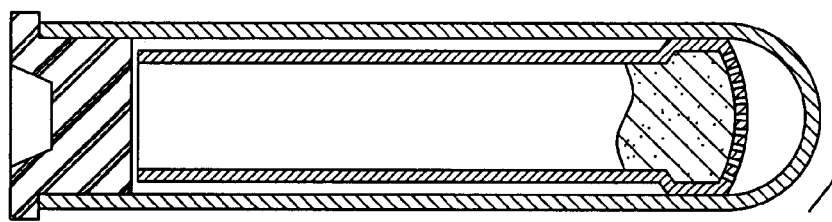
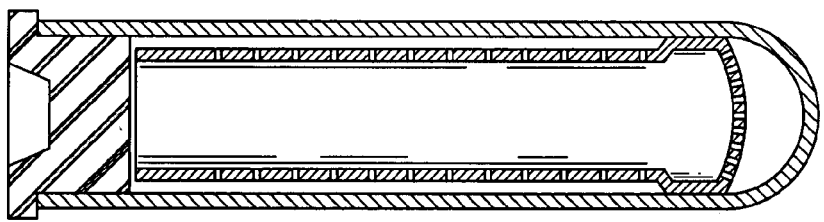
*Fig. 54d*

METHODS AND DEVICES FOR SEPARATING LIQUID COMPONENTS

CROSS-REFERENCE TO RELATED APPLICATIONS

This application claims priority under 35 U.S.C. §119(e) to U.S. provisional patent application No. 60/392,669 filed on Jun. 27, 2002 and is a continuation-in-part of and claims priority to U.S. application Ser. No. 10/053,247, filed on Jan. 15, 2002, which issued as U.S. Pat. No. 6,979,307 on Dec. 27, 2005, which is a continuation-in-part of and claims priority to U.S. application Ser. No. 09/446,729 filed on Jul. 13, 2001, which issued as U.S. Pat. No. 6,368,298 on Apr. 9, 2002, which is a 35 U.S.C. §371 application of and claims priority to international application no. PCT/IT98/00173 filed Jun. 24, 1998, which claims priority to Italian application no. MI97A001490 filed Jun. 24, 1997. This application claims priority to each of the applications mentioned above.

BACKGROUND OF THE INVENTION

The present invention relates to systems, kits and methods for preparing a solid-fibrin web or autologous fibrin glue.

Fibrin glue is known to be a haemoderivative largely that is used as a topical surgical adhesive or an haemostatic agent. Several kits are available on the market that contain concentrated fibrinogen from donors, associated to a proteic activator of human or animal origin, such as thrombin or batroxobin, for obtaining heterologous fibrin glue.

Such known kits involve the use of material of human or animal origin, which, owing to its origin, could result in possible viral contamination and in serious risks for the receiver of the fibrin glue. In the past the authorities have been compelled to suspend from trade or even ban the haemoderivatives obtained by using material of human or animal origin. Furthermore, rejection cases are known from the literature resulting from reimplanting fibrin produced by using human or animal proteins in patients. Such cases are indeed due to the heterologous origin, with respect to the receiver organism, of the sealant protein being reimplanted or some of the components used for preparing it.

The autologous fibrin glue, i.e. fibrin glue autologously obtained from a patient's own blood, is more reliable with respect to the rejection and/or infection risks. Several procedures have already been described for obtaining extemporary autologous fibrin glue, but no "ready to use" kit is available on the market although some relevant references can be found in the patent literature.

U.S. Pat. No. 5,733,545 discloses a plasma-buffy coat concentrate to be combined with a fibrinogen activator to form a platelet glue wound sealant. The method disclosed in this patent allows for a patient's blood to be processed in order to obtain autologous fibrin glue, but the methods use thrombin or batroxobin as the fibrinogen activator. These activators are of human or animal nature and therefore still involve the risk of rejection and/or viral infections for the patient.

U.S. Pat. No. 5,555,007 discloses a method and an apparatus for making concentrated plasma to be used as a tissue sealant. The method consists in separating plasma from whole blood and removing water from said plasma by contacting it with a concentrator to provide concentrated plasma which can be thereafter coagulated with a solution containing thrombin and calcium. The apparatus comprises a first centrifuge separator in a first chamber, a concentrator (e.g. dextranomer or polyacrylamide) included in a second chamber communicating with the first chamber, and a second separator. The method disclosed in this reference requires a long time for obtaining the plasma concentrate necessary for the subsequent preparation of autologous fibrin glue and the apparatus is expensive and not disposable. The method does not disclose using a calcium-coagulation activator, and requires a pre-concentration step.

Many methods and systems require the transfer of a fluid from one container to another. For example, many chemical and medical devices require the transfer of a requisite volume of liquid to be reacted sequentially with various reagents and specific volumetric aliquots. A common practice is to remove closures on two containers and to pipette liquid in one container to the other. This practice, however, exposes the sample to environmental contaminants. For example, this technique is used to transfer plasma that has been separated from red blood cells in a blood sample. A special technique is required, however, to remove the plasma at the interface meniscus. Frequently the high-density, undesirable, lower-fraction red blood cells contaminate the aspirated sample. To avoid this problem, the pipette is frequently maintained a safe distance from the meniscus (i.e. the separator between the plasma and red blood cells), thereby resulting in an incomplete transfer of the sample. The incomplete transfer of the desirable fraction results in lower than optimum volume yield and non-stoichiometric ratios of the sample reagents and those in the second container. This second condition can be a serious source of performance variation of the product. This is the case in many enzyme reactions in which reaction rates are a maximum at certain stoichiometric ratios and rapidly diminish at higher or lower ratios.

Wound care is one of the most important issues in medicine, especially with respect to chronic ulcers, fistulae, etc. This issue is important not only because of the high cost of management, but also because of the low success rate. Other problems associated with wound care and burn care include loss of liquids and the possibility of infections occurring. Synthetic or animal-origin membranes have been used to separate bone cavities from soft tissues in the process of re-ossification.

One treatment for wound care may include applying biological tissues or sponges (generally protein based) of animal origin, e.g., collagen, fibrin, albumin to a wound site. However, allergic and immunological responses are common with these applications. Fifty percent of these cases are not resolved with a single application. More than twenty percent may not be resolved even after two applications.

Another treatment includes skin transplantation, which is performed for the most difficult cases. Skin transplantation is expensive, however, and may cost around $600-700 per application. A mesh of modified horse's collagen is used to support the new autologous tissue. The application is a difficult process that may take up to 20 days for cultivation of derma tissue, with the possibility to contaminate the sample, related to the dimensions.

Overall, methods and systems for preparing autologous fibrin glue or a solid-fibrin which is capable of regenerating tissue in a living organism are desired.

DETAILED DESCRIPTION OF THE DRAWINGS

FIG. 1 is a perspective view of a first embodiment of the invention.

FIG. 2 is a cross-sectional view of a primary container of the first embodiment shown in FIG. 1.

FIG. 3 is a cross-sectional view of a different embodiment of the primary container of FIG. 2.

FIG. 4 is a cross-sectional view of a different embodiment of the primary container of FIG. 2.

FIG. 5 is an enlarged partial cross-sectional view of a portion of the first embodiment in FIG. 1 depicting a first end of a transfer device beginning to puncture a sealed primary container.

FIG. 6 is a view similar to that set forth in FIG. 5 depicting the first end of the transfer device fully puncturing the sealed primary container and a second end of the transfer device fully puncturing a sealed secondary primary container.

FIG. 7 is a view similar to FIG. 2 showing the primary tube and its contents inverted.

FIG. 8 is a top plan view of the first embodiment shown in FIG. 1.

FIG. 9 is a partial cross-sectional view of FIG. 8 showing the primary container, secondary container and transfer device engaged, and the contents of the first container being transferred to the second container.

FIG. 10 is a top plan view of a kit embodying the invention.

FIG. 11 is a perspective view of a second embodiment of the invention.

FIG. 12 is a cross-sectional view of the second embodiment of the invention shown in FIG. 11.

FIG. 13 a cross-sectional view similar to FIG. 12 showing the reservoir and the primary collection device piercing the primary collection device.

FIG. 14 a cross-sectional view similar to FIG. 12 showing the reservoir piercing the primary collection device, and emptying its contents into the device.

FIG. 15 is a perspective view of a third embodiment of the invention.

FIG. 16 is a cross-sectional view of a third embodiment of the invention shown in FIG. 15.

FIG. 17 is a perspective view of a transfer device embodying the invention.

FIG. 18 is a cross-sectional view taken along line 18-18 in FIG. 17.

FIG. 19 is a perspective view of cartridge embodying one aspect of the invention.

FIG. 20 is a cross-sectional side view of the cartridge in FIG. 19.

FIG. 21 is a perspective view of a device which may be employed in an axial-centrifugation system embodying another aspect of the invention.

FIG. 22 is a cross-sectional view of the device and contents shown in FIG. 21.

FIG. 23 is a cross-sectional view of the device and contents shown in FIG. 21 during an initial centrifugation.

FIG. 24 is a cross-sectional view of the device and contents shown in FIG. 21 after the initial centrifugation has stopped.

FIG. 25 is a cross-sectional view of the device and contents shown in FIG. 21 during a secondary centrifugation.

FIG. 26 is a perspective view of a variation of the device shown in FIG. 21, wherein the radius of the secondary densification chamber is greater than the radius of the primary cell-separation chamber.

FIG. 27 is a cross-sectional view of a variation of the system shown in FIG. 21, in which concentric chambers are employed.

FIG. 28 is a cross-sectional view of the device and contents shown in FIG. 27 during an initial centrifugation.

FIG. 29 is a cross-sectional view of the device and contents shown in FIG. 27 after the initial centrifugation has stopped.

FIG. 30 is a cross-sectional view of the device and contents shown in FIG. 27 during a secondary centrifugation.

FIG. 31 is a cross-sectional view of a system employing a hydrophobic membrane.

FIG. 32 is an enlarged portion of FIG. 31.

FIG. 33 is a cross-sectional view of a portion of a wall of the densification chamber having a fabric reinforcement.

FIG. 34 is a cross-sectional view of a variation of the wall of FIG. 33, in which the wall is provided with bumps.

FIG. 35 is a cross-sectional view of a variation of the wall of FIG. 33, in which the wall is provided with grooves.

FIG. 36 shows a densification chamber lined with a removable film having tabs, the film facilitating membrane removal.

FIG. 37 shows a membrane having perforations to facilitate tearing.

Figure 38:
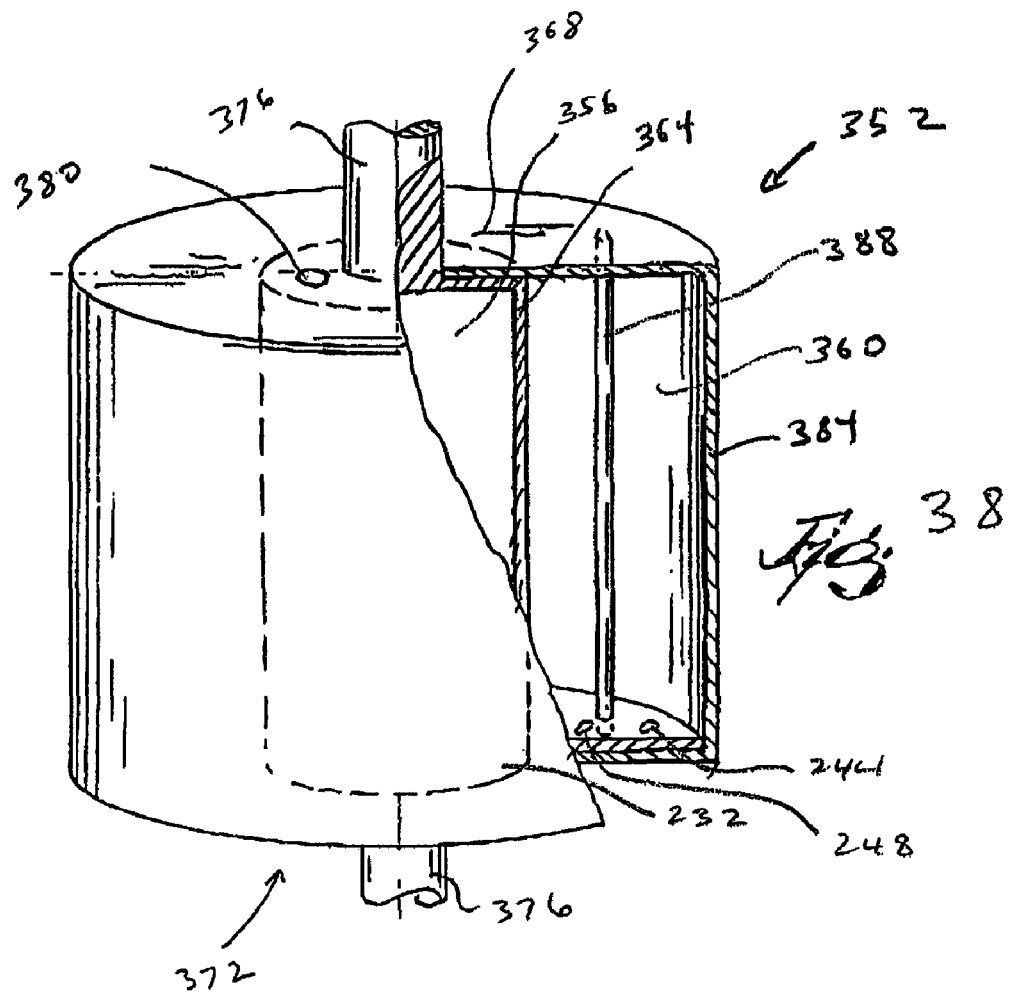

FIG. 38 is a perspective view partially in section of a rotor medical device embodying another aspect of the invention.

Figure 39:
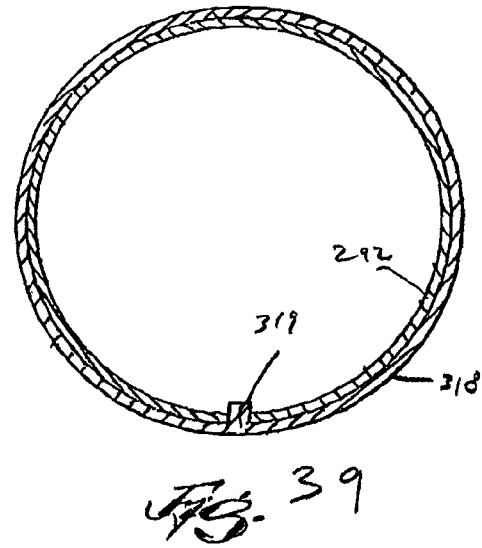

FIG. 39 is a bottom plan view of a densification chamber having one or more solid ribs on the interior wall.

FIG. 40 shows examples of a mold oriented for use in a radial centrifugation system (as shown in FIG. 40($a$)) and a mold oriented for use in an axial centrifugation system (as shown in FIG. 40($b$)).

Figure 41:
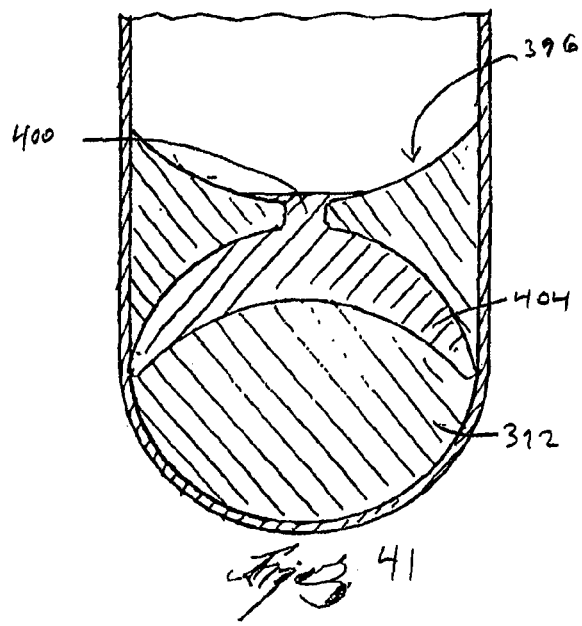

FIG. 41 shows a portion of a device having a mold, in which a funnel and a runner are employed to promote cavity filling.

Figure 42:
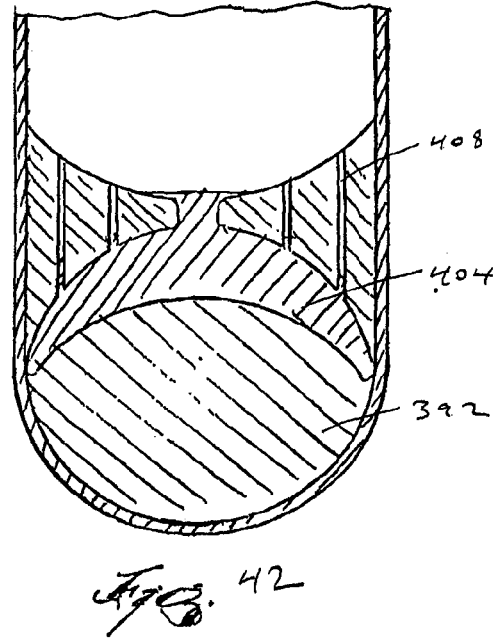

FIG. 42 shows a portion of a device having a mold, in which vent holes are employed to allow for proper escape of gases and liquids.

Figure 43:
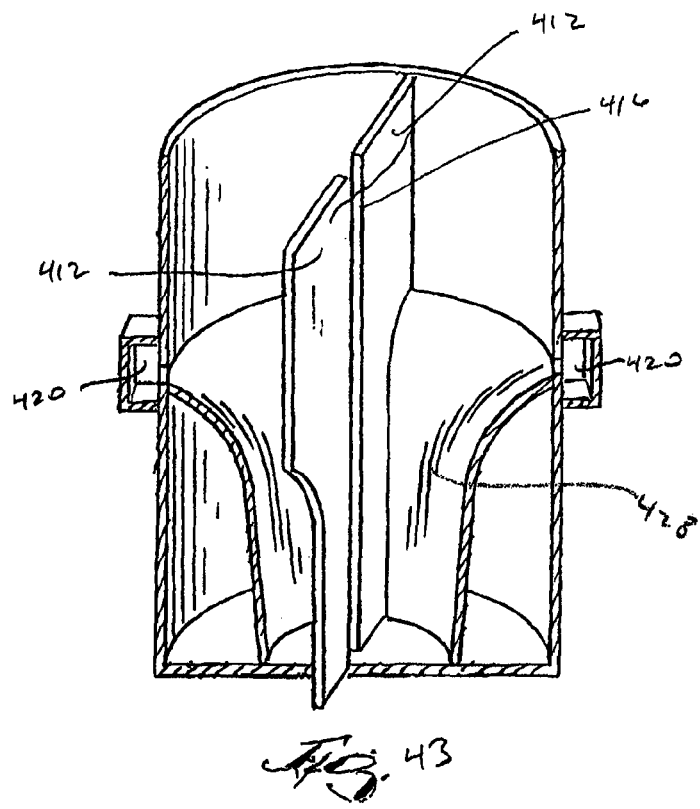

FIG. 43 is a perspective view, shown partially in cross-section, of a device having molds, vanes dividing two chambers and a vent.

FIG. 44 is a top plan view of the device of FIG. 43.

FIG. 45 is a top plan view of a device having molds, vanes dividing three unequal chambers and a vent.

FIG. 46 is a top plan view of a modification of the device of FIG. 45, in which the molds are shown being integral, connected and extending from the device and vanes divide three equal chambers.

FIG. 47 is a cross-sectional side view of a portion of any of the devices shown in FIGS. 43-46 after platelet-rich plasma has been introduced into at least one chamber, but before the device has been centrifuged.

FIG. 48 is a cross-sectional side view of a portion of the device shown in FIG. 47 just after the device has been centrifuged.

FIG. 49 is a cross-sectional side view of a portion of the device shown in FIG. 47 at full centrifugation, in which the platelet-rich plasma has entered at least one of the molds.

FIG. 50 is a cross-sectional view showing a plastic alternative, e.g., glass affixed to the bottom.

FIG. 51 is a cross-sectional view showing a plastic alternative, e.g., glass spheres glued or hot staked to the bottom.

Figures 52A, 52B:
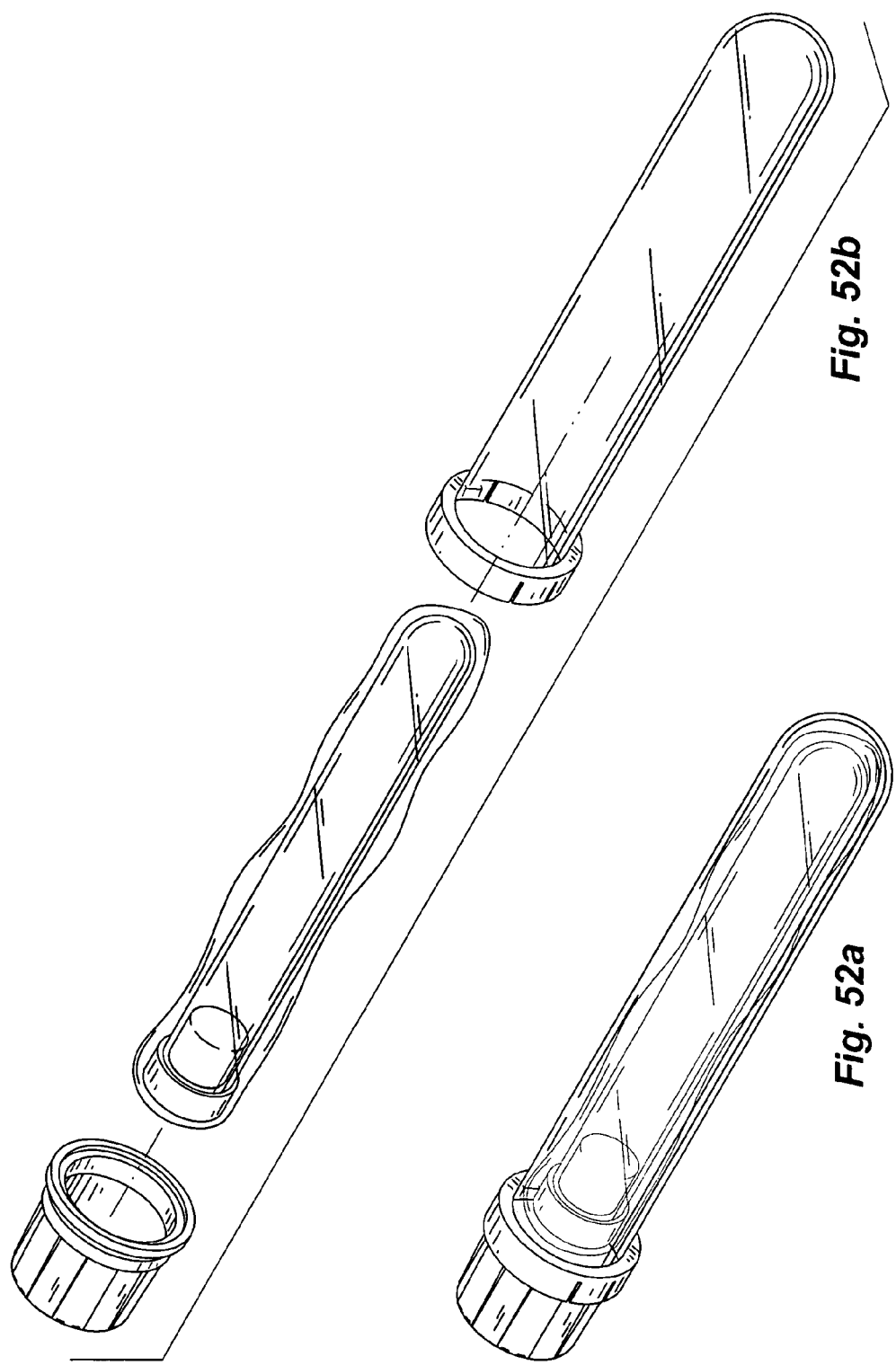

FIG. 52$a$ is a perspective view of a primary container wrapped in a sterile film and housed by a carrier.

FIG. 52$b$ is an exploded view of FIG. 54$a$ showing a collar on the primary tube.

Figure 53:
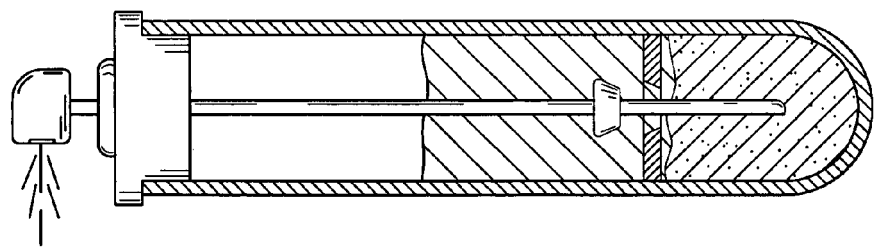

FIG. 53 is a partial cross-sectional view of a dispensing/pumping system that can be employed with certain embodiments of the invention.

FIG. 54$a$ is a cross-sectional view of a cup having a perforated bottom, the cup being housed by a secondary container.

FIG. 54$b$ is a cross-sectional view of an alternative embodiment of the cup shown in FIG. 54$a$.

FIG. 54$c$ is a cross sectional view taken along line 54$c$-54$c$ in FIG. 54$b$.

FIG. 54$d$ is a cross-sectional view of an alternative embodiment of the cup shown in FIG. 54$b$, the cup having perforations along the length thereof.

FIG. 54$e$ is a partial cross-sectional view showing a dispensing system operated by positive displacement in conjunction with the cup of any of FIGS. 54$a$-54$d$.

Figure 54C:
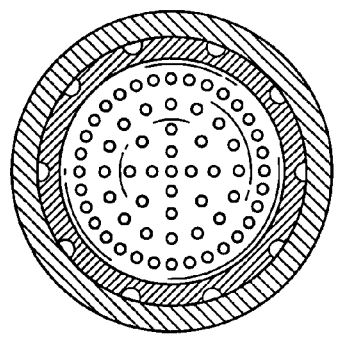
Figure 54B:
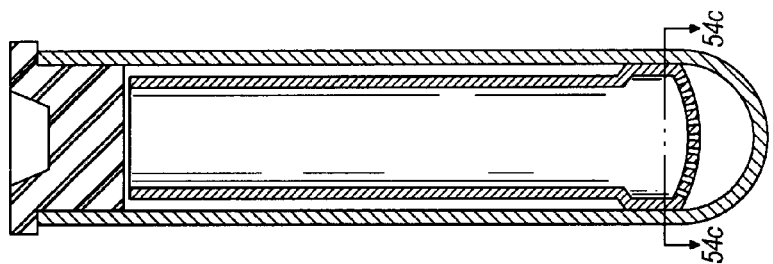
Figure 54A:
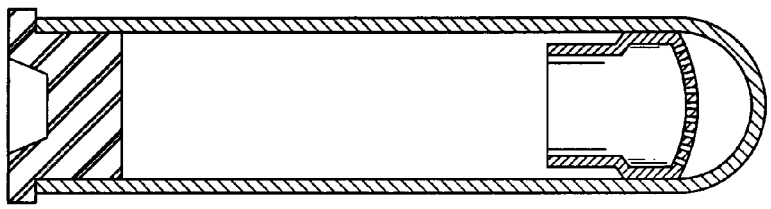
Figure 54F:
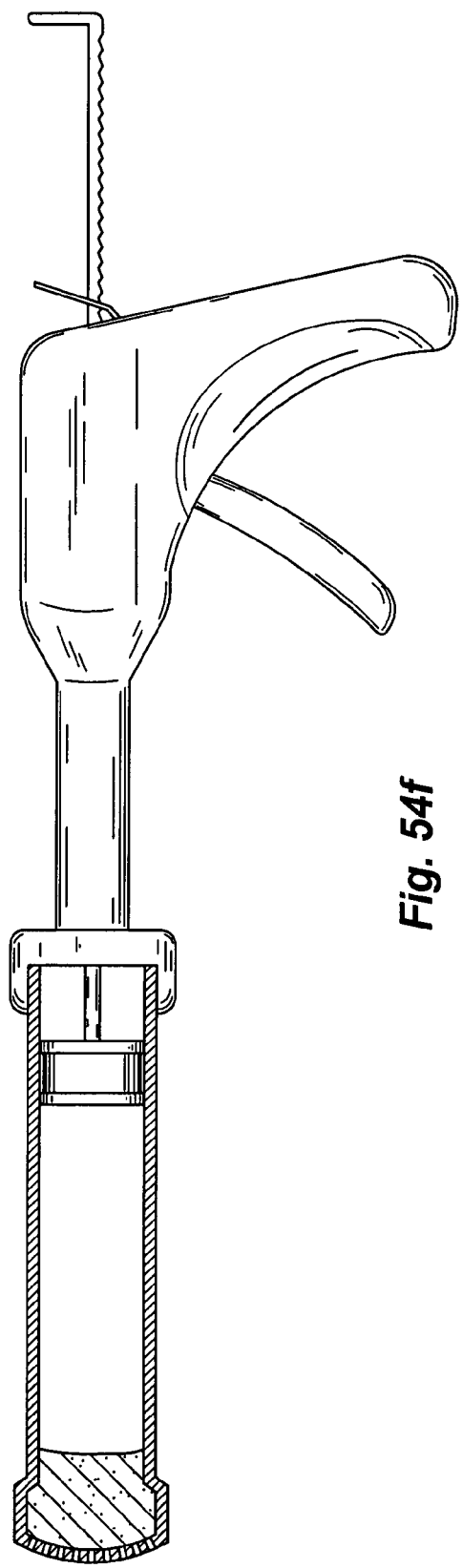

FIG. 54*f* is a partial cross-sectional view showing a dispensing system similar to FIG. 54*e*, in which a caulking gun mechanism is utilized.

Figure 55:
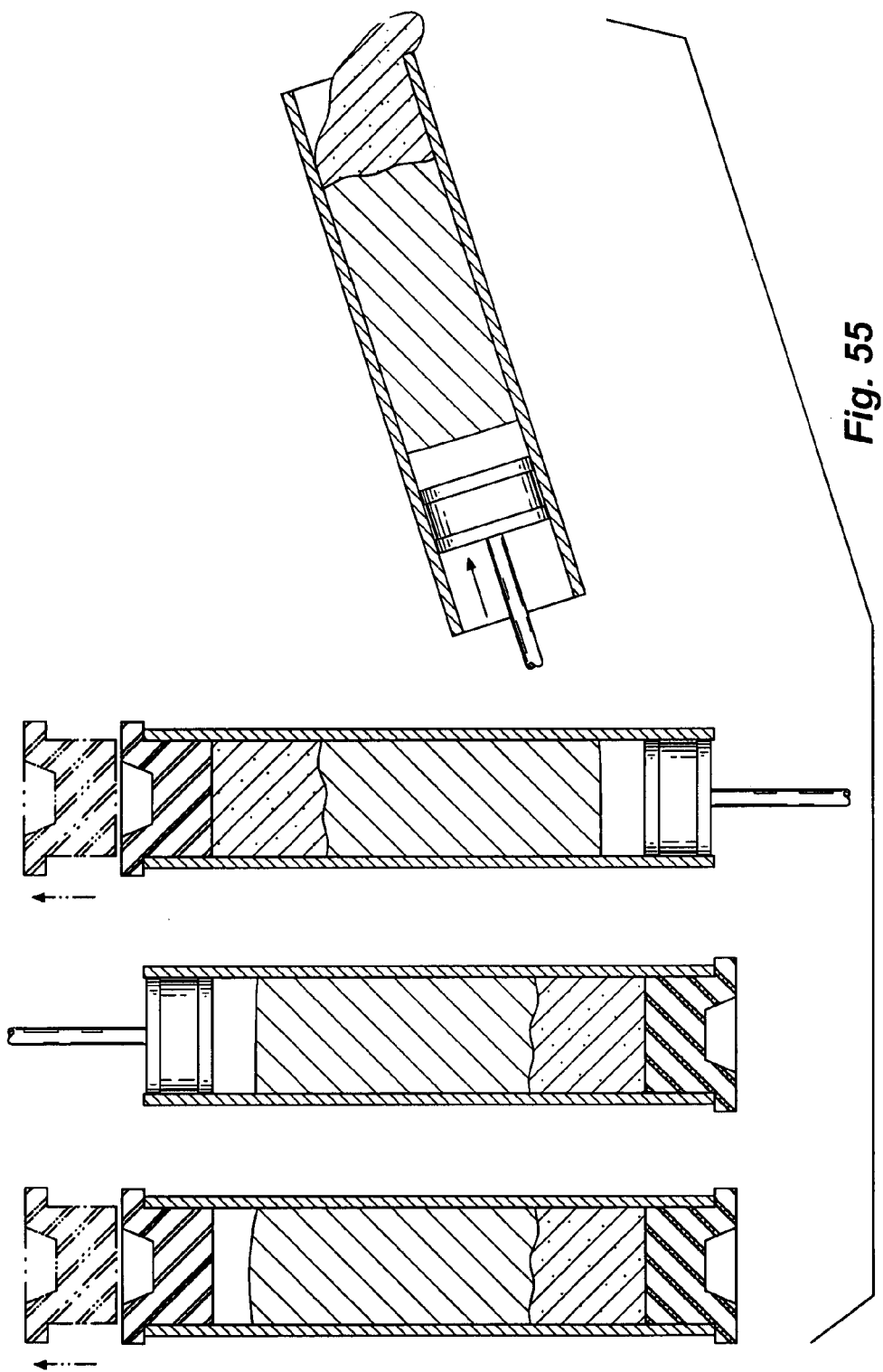

FIG. 55 is a partial cross-sectional sequence showing a dispensing system, in which the secondary tube has two stoppers.

Figure 56:
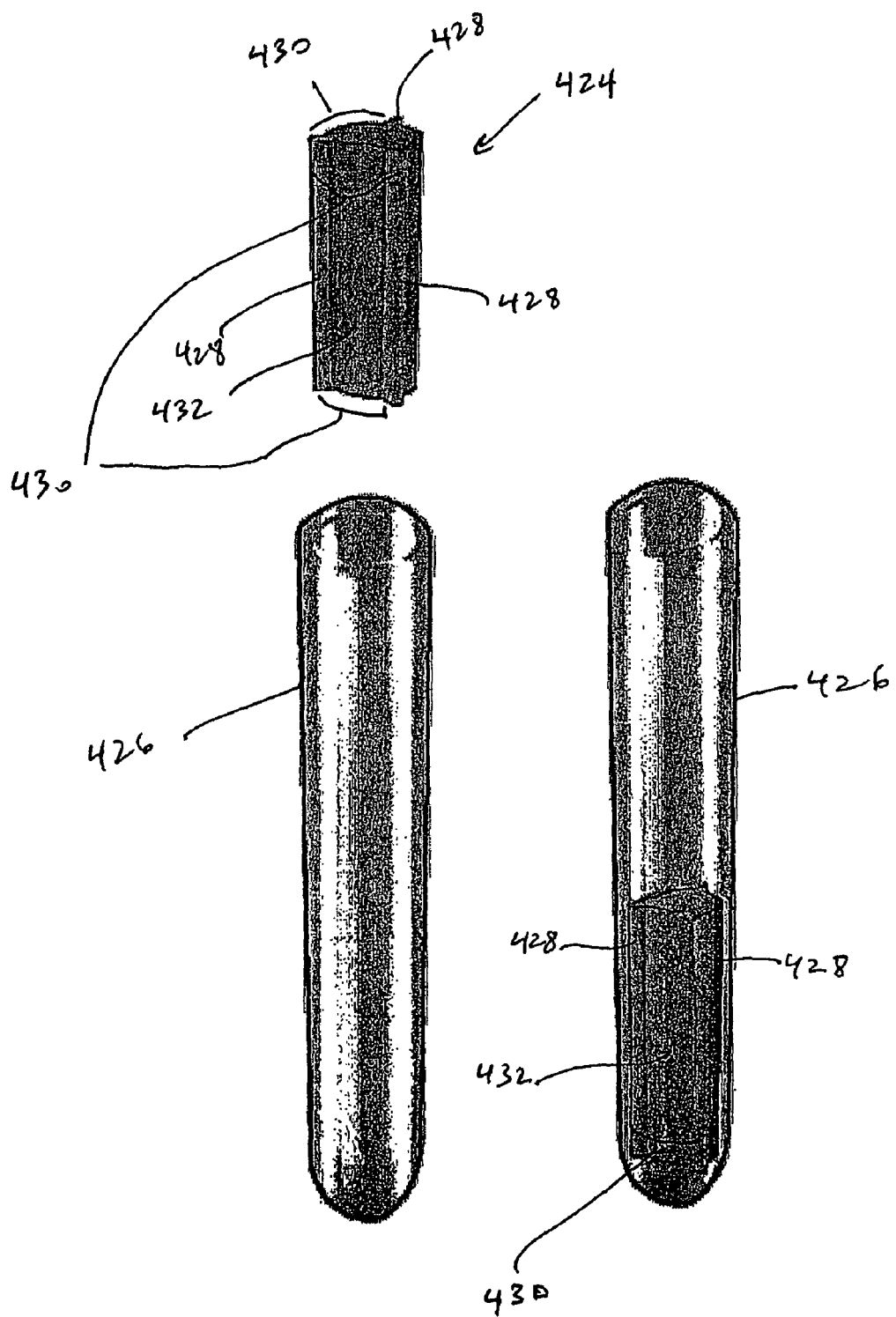

FIG. 56 is a perspective view of a moldable insert embodying the invention.

Before one embodiment of the invention is explained in detail, it is to be understood that the invention is not limited in its application to the details of construction and the arrangement of components set forth in the following description or illustrated in the drawings. The invention is capable of other embodiments and of being practiced or being carried out in various ways. Also, it is to be understood that the phraseology and terminology used herein is for the purpose of description and should not be regarded as limiting.

DETAILED DESCRIPTION OF THE INVENTION

This application hereby fully incorporates by reference the subject matter of U.S. Pat. No. 6,368,298, which issued on Apr. 9, 2002. This application also hereby fully incorporates by reference the subject matter of U.S. patent application Ser. No. 10/053,247 filed on Jan. 15, 2002, as well as the subject matter of U.S. Patent Application No. 60/392,669 filed on Jun. 27, 2002.

The present invention may provide a ready-to-use kit, allowing autologous fibrin glue to be rapidly obtained at least partially alleviating viral infections and/or rejection cases when used in surgery.

This may be achieved by using a coagulation activator, being neither of human nor of animal origin, but rather an inorganic compound which therefore cannot be infected and does not result in rejection.

The "ready to use" kit according to the present invention may comprise a sealed container containing calcium chloride as coagulation activator. Calcium chloride activates the fibrinogen present in patient's plasma when this is introduced into the sealed container.

The systems and kits according to the present invention have the great advantage of allowing the preparation of autologous fibrin glue which may be used with no risk of viral infections or rejection cases. The kit according to the present invention may also allow the preparation of autologous fibrin glue from patient's plasma in a very short time as well as in the formation of clots or membrane or spray. The ready-to-use kit according to the present invention may also allow the autologous fibrin glue to be obtained at costs proportionally lower with respect to the known systems. Also, the ready-to-use kit may also provide platelets and their associated growth factors for rapid tissue regeneration.

Further advantages of the kit according to the present invention will be evident to those skilled in the art from the following detailed description of some embodiments thereof.

Containers suitable for the kit according to the present invention include a glass container for antibiotics as hereinafter described in Example 1. Also glass or plastic test-tubes may be used. The preferred volume of the container is from 5 to 15 ml. The test-tubes have preferably a diameter ranging from 12 to 16 mm and a height ranging from 75 to 100 mm. The container should be suitably thick in order to withstand the stresses resulting from the pressure difference between its inner space and the atmosphere when it is evacuated. Hemispherical or conical bottom tubes are preferably 0.7 mm thick, flat bottom tubes 1 mm thick. The plastic containers are preferably made of transparent polyester resin, 0.2-0.8 mm thick, in order to ensure the vacuum keeping for at least 12 months after production. After the preparation, the plastic test-tubes, are preferably introduced into a tin-foil vacuum air-tight container having a heat-sealed inner polyethylene layer in order to ensure a perfect air-tightness until the date of use.

It should be noted that the evacuation of containers or test-tubes is advisable, however, not necessary for putting the present invention into practice.

The containers or test-tubes may be sealed by rubber or silicone pierceable caps, being suitable to ensure the container to be perfectly air-tight and to allow the vacuum plugging after the introduction of the chemical components and before the steam or radiation sterilization step.

After the sealing, the containers may be sterilized under steam at 121° C. for 30 minutes. The sterilization may be carried out also by irradiation with gamma rays or electron beam.

While a fibrin stabilizer tranexamic acid can be used, pure and crystalline epsilon-amino-caproic acid is also suitable. The amount will be about 1 g when using a 25 ml container, suitable for a plasma amount of 20 ml. Sometimes it is not necessary to use a fibrin stabilizer. Other performance enhancing therapeutic agents may be added to the second container for inclusion into the fibrin and platelet network. Examples include, but are not limited to, bone and soft tissue graft and scaffolding materials, antibiotics, analgesics, stem cells, chemotoxic agents for cancer therapy, immunosuppressants, engineered cells for expression of desired molecules, and combinations thereof.

As a coagulation activator, solid $CaCl_2.2H_2O$ or a liquid solution containing calcium may be used in the kit according to the present invention although other coagulation activators (listed below) can be used. For example, 11.76 mg of $CaCl_2.2H_2O$ can be introduced in a 5 ml container, by using a precision dosimeter (maximum error: 1-2 mg), in order to prevent polluting foreign components to be introduced. Alternatively, other cationic species, such as magnesium, manganese or zinc ions, which have a higher affinity to the anticoagulant than the endogenous calcium, can be used in place of divalent calcium cations. Upon addition to the anticoagulated platelet-rich plasma (PRP), the endogenous calcium ions are displaced from the anticoagulant by the higher affinity cationic species and the original endogenous calcium ions are available for clot activation.

In case of a 15 ml container for a plasma amount of 12 ml, the solid dehydrated calcium chloride amount to be introduced will be as high as 35.28 mg, while the tranexamic acid amount will proportionally be as high as 300 mg of crystals.

In case of a 25 ml container for a plasma amount of 20 ml, the dehydrated calcium chloride amount to be introduced will be as high as 58.8 mg while the tranexamic acid amount will proportionally be as high as 500 mg of crystals. Besides the dehydrated form used in the Examples, the calcium chloride may be in any other suitable form available on the market, e g. as $CaCl_2.2H_2O$. Also a solution of this salt can be used, as described in Example 1 below.

The present invention also provides systems and methods for forming a solid-fibrin web or autologous glue capable of regenerating tissue in a living organism. In these methods and systems, anticoagulated plasma is obtained by centrifugation of a blood sample. The transfer devices described herein enable the plasma to be transferred to a second container containing calcium-clotting agents and then immediately centrifuged in order to obtain a stable, dense, autologous fibrin and platelet network. The transfer devices described herein may also be used to transfer other liquids in other applications. In other words, the methods, transfer devices and systems described herein enable concurrent centrifugation and coagulation. By using these systems and methods, at least one of the following may be achieved: 1) the sample is manipulated in a manner by which sterility is maintained; 2) the total volume of plasma is transferred to maximize a full yield of a clot; 3) the stoichiometric ratio of anticoagulant and calcium clotting agent is maintained in a narrow range to minimize clotting time; 4) the transfer is completed quickly and can be performed inter-operatively within the half life of the platelet-derived growth factors; 5) health care providers not normally performing these operations (e.g. dentists) can easily perform these methods and operate the systems; and 6) the devices are single use in order to prevent re-use and possible contamination by blood-borne pathogens.

Generally speaking, the invention provides integrated systems and methods for preparing a solid-fibrin web or autologous glue which can be used to regenerate tissue in a living organism. In one embodiment (shown in FIG. 1), the system comprises a primary container 10, a secondary container 14 and a transfer device 18. Preferably, the primary and secondary containers 10, 14 are tubes, and more particularly, test tubes, although any container that is capable of holding a fluid or liquid and being centrifuged is suitable for use with the invention. Preferably, the containers 10, 14 are made from glass or plastics.

The primary container 10 should be capable of drawing blood therein using standard venipuncture techniques. Preferably the primary container 10 is sealed with a seal 22 while the blood is being drawn to prevent contamination, although the container 10 may be sealed shortly thereafter. A variety of seals 22 can be used to seal the primary container 10, e.g., a rubber stopper, cap, foam, elastomer or other composite. The seal 22 should be capable of being pierced or punctured, and therefore rubber and silicone are preferred materials from which the seal is fabricated, although any material that provides a seal and is capable of being pierced can be used. The primary container 10 may contain an anticoagulant solution 25. The anticoagulant 25 in the solution preferably comprises a calcium-binding agent. More particularly, the anticoagulant 25 may comprise sodium citrate, ethylenelendiaminetetraacetic acid disodium salt, ethylenelendiaminetetraacetic acid dipotassium salt and tripotassium and combinations thereof. Preferably, the primary container 10 contains a sodium citrate solution. The anticoagulant 25 tends to thin blood collected in the primary container 10 in order to place it in condition for centrifugation. In addition, the primary container includes a density-gradient separation medium 26, air 27 as well as a high-viscosity, low-density fluid 28 (see FIG. 10 which shows a kit further described below).

The density-gradient separation medium 26 must be capable of separating different fractions of a particular liquid or fluid in the primary container 10 having different densities. The separation medium 26 allows for dense, unwanted fractions of the liquid to be separated by centrifugation, and subsequently removed. For example, the separation medium 26 may separate red blood cells 30 from platelet-rich plasma 34 during centrifugation of a blood sample. In one example, the separation medium 26 may be found in the bottom of the primary container 10. In other examples, the separation medium 26 may be applied as a ring around the interior of the primary container 10, or any other suitable interior position. Although any density-gradient separation medium 26 capable of separating liquids having different densities during centrifugation is suitable for use with the invention, preferably the medium 26 is a gel, and more preferably, a thixotropic gel. FIG. 2 illustrates the primary container 10 after centrifugation of a blood sample has taken place, and also shows the gel separation medium 26. Preferably, the thixotropic gel has a sufficient yield point such that it does not flow in or move about the primary container 10 at ordinary ambient conditions, but does flow at higher centrifugal forces experienced during centrifugation. Most preferably, a gel having a density that is less than the high density of the unwanted red blood cell fraction 30, but greater than the density of the desired plasma fraction 34 is preferred. In other words, most preferred is a gel or other medium that is capable of separating red blood cells 30 from plasma 34 after a blood sample is centrifuged. Such a medium 26 will move or flow within the container during centrifugation, but does not flow thereafter, thereby creating a semi-permanent barrier between separated fractions when centrifugation is complete.

As shown in FIG. 3, another suitable density-gradient separation medium 26 which can be employed in the primary container 10 is a plurality of plastic beads 26 possessing the desired density for fraction separation. The beads may be suspended in the high viscosity, low-density fluid required for later sealing the transfer device 38. During centrifugation, the beads 26 migrate to the interface between the two fractions 30, 34 and are compacted, much like sintering, to form a stable barrier between the fractions having different densities (i.e. red blood cells 30 and the plasma 34). The residual high-viscosity, low-density fluid that coats the pellets contributes to the stability of the compacted layer.

Other suitable density-gradient separation medium include polymeric float devices such as those disclosed in U.S. Pat. Nos. 5,560,830 and 5,736,033 issued to Coleman, which are hereby incorporated by reference. FIG. 4 shows a polymeric float device 26.

The low-density, high-viscosity immiscible fluid 28 ("LDHV fluid") in the primary container generally comprises an inert oil. Most preferably, the LDHV fluid comprises polyester, silicone or another inert fluid, and is applied to the primary container in a position above the gel by displacement or pressure pumps. The LDHV fluid must be capable of blocking or eliminating flow through the cannula 38 of the transfer device 18 upon entry therein as further described below.

The secondary container 14 (shown, inter alia, in FIGS. 1 and 10) contains the chemical reagents necessary for particular reactions. The second container 14 is sealed by a seal 24 in a similar manner as the first container 10, i.e. by a rubber stopper, cap, foam, elastomer or other composite. In one application of the invention as discussed below, the secondary tube may contain a calcium-coagulation activator 36. Examples of suitable calcium-coagulation activators include, but are not limited to, calcium chloride, calcium fluoride, calcium carbonate and combinations thereof, however, any salt containing calcium will suffice as a calcium-coagulation activator. In addition, other activators include calcium gluconate, calcium fumarate, calcium pyruvate and other organic calcium salts that are soluble in water and are compatible with human life. The coagulation activator coagulates the plasma when it comes in contact therewith. The secondary container 14 may be fully evacuated to an internal pressure that is substantially zero. Evacuating the secondary container 14 facilitates the transfer of fluid from the primary container 10 to the secondary container 14 through the transfer device 18. Because no gas molecules are present as the secondary container 14 is filled during transfer, there is no compression of the residual gas with resulting pressure increase. As a result, the flow rate is maximized, complete transfer is facilitated, sterility is maintained by eliminating the need for venting and the desired stoichiometric ratio for the desired reaction is maintained.

In another embodiment, the secondary container may also contain one or more therapeutic enhancing agents such as antibiotics, analgesics, cancer therapeutics, platelet-growth factors, bone morphogenic proteins, stem cells, bone graft materials, soft tissue graft and cell culture materials, immunosuppressants and combinations thereof. Other therapeutic agents which can be topically administered may also be included. Examples of antibiotics include, but are not limited to, ampicillin, erythromycin, tobramycin and combinations thereof. Analgesics include, but are not limited to, aspirin, codeine and combinations thereof. Cancer therapeutics include, but are not limited to, 5-fluor-uracile. Bone graft materials include, but are not limited to, autologous bone, allograft or homograft from cadavers, animal-derived bone (xenografts or heterografts; e.g. ovine, bovine, porcine, equine), synthetic bone grafts (tri-calcium phosphate, hydroxyapatite, calcium sulphate ceramics), orthobiologic compounds (platelet derived growth factors (PDGF)), bone morphogenetic protein (BMP), recombinant human bone morphogenetic protein (rhBMP), and combinations thereof. Soft tissue graft and cell culture materials include, but are not limited to, skin, skin graft materials (Apligraf marketed by Organogenesis), gingival graft (e.g. from soft palette), collagen, bio-absorbable grafts, vascular grafts, PDGF, Platelet Factor 4(PF4), thromboglobulin, thrombospondin, TEFLON™ brand non-stick coating and DACRON™ brand polyester fiber by DuPont and combinations thereof. Immunosuppressants include, but are not limited to, immunosuppressants for organ transplants (e.g. cortico steroids, calcin neurin blockers (cyclosporin, tacrolimus, SK506), mycophenolate mofetil, rapamicin) and cutaneous immunosuppressants (serolimus, spingosine 1-phosphate receptor agonist (STY720)). Living cells for expression of desired molecules and gene therapy may also be included.

The transfer device 18 may comprise two pieces as shown, e.g., in FIG. 1 or, alternatively, may be one piece as shown, e.g., in FIGS. 17-18. As best shown in FIGS. 5-6 and 17-18, the transfer device 18 comprises a cannula 38 having a first end 42 having a first opening 46 and a second end 50 having a second opening 54. The ends 42, 50 of the cannula 38 are sharp or pointed (or even have a bevel ground on them) so as to be able to puncture or penetrate the seals 22, 24 of the primary and secondary containers 10, 14. The cannula 38 is recessed and coaxially mounted within the housing 58 in order to prevent accidental finger stick during manipulation of the containers. The housing 58 has two cylindrical, opposed guides 62, 64 which are centrally and axially oriented with the cannula 38. The guides 62, 64 serve to guide the primary and secondary containers 10, 14 onto the first and second ends 42, 50 of the transfer device 18. FIGS. 5 and 6 show the guides 62, 64 guiding the containers 10, 14 onto the first and second ends 42, 50.

The ends 42, 50 of the cannula 38 may be encompassed or covered by safety valves, sheaths or elastomeric sleeves 68, 72, which form a hermetic seal. The safety sheaths 68, 72 also cover the first and second openings 46, 54. When the first and second ends 42, 50 puncture the elastomeric sleeves 68, 72, the sleeves 68, 72 retract accordingly. FIG. 5 shows the first end 42 beginning to puncture the seal 22 of the primary container 10 and the sleeve 68 being retracted accordingly, while sleeve 72 still fully covers the second end 50. The ends 42, 50 extend far enough to fully puncture the seals 22, 24, but not extend much further into the containers 10, 14 (as shown in FIG. 6). This allows maximum volume transfer of the inverted primary container's 10 liquid volume to the secondary container 14. FIG. 6 also shows the first and second ends 42, 50 having fully punctured the seals 22, 24 of the first and second containers 10, 14, and both of the sleeves 68, 72 being fully retracted. The elastomeric sleeves 68, 72 prevent the flow of gas or liquid when not punctured. Suitable materials for the sleeves 68, 72 include, but are not limited to, rubber varieties and thermoplastic elastomers.

Turning now to the operation of the first embodiment, once blood has been drawn into the primary container 10 using standard venipuncture techniques, the blood is anticoagulated by the anti-coagulant 25 therein. Typically, the primary container 10 is sealed while the blood is being drawn, however, it may be sealed thereafter. Sealing the primary container 10 prevents contamination of the contents therein. Thereafter, the primary container and its contents 10 (i.e. blood, anti-coagulant 25, separation medium 26 and LDHV fluid 28) are centrifuged. Acceptable centrifugation can take place at a gravitational force in the range of 900 to 3,500×G for 5 to 15 minutes. In a preferred embodiment, the primary container is centrifuged at a gravitational force of about 1,000×G for about ten minutes. This initial centrifugation separates the primary container's contents or fractions into a plurality of layers as shown, e.g., in FIG. 2. The layers include (in order from the bottom of the primary container 10 to the top of the container after centrifugation): the red blood cell layer 30, the separation medium 26, the platelet-rich plasma layer 34, the LDHV fluid layer 28, and finally a residual gas 27 volume at a pressure equal to atmospheric. The proportions of these layers may vary from application to application, and are shown here in these proportions for illustrative purposes only. Subsequent to centrifugation, the sealed primary holder 10 is inverted before the transfer device 18 is used to puncture the seal 22. In other words, the primary container 10 is inverted such that the sealed opening is in the lowest vertical position as shown in FIG. 7. Inverting the primary container changes the order in which the layers are arranged. Above the seal 22 are the following layers in sequence from bottom to top: the platelet-rich plasma 34, the high-viscosity, low-density immiscible fluid 28, the residual gas 27, the separation medium 26 and the red blood cells 30.

Next, the secondary container 14 is placed in a vertical position with its sealed opening 24 in the topmost position as best shown in FIG. 8. This positions the secondary container 14 for the transfer of the primary holder's contents therein. FIG. 8 illustrates the centrifuged primary container 10 in the inverted position above the transfer device 18, which is above the secondary container 14 in the proper position for transfer. The transfer device's guide 64 is then placed over and guides the secondary container 14 therein, while the inverted primary container 10 is then placed into the other guide 62 (or vice-versa). In other words, either end 42, 50 of the cannula 38 can be used to puncture either seal 22, 24. Because the transfer device 18 is symmetrical on either end, the user is provided a degree of foolproof operation. The user then forces the containers together in order to puncture both seals 22, 24 with each respective cannula end 42, 50. The two valve sleeves 68, 72 covering the ends 42, 50 further enhance the foolproof operation. First, if the first end 42 punctures the primary seal 22 (again, either end can be used to puncture either seal), the unpunctured sleeve 72 covering the other end 50 will contain the fluid, thereby preventing the fluid from spilling. On the other hand, if the other end 50 punctures the other seal 24 (and the sleeve 72 accordingly) first, the vacuum is maintained by the sleeve 68 covering the first end 42.

Once the ends 42, 50 puncture both sleeves 68, 72 and seals 22, 24 as shown in FIGS. 6 and 9, the desired fluid is transferred from the primary container 10 to the secondary container 14 by pressure differential. In other words, because the pressure in the secondary container 14 has been evacuated, the contents (more particularly, the plasma 34) of the primary container 10 flow into the secondary container 14. The pressure in the primary container 10, originally at atmospheric, decreases as the liquid level diminishes and the gas volume expands. At no point, however, is the pressure equal to zero. Because the secondary container 14 is fully evacuated to a pressure equal to or slightly greater than zero, the pressure therein does not increase as the tube is filled since there is little or no gas to compress. Accordingly, the apparatus 18 may be used to transfer a wide variety of liquids and solutions from one tube to another, and should not be construed to be limited only to the transfer of blood.

Because of the particular sequential arrangement of the layers in the primary container 10, the platelet-rich plasma 34 is easily transferred. In addition, because the primary container 10 is also preset to an evacuation level, the container only partially fills after blood collection. This allows the gas in the "head space" to remain significantly above zero during transfer when its volume is expanded, thereby allowing fast and complete transfer to the secondary container 14. This is dictated by the ideal gas law and the Poiseuille-Hagen equation.

Transfer of the contents or fragments of the primary container (i.e. the platelet-rich plasma) continues until the LDHV fluid 28 enters the cannula 38. The LDHV fluid's high viscosity plugs the narrow lumen of the cannula 38, thereby resulting in flow discontinuance. This prevents reuse of the transfer device 18, which is particularly important in trying to eliminate contaminated blood transfer devices, and also prevents accidental contamination by blood borne pathogens by prior use on or by another patient.

The transfer of the plasma fraction 34 to the secondary container 14 is complete, thereby allowing maximum yield and maintenance of the appropriate stoichiometric ratio of reagents. The plasma 34 then contacts the coagulation activator 36 in the second container 14, thereby creating a mixture 60 which can be immediately centrifuged to form a solid-fibrin web. The pressure differential between primary and secondary containers 10, 14 is substantially maintained throughout transfer, allowing rapid transfer. The transfer device 18 is unaffected by order of tube engagement, rendering the system virtually foolproof. Finally, the transfer occurs without venting, maintaining sterility and non-contamination of the sample.

Overall, the transfer device 18 provides a quick and efficient way of contacting the plasma 34 with the calcium-coagulation activator 36, immediately subsequent to which concurrent coagulation and centrifugation of the plasma can take place in order to form the solid-fibrin web. The solid-fibrin web is suitable for regenerating body tissue in a living organism. Such a method alleviates the need to first preconcentrate the plasma by removing water therefrom before the plasma is contacted with the calcium-coagulation activator 36. In addition, the transfer device 18 can be used to transfer blood or other fluids in a wide variety of application.

The invention also provides a ready-to-use kit as shown in FIG. 10. The kit comprises the primary container 10, the secondary container 14 and the transfer device 18. In one embodiment of the kit, the kit may have two trays 70, 74 that lift out of a package. The first tray 70 has all the components necessary for Step 1 and the second tray 74 has all the components required for Step 2. Of course, the components can be arranged in a wide variety of manners.

Step 1 comprises collecting blood into the primary container 10, followed by centrifugation to obtain platelet-rich plasma. The components of the first tray 70 comprise an alcohol swab 78 to cleanse the venipuncture site, a multiple sample blood collection needle 82 (21 gauge×1"), a safety holder 86, the primary container 10 containing the anticoagulant (e.g. citrate), gel, LDHV fluid and a bandage 90 to cover the venipuncture site. The venipunture site is cleansed with the sterile alcohol swab 78. The needle cartridge 84 is opened and screwed into the safety holder 86. The needle 82 is then inserted into the patient's vein and the container 10 is connected to the holder 86. Blood then fills the container, and the needle 82 is withdrawn and retracted into the holder 86. The end of the holder is closed with the hinged flap. The vein is closed with the bandage 90. The container 10 is centrifuged at about 1000×G for about 10 minutes and the plasma is separated from the red blood cells.

The components of the second tray are the components used for step 2 include an AFTube (Autologous Fibrin Tube) or secondary container 14 and a transfer device 18. Step 2 comprises placing the primary container 10 in an inverted position and into the transfer device 18. The secondary container 14 contains the coagulator and is punctured by the other end of the transfer device. The containers 10, 14 are joined and the platelet-rich plasma flows from the primary container 10 to the secondary container 14. The secondary container is then immediately centrifuged at 2300×G for about 30 minutes to obtain dense fibrin with platelets or a solid-fibrin web.

In a second embodiment of the invention, another integrated system for preparing a solid-fibrin web is provided as shown in FIGS. 11-14. The system comprises a primary collection device 10, which is very similar to the primary container 10 of the first embodiment. The collection device 10 may contain a density-gradient-cell separating medium 26 (as described above) and an anticoagulant (not shown) as well as a reservoir 94 that can be connected to the primary collection device 10 or integral therewith. The discussion above pertaining to the first embodiment of the invention, and more particularly, to the separation medium 26 applies to the second embodiment of the invention. In other words, the same materials can be used for the separation medium 26, and the same materials are preferred. For example, most preferably the separation medium 26 comprises a thixotropic gel, the yield point of which prevents it from flowing at ordinary ambient conditions, but allows it to flow at the higher centrifugal forces experienced during centrifugation. The separation medium 26 may be located at the bottom as shown in FIG. 11 (i.e. the opposite end from the opening) of the primary collection device. Alternatively, the separation medium may form a ring around the interior of the primary collection device. The primary collection device 10 is essentially the same as the primary container 10 described above, except that the primary collection device may not contain a high-density, low-viscosity fluid. Preferably, the primary collection device 10 has a seal 22 such as a rubber stopper or cap (as discussed above).

The reservoir 94 comprises a chamber 96 and a cannula 100 in fluid communication therewith. The chamber 96 contains a liquid reagent 104, most preferably a calcium-coagulation activator. Preferably, the calcium-coagulation activator is calcium chloride, calcium fluoride, calcium carbonate, calcium gluconate, calcium fumarate, calcium pyruvate or a combination thereof. The cannula 96 must be capable of puncturing the seal 22 of the primary collection device 10. In a preferred embodiment, the cannula contains a blocking medium 108 such as a yield-point gel that prevents the reagents 104 in the chamber 96 from flowing out of the cannula 100 under ambient conditions. Other suitable blocking mediums include, but are not limited to, force-actuated mechanical systems such as balls on springs, valves, spring-loaded valves, pierceable membranes and ampoules (i.e. hollow membranes filled with fluids or powders). The yield point of the gel 108 is such that upon centrifugation at a particularly high gravitational force, the gel 108 moves in order to allow communication between the chamber 96 and the primary collection device 10 when the two are engaged. The reservoir 94 may also have a guide housing 110 used to guide the reservoir onto the collection device 10. The cannula 100 may be encompassed or covered by an elastomeric sleeve 112 to maintain sterility of the cannula 100. The sleeve 112 is discussed above with regard to the first embodiment.

In another embodiment, the chamber 96 may also contain one or more of an antibiotic, an analgesic, a cancer therapeutic, a platelet-growth factor a bone morphogenic protein cells for gene therapy, stem cells for additional uses, and other hormones. Other therapeutic agents which can be administered may also be included. Examples of antibiotics include, but are not limited to, ampicillin, erythromycin and tobramycin. Analgesics include, but are not limited to, aspirin and codeine. Cancer therapeutics include, but are not limited to, 5-fluor-uracile.

In operation, a patient's blood 116 is collected into the primary collection device 10 by conventional venipuncture technique as described above. The anticoagulant in the primary collection device 10 thins the blood before centrifugation. Subsequently, the reservoir 94 is then attached to the primary collection device 10 by piercing the cannula 100 of the reservoir 94 through the seal 22 of the primary collection device 10 as shown in FIGS. 13 and 14. The sleeve 112 retracts when the cannula 100 pierces the seal 22. The length of the cannula 100 is sufficient to puncture the seal 22, but the cannula preferably does not extend much further into the collection device 10, although it could.

The collection device 10 and the reservoir 94 are then centrifuged. The centrifugal force exerted on the tube is described by the equation $F=m\omega^2 r$; where F=force, m=mass of system, r=radial distance from the center of the rotor, and ω=is the rate of angular rotation. Since the reservoir is at a smaller r than the primary tube gel, the gel in the reservoir's cannula cannot move since insufficient shear stresses are generated. The primary tube 10 spins at the low gravitational force until the cells separate and the gel 26 moves to the cell/plasma interface as shown in FIG. 13. In other words, similar to the first embodiment, the separation medium 26 separates the red blood cells 30 from the platelet-rich plasma 34 after an initial centrifugation at about 1000×G for about 10 minutes. Centrifugation at a centrifugal force of about 900-1500×G for about 5 to 15 minutes is also acceptable for the initial centrifugation.

Subsequently, the centrifuge speed is increased and the reservoir experiences sufficiently high gravitational force such that the blocking medium 108 in the cannula 100 empties into the primary collection device 10 and the liquid reagant 108 (e.g. the calcium-coagulation activator) is emptied from the reservoir as shown in FIG. 14. The contents may subsequently be centrifuged at about 2300-6000×G for about 15-40 minutes. As the calcium-coagulation activator contacts the plasma in the primary collection device, immediate and concurrent coagulation and centrifugation occurs because the sample is still being centrifuged. This results in the formation of a solid-fibrin web suitable for the regeneration of tissue. The operation of primary tube cell separation and subsequent addition of the liquid clotting agent at the right stoichiometric ratio is performed in one tube without transfer. By programming the centrifuge with regard to speed and duration, the invention provides a simple and foolproof process.

In an alternative embodiment, the single collection device 10 has an interior compartment 119 and a reservoir 94 as shown in FIGS. 15-16. The reservoir 94 is integral with or connected to the primary collection device 10 and in fluid communication with the compartment. A tube, conduit or opening 120 provides the fluid communication between the compartment 119 and the reservoir 94, and is sealed with the blocking medium 108. Again, the blocking medium 108 has a yield point that is activated and moves when exposed to a particularly high gravitational force in order to allow communication between the reservoir 94 and the primary collection device 10 as described above. The gel or medium's yield point is such that it does not move during initial centrifugation to separate blood cells from the plasma. In the third embodiment, each end of the device has an opening and each end is sealed by a removable or non-removable seal 22, 122 such as a rubber stopper, cap, foam, elastomer or other composite. The reservoir 94 with stopper 122 is located at the opposite end of the collection device's seal 22 and opening.

In another embodiment, the reservoir 94 may also contain one or more of an antibiotic, an analgesic, a cancer therapeutic, a platelet-growth factor and a bone morphogenic protein. Other therapeutic agents which can be administered may also be included. Examples of antibiotics include, but are not limited to, ampicillin, erythromycin and tobramycin. Analgesics include, but are not limited to, aspirin and codeine. Cancer therapeutics include, but are not limited to, 5-fluor-uracile.

The alternative embodiment is used in the same manner as described above with respect to the second embodiment, i.e., the centrifuge is controlled at two different centrifugal forces: 1) the first being a force sufficient to separate the plasma from the red blood cells; and 2) the second being a force sufficient to move the blocking medium 108 in the tube, conduit or opening 120 between the reservoir and the interior of the device and into the main body. As a result, the calcium-coagulation activator is allowed to enter the interior of the device. This in turn enables concurrent centrifugation and coagulation of the plasma in order to form the solid-fibrin web as centrifugation proceeds at the second, higher gravitated force. The seal 122 may be removed in order to obtain the solid-fibrin web or autologous glue. In a preferred embodiment, the seal 122 is threaded and can be screwed out of the device 10 as shown in FIG. 16.

In one aspect, the invention provides a system for preparing an autologous solid-fibrin web suitable for regenerating tissue in a living organism. The system comprises a sealed primary container containing a separation medium and a low-density high-viscosity liquid. The separation medium is capable of separating red blood cells from plasma when the container contains blood and is centrifuged, and the primary container has a first pressure. The system further comprises a sealed secondary container containing a calcium-coagulation activator. The secondary container has a second pressure that is less than the first pressure. The system also comprises a transfer device including a cannula having a first end and a second end. The first and second ends are capable of puncturing the sealed primary and secondary containers in order to provide fluid communication between the first and second containers. The low-density high-viscosity liquid of the primary container is capable of blocking flow through the cannula upon entering therein.

In another aspect, the invention provides another system for preparing a solid-fibrin web capable of regenerating tissue in a living organism. The system comprises a sealed primary container having a first pressure that is capable of having blood drawn therein. The system further comprises a sealed secondary container having a second pressure and containing a calcium-coagulation activator. The second pressure is less than the first pressure. The system also comprises a transfer device including a cannula having a first end and a second end. The first and second ends are capable of puncturing the sealed containers, and the transfer device is capable of transferring a portion of blood drawn in the primary container to the second container by pressure differentiation. The system also includes a centrifuge for concurrently centrifuging and coagulating the portion of blood transferred from the primary container to the secondary container through the transfer device and brought into contact with the calcium-coagulation activator in order to form a solid-fibrin web that is capable of regenerating tissue in a living organism.

In another aspect, the invention provides a method of preparing a solid-fibrin web for regenerating body tissue in a living organism. The method comprises drawing blood from a patient into a primary container and separating plasma from the blood in the primary container. Plasma from the primary container is transferred to a secondary container containing a calcium-coagulation activator using a transfer device comprising a cannula having a first end and a second end in order to contact the plasma with the calcium-coagulation activator. The plasma and calcium-coagulation activator are concurrently coagulated and centrifuged in the secondary container in order to form a solid-fibrin web. The solid-fibrin web is suitable for regenerating body tissue in a living organism.

In another aspect, the invention provides another system for preparing a solid-fibrin web suitable for regenerating tissue in a living organism. The system comprises a sealed primary collection device having an interior and containing a separation medium. The primary collection device is capable of having blood drawn into the interior, and the separation medium is capable of separating plasma from red blood cells when the primary collection device contains blood and is centrifuged. The system further comprises a reservoir having a chamber and a conduit in fluid communication therewith. The chamber has a calcium-coagulation activator therein, and the conduit is at least partially filled with a blocking medium to prevent the activator from flowing out of the chamber under ambient conditions.

In another aspect, the invention provides another method of preparing a solid-fibrin web capable of regenerating tissue in a living organism. The method comprises drawing blood from a patient into a primary collection device having a seal and providing a reservoir including a chamber and a conduit in fluid communication with the chamber. The chamber is at least partially filled a calcium-coagulation activator, and the conduit is at least partially filled with a blocking medium to prevent the activator from flowing out of the chamber under ambient conditions. The reservoir is connected to the primary collection device such that the chamber, conduit and collection device would be in fluid communication but for the blocking medium. The primary collection device is then centrifuged at a first rate. The first rate is sufficient to separate plasma from blood, yet not sufficient to move the blocking medium in the conduit into the primary collection device. The primary collection device is then centrifuged at a second rate. The second rate is sufficient to move at least a portion of the blocking medium from the conduit into the primary collection device, thereby allowing the calcium-coagulation activator to flow into the collection device and contact the plasma, thereby forming a solid-fibrin web suitable for regenerating tissue in a living organism.

Most of the systems discussed above, employ radial centrifugation (i.e. the axis of the tube is aligned perpendicularly to the centrifuge axis) during the second centrifuge in order to compress the clot. When these systems and devices are used, however, the centrifuge operation may not be performed inside the operating room due to sterility concerns. Therefore, in another aspect, the invention provides a sterile tube exterior into the operating room, collects the specimen under sterile conditions, transports the specimen outside of the operating room, processes the specimen in a centrifuge and then ensures sterility of the outside of the tube upon reintroduction into the operating room.

Accordingly, in conjunction with any of the two-tube systems discussed above, both the primary and secondary tubes may be packaged in an easy-to-remove film, or alternatively, a molded carrier. FIG. 52 shows a film design which may include shrink wrap having a tear strip or a serrated end having an easy-to-tear bottom. FIG. 52 shows a sterile tube carrier that permits introduction of the primary or secondary containers to a sterile field such as an operating room. The carrier may be shrink wrapped for an additional level of handling as shown in FIG. 53. The assembly may be sterilized by radiation. The assembly may then be opened in an operating room and the interior and exterior of the tube is maintained sterile. FIG. 53 shows a carrier design. The packaging is generally of minimal thickness during manufacture. Both the tube and wrap may be sterilized by radiation, providing sterility of inner and outer surfaces. Just prior to entry into the operating room, the film or carrier is removed from the primary tube and the sterile exterior tube enters the operating room. In addition, the external surface of the film, wrapped tube or carrier may be decontaminated or sterilized using appropriate chemicals known in the art before being introduced into the operating room. This allows the film, wrapper or carrier to opened inside the operating room, which assures absolute sterility of the product. Blood is collected and the tube exits the operating room and is centrifuged. The sterile plasma is transferred to the second tube having the activator, while it is in the film or container and centrifuged. Just prior to re-entry to the operating room, the outer wrapper is removed and a sterile product enters the operating room. An improvement in this design is the addition of a removable adhesive film to the primary tube's stopper, which allows sterile surface during the transfer operation.

In addition, when using any of the one-tube systems discussed above, the tube may have a film or carrier pre-assembled during manufacture. The assembly is placed in a hermetic pouch and the assembly is sterilized. The pouch is opened just before entering the operating room. Subsequently, the tube collects the blood, as the needle pierces the tube's stopper and film. An adhesive film may also be added to the tube stopper. The tube exits the operating room, and the liquid reservoir having the activator or other substance is added to the assembly. The two-stage centrifrugation takes place and the carrier is removed just prior to reintroduction to the operating room.

Overall, both the primary and secondary tubes may be maintained in a sterile film or carrier during processing and can be re-introduced into the operating room with a sterile exterior. The film or carrier is pre-assembled onto the tubes and their use is transparent to ordinary blood collection tube collection and centrifugation. The film or carrier can be constructed of materials that improve the shelf-life and reliability of the tubes by providing a permeation barrier to gas and water vapor, particularly useful for plastic tubes.

The discussion set forth above establishes a variety of methods and devices used to form dense fibrin and platelet networks and solid-fibrin webs by concurrent centrifugation and coagulation. Many of these devices and methods employ radial centrifugation, in which the axis of the tube may be aligned substantially perpendicularly to the centrifuge axis. For example, the tube may be aligned on the radius of the centrifuge, and may have the stopper near the center and the bottom of the tube toward the outer edge of the centrifuge. In most of the applications discussed above, it is during the second centrifuge cycle that the clot is compressed. As a result, the centrifugal force varies linearly along the length of the tube. The difference in centrifugal force can be used to an advantage by using differential speed of the centrifuge to activate additions of reagents. Radial centrifuges are the most common variety found in commercial use and their flexible uses are advantageous to the product designer, especially in view of their widespread availability.

A solid-fibrin web or fibrin-platelet network may refer to a substance formed by concurrent centrifugation and coagulation of plasma, or more particularly, platelet-rich plasma. As discussed above, the solid-fibrin web is useful in unlimited tissue regeneration applications. The fibrinogen in the plasma is converted to fibrin strands and sedimented concurrently with the platelet sedimentation. In the final step of the coagulation cascade, the fibrin strands crosslink in a random orientation, resulting in a gel like consistency. If very high centrifugal force is applied, the fibrin in compressed into a membrane of high strength. Accordingly, a membrane may refer to a solid-fibrin web that has been further compressed at a higher centrifugal or gravitational force (such as those forces set forth herein).

An alternative to radial centrifugation, however, is axial centrifugation. When using axial centrifugation, the container holding the liquid is rotated on its central axis. In other words, the container in essence acts as the rotor. As a result, a heavy rotor may no longer be necessary in the centrifuge. The axially-centrifuged container may generally be smaller in radius than a radial rotor, thereby requiring a higher rpm to achieve an equivalent g force. For example, instead of spinning the centrifuge up to 10,000 rpm, the centrifuge may be spun up to 200,000 rpms. Although the rpm requirement is higher, the significant reduction in weight minimizes the safety hazard and disproportionately lowers the cost of the motor. In other words, because the weight of the centrifuge is significantly reduced due to the removal of the rotor, the centrifuge may be spun at a much higher rpm.

Generally, the centrifugal force is proportional to the radius multiplied by the second power of rpm ($rpm^2$). In fact, significantly higher g forces may be obtained by this method. Significantly larger cylindrical areas are obtained at very uniform centrifugal field strength. Since the container is generally the rotor, axial centrifugation usually employs a single container operation, rather than batch. Therefore, even if a small tube is used and spun about its axis, the membrane covers more than a majority of the outside of the tube. More particularly, the surface area of the covered cylinder may be defined as about $2\pi rl$, wherein r is the radius of the cylinder and l is the length of the cylinder. In contrast, when using radial centrifugation, the surface area would essentially be the diameter of the tube. Therefore, using radial centrifugation produces a membrane equal to $2\pi rl$, whereas axial centrifugation produces a membrane equal $\pi r^2$.

Axial centrifugation may be accomplished in a variety of ways. For example, different cartridges may be placed in a modified existing rotor. Alternatively, the rotor may be removed and a disposable cartridge or container may be inserted in its place. Typically, the systems used in conjunction with axial centrifugation will employ two chambers, namely, a cell-separation chamber, in which blood is separated into red blood cells and platelet-rich plasma as well as a densification chamber, in which the platelet-rich plasma contacts the coagulation activator and is concurrently centrifuged and coagulated to form a membrane. Again, the membrane can be used in a wide variety of tissue regeneration and wound sealant applications.

In one embodiment, a sterile drum rotor disposable cartridge 200 is provided as shown, for example, in FIGS. 19-20. The cartridge 200 may be made from a variety of materials, e.g., a wide variety of ceramics, glasses and plastics. If not specifically stated, the devices and systems made herein may be fabricated from a wide variety of ceramics, plastics, glasses or other suitable materials. The cartridge 200 may generally be the shape of a circular crown's section adapted in such a way that it can be fitted inside a drum rotor of a centrifuge, although the shape is less important than the fact it has two chambers separated by a filtering device as discussed below. The shape of the section is such that it can be subsequently removed for fibrin-platelet-rich membrane recovery. In one embodiment, the cartridge 200 includes an inner chamber 204 defined by a central wall 208, side walls 212, a top and bottom wall 216, 220 and a filtering device 224. The inner chamber 204 acts as the cell-separation chamber discussed above. The top wall 216 may have a pierceable charging port 228 through which blood from a patient may be introduced or injected into the inner chamber 204. The filtering device 224 may be made of a selective centrifugable (mechanically supported) filter, which accepts a discrete amount of whole blood. The filtering device 224 may be made from a wide variety of materials including, but not limited to, polycarbonate, cellulose, polyethylene, polypropylene, nylon, or TEFLON®. The filter may have a pore size of about 4-9 microns. The inner chamber 204 may contain an anticoagulant 232, e.g., one or more of the anticoagulants discussed above with respect to the radial-centrifugation methods and devices. The anticoagulant 232 prevents blood entering the inner chamber 204 from clotting.

The cartridge 200 also has an external chamber 236, which generally has a smaller volume than the inner chamber 204. The external chamber 236 or peripheral tank is defined by the filtering device 224 and a peripheral wall 240 as well as top and bottom walls 216, 220 as shown in FIG. 20. The external chamber 236 may include a coagulation activator 244 such as one or more of the calcium-coagulation activators discussed above. The external chamber 236 acts as the densification chamber, in which the platelet-rich plasma is activated with the coagulation activator 244. These substances are concurrently centrifuged and coagulated to form the membrane. The densification chamber 236 may also contain one or more secondary active agents 248 or therapeutic enhancing agents. Secondary active agents 248 include, but are not limited to, one or more antibiotics, analgesics, cancer therapeutics, platelet-growth factors, bone morphogenic proteins, cells for gene therapy, stem cells for additional uses, other hormones and combinations thereof. Other therapeutic agents that can be administered may also be included. Examples of antibiotics include, but are not limited to, ampicillin, erythromycin and tobramycin. Analgesics include, but are not limited to, aspirin and codeine. Cancer therapeutics include, but are not limited to, 5-fluor-uracile. The secondary agents may be included in any of the densification chambers discussed herein, and more particularly, below. Secondary active agents or therapeutic enhancing agents are discussed in more detail above.

In operation, the cartridge 200 is inserted in the drum rotor (not shown) for centrifugation. The inner chamber 204 may already contain blood, or blood may be injected through the port 228 after insertion in the drum rotor. Injection of blood into the inner chamber 204 may be performed using standard venipuncture. In other words, the inner chamber 204 may be kept in a vacuum. An anticoagulant 232 may be used in the inner chamber 204 to prevent the blood from clotting. The port 228 maintains the sterility of the inner chamber 204, and provides a closed system. The drum rotor may accommodate several different cartridges. Generally, each cartridge 200 should be balanced inside the rotor by putting a similar cartridge or a counter balancing weight in the opposite site inside the rotor. Upon centrifuging the blood sample, the filter 224 retains the red and the white blood cells in the inner chamber 204, but allows plasma and platelets to flow therethrough to the external chamber 236 under proper centrifugal force for a predetermined time. The proper centrifugal force will likely fall in the range of 1000-15,000×g, and the predetermined time will likely be greater than 5 minutes, and more particularly, may be between 5 and 60 minutes or 5 to 30 minutes. Once the platelet-rich plasma enters the second chamber 236, if the cartridge, it contacts the coagulation activator 244.

As discussed herein with respect to this embodiment and the embodiments below, any of the coagulation activators 244 set forth above are suitable for use. Upon contacting the activator 244, the plasma is concurrently centrifuged and coagulated, thereby forming a solid-fibrin web or membrane. Providing a mixing movement of the rotor may be helpful to fully mix the plasma and the activator 244 in order to initiate the coagulation process. After mixing, the rotor may be spun at about 3000 to 15000×g for greater than 10 minutes, and more particularly, greater than about 20 minutes to obtain a white resistant fibrin-platelet rich membrane on the peripheral wall 240 of the second chamber 236. To extract the membrane from the cartridge 200, the device may be crunched or opened in two parts in order to take out the membrane for the application. Alternatively, one of the walls may have a removable portion or other access area through which the membrane may be obtained. Other ways by which to remove the membrane from the cartridge include rolling and folding the membrane. For sanitary purposes, the cartridge 200 may be disposable. The membrane has a wide variety of applications including, but in no way limited to, wound care and burn care. More generally, the membrane may be used in an unlimited number of tissue regeneration applications.

In another embodiment of the invention, known as the large axial spin, membranes, e.g., membranes up to, but not limited to, 1000 mm in diameter may be obtained. FIGS. 21-25 show this embodiment. The size of the membrane may depend on the size of the rotor. Accordingly, the size of the membrane may be dependent upon what rotors are commercially available. In this embodiment, both the primary and secondary centrifuge operations, discussed above with respect to the radial centrifugation methods and devices, are performed in one axial spin container. The secondary chamber may be partitioned to yield multiple discrete area membranes of large area. This partitioning is discussed in more detail below.

This system comprises a centrifuge (not shown) and a device 252 which can be inserted therein and which is shown in FIGS. 21-25. The device 252 has two chambers, namely, a primary or upper chamber 256 and a secondary or lower chamber 260 in fluid communication with one another. The primary or upper chamber 256 acts as the cell-separation chamber, while the secondary or lower chamber 260 acts as the densification chamber. The device 252, as shown in FIGS. 21-25, also includes a diaphragm 264 having at least one opening, aperture or vent defined therein. The diaphragm 264 separates the two chambers 256, 260. The opening, aperture or vent 268 provides fluid communication between the primary chamber 256 and the secondary chamber 260. The diaphragm 264 may, for example, be made from a plastic, ceramic or glass.

The primary chamber 256 may contain a separation medium 272. Any of the separating mediums 272 discussed above may be used in conjunction with the system, although specific examples of separating mediums 272 may include at least one of silicone gels, polyester gels, thixotropic gels and combinations thereof. More specifically, the vent or vents 268 of the diaphragm 264 may be plugged with the separating medium 272 (e.g., a gel) in an amount sufficient to block the vent or vents 268 and provide separation of the red blood cells from the plasma after a first centrifugation. The primary chamber 256 receives whole blood from a patient, usually through pierceable stopper 276 or other suitable device such as a lined screw cap, like a bottle cap. In FIGS. 21-25, the system is shown as having a pierceable stopper 276 through which blood may be introduced into the upper chamber 256. The primary chamber 256 may also contain an anticoagulant 232. The chamber 256 may also be evacuated to allow vacuum collection of the specimen by standard venipuncture. The secondary chamber 260 may contain a coagulation activator 244, and may contain one or more of the secondary active agents 248 discussed above.

After blood 280 has been collected into the upper chamber 256 as shown in FIG. 22, the device 252 is centrifuged axially at the proper g force to affect cell separation, namely, separation of red blood cells 288 from the platelet-rich plasma 284. Typical g forces used to affect cell separation may include 500 to 15,000×g for a predetermined time, such as, greater than 5 minutes. Preferably, initial centrifugation takes place at about 1000-1500×g for about 5 to 15 minutes. This applies to all of the embodiments pertaining to membranes set forth herein. The initial centrifugation moves the separation medium 272 from its position blocking the vents 268 to the interface. For example, a thixotropic gel 272 may maintain separation of the two chambers 256, 260 during filling of the primary chamber 256 with blood 280, but will move during initial centrifugation to effect cell separation and to open the connecting fluid path to separate the two chambers 256, 260. The gel 272 flows radially, outwardly and upwardly so that gel 272 does not fall into the bottom chamber 260. The result of the initial centrifugation is shown in FIG. 23. Due to the relative densities of the platelet-rich plasma 284, separation medium 272 and red blood cells 288, the centrifugation will position these three substances in the previously-mentioned order from inside of the primary chamber 256 to the outside of the primary chamber 256 as shown in FIG. 23. In the figures, and as used herein, PRP stands for platelet-rich plasma and RBC stands for red blood cells.

Subsequently, the initial centrifugation is stopped, the result of which is shown in FIG. 24. Upon terminating centrifugation, the platelet-rich plasma 284 drains through the vents 268 by gravity into the lower chamber 260, where it is mixed with the clot activator 244 and secondary active agents 248 if present. The separation medium 272, however, will stay in place, thereby preventing the red blood cells 288 from entering the second chamber 260 through the vents 268. The vents 268 may be funnel shaped to ensure that the g force exerted makes all the platelet-rich plasma 284 flow into the secondary, densification chamber 260.

As shown in FIG. 25, centrifugation is restarted at the proper g force, e.g., 500-15,000×g, and a large membrane 292 is formed on the outer circumference of the lower chamber 260. Preferably, centrifugation takes place at about 2500 to 10,000×g for about 20 minutes to an hour depending on the density of the membrane sought to be achieved. This applies to all of the embodiments used for membrane formation set forth herein. It should be noted that the separation medium 272 and red blood cells 288 tend to stay in the same position during secondary centrifugation. This system allows for concurrent centrifugation and coagulation, which results in the large platelet/fibrin membrane 292. The device 252 also has a bottom 294, which may be removable, thereby allowing for the membrane to be easily extracted from the device.

The following systems and devices are variations of the basic system shown in FIGS. 21-25. For example, the cell separation or primary chamber 256 may have a different radius than the densification or secondary chamber 260. As shown in more detail in FIG. 26, the radii of the upper and lower chambers may be different, which allows for different g forces to be exerted at the circumference wall. Consequently, one speed rpm yields two different g forces, thereby simplifying motor and programming. More particularly, providing the chambers with different radii eliminates the need for multiple speed programming due to the different g force at the same rpm.

FIGS. 27-30 show a variation of the system set forth in FIGS. 21-25, in which concentric cylinders are used. The system 296 includes a primary tube 300 having an upper portion 304 separated from a lower portion 308 by a diaphragm or other separator 309. The primary tube 300 acts as the cell-separation chamber. At least one vent, hole or aperture 312 provides fluid communication between the upper 304 and lower portions 308 of the primary tube 300. Again, blood may be introduced into the primary tube 300 through one or more pierceable stoppers 316 or other suitable device discussed above. The primary tube 300 may contain an anticoagulant 232 to prevent premature clotting of the blood. A separation medium 272 prevents the blood from flowing from the upper portion 304 of the primary tube 300 into the lower portion 308 through at least one vent 312. The lower portion 308 may also have voids, holes or apertures 310, through which a liquid may flow. Densification of the platelet-rich plasma 284 takes place in a secondary, concentric tube 320. The secondary tube 320 may contain one or more of the coagulation activators 244 discussed above and/or one or more secondary active agents.

Initially, centrifugation of the system separates the blood into plasma and red blood cells, which are separated by the separating medium as discussed above and shown in FIG. 28. Initial centrifugation generally takes place at greater than about 1000×g for greater than about 10 minutes. Once the centrifugation is stopped, as shown in FIG. 29, the platelet-rich plasma 284 will fall into the lower portion 308 of the primary tube 300 through the one or more vents 312, and the red blood cells 288 will be trapped in the upper portion 304 of the primary tube 300 by the separation medium 272. At least one void 310 is provided in the wall of the lower portion 308 of the primary tube 300. The system is subsequently centrifuged as shown in FIG. 30, thereby resulting in at least a portion of the platelet-rich plasma 284 leaving the lower portion 308 through voids 310 of the primary tube 300 and entering into the secondary tube 320. Again, the red blood cells 288 will remain trapped by the separation medium 272 in the upper portion 304 of the primary tube 300. As shown in FIGS. 27-30, the secondary tube contains at least one clot activator 244, into which the platelet-rich plasma 284 will come into contact. Consequently, this variation also provides for concurrent coagulation and centrifugation, which forms the membrane 292. This variation allows for a more compact unit and reduces plastic usage. The device 296 may also have a removable bottom 324 to facilitate removal of the membrane.

As another alternative, a hydrophobic membrane 325 may be employed instead of a separating medium. The hydrophobic membrane 325 may be used in place of any of the systems using a separating medium. The hydrophobic membrane 325 only permits the flow of the platelet-rich plasma at a set g force, eliminating the need for a separating medium. In other words, instead of using a diaphragm having holes blocked by gel, a hydrophobic membrane may be used as shown in FIGS. 31-32. When using a membrane, the lower chamber and the upper chamber may have the same radii as shown in FIG. 21, or the two chambers may have different radii, one example of which is shown in FIG. 26. In addition, the hydrophobic membrane may be applied to the concentric design shown in FIG. 27.

The hydrophobic membrane 325 substantially prevents an aqueous liquid, such as platelet-rich plasma, from flowing through its pores until a set hydrostatic pressure is reached. Examples of hydrophobic membranes 325 may include, but should not be limited to, polypropylene, polycarbonate, cellulose, polyethylene, TEFLON® of Dupont and combinations thereof. Other examples include Millipore® membranes and screens manufactured by Millipore, or Nucleopore® membranes and screens manufactured by Nucleopore. Alternatively, a plastic diaphragm having precision holes drilled therein with a laser could also be used. When using a hydrophobic membrane, blood may be introduced into the cell-separation chamber, but will not fall into the densification chamber. The proper hydrostatic pressure may be achieved by first separating the red blood cells from the plasma at a low rpm. Subsequently, the rate of centrifugation is increased to achieve the desired pressure to overcome the surface energy/surface tension constraints that define the flow pressure. In other words, the gravitational force will increase with the rate of centrifugation, which will result in the platelet-rich plasma flowing through the membrane, but not the red blood cells. The membrane will substantially block the red blood cells.

Another modification to the above systems includes changing the configuration of the secondary or densification chamber of any of the embodiments discussed herein. These modified densification chambers may be used in systems, wherein the primary and secondary chambers have the same or different radii, wherein the chambers are concentric, and/or wherein a separating medium or hydrophobic membrane is used. The densification chambers may have a different interior walls which facilitate the removal of the membrane, and ensure the greatest recovery of the membrane. For instance, the densification chamber may contain a woven biodegradable fabric (such as Goretex® manufactured by Goretex) that improves the tear strength of the membrane for initial placement in the body, and that will later dissolve. The outer wall of the chamber may also contain molded bumps or grooves that support the fabric away from the wall at a uniform length to achieve a fibrin and platelet thickness of desired dimension on both sides of the fabric.

More particularly, as shown in FIG. 39, the interior or side wall of the densification chamber 318 may include one or more solid or serrated ribs 319 to allow removal of the membrane in the form of flat sheets rather than as a cylinder. The perforated ribs facilitate aeration of the membrane. The interior wall of the chamber may be configured to provide perforations in the resulting membrane to facilitate tearing. FIG. 39 shows a bottom plan view of one or more solid ribs of the interior wall.

FIG. 33 illustrates a woven-biocompatible fabric 328 that may be found on the interior of a densification chamber 326. Such a weave keeps the membrane 292 away from the wall itself. The fabric 328 facilitates separating the membranes from the cylinder to get a flat membrane and increases the tear strength of the membrane for certain applications. The fabric 328 becomes embedded in the membrane 292. Moreover, bumps 332 or grooves 340 may be molded in the wall 336 of the chamber 326 to control the thickness of the fibrin layer on either side of the fabric as shown in FIG. 34 and FIG. 35, respectively. These act as small-supporting ribs that keep the fabric spaced away from the wall. In summary, FIG. 33 shows the fabric 328 itself keeping the membrane from sticking to the wall 336; FIG. 34 shows bumps 332 in the wall 336 that facilitate removal of the membrane 324; and FIG. 35 shows grooves or molded support ribs 340 that keep the membrane 292 away from the wall. Walls having bumps 332 or grooves 340 may also be employed independently of the fabric 328.

Alternatively, as shown in FIG. 36, the densification chamber may be lined with a removable film 344 to facilitate membrane 292 removal. The film 344 may comprise plastics such as polyolefins which include polyethylenes, polypropylenes, polycarbontes or TEFLON®. The film 344 may have tabs 348 for easy manipulation, and may be colored to help separate the membrane 292 from the film 348. In addition, the film 348 may be treated to obtain desirable properties, such as glass-like contact activation. By maneuvering the tabs 348, the entire film 344 having the membrane 292 thereon may be removed. For example, the densification chamber 326 may be lined with a treated film that provides both platelet activation for coagulation and growth factor release and easy manipulation of the membrane. Alternatively, the PRP or PPP may be flowed through a high surface energy tubule to activate the PRP or PPP for clotting, enabling a rapidly clotting adhesive to be used as a fibrin sealing or adhesive layer.

Regarding other surfaces in the chambers, plastic surfaces may work, but may not be ideal for clot activation and release of platelet growth factors. As a result, alternatives to plastics are outlined in FIGS. 50 and 51. For example, the platelet-rich plasma may contact glass in the lower chamber. In other words, glass could be affixed to the bottom cap as shown in FIG. 50, or glass spheres may be glued or hot staked to the bottom as shown in FIG. 51. Glass could also be heated and dropped onto the plastic. Alternatively, the surface may be plasma treated using glow discharge processes employing activating gases such as oxygen or nitrous oxide. More particularly, the surface could be treated using plasma enhanced chemical vapor deposition. Alternatively, the surface may be modified using a variety of chemical coatings, e.g., silicon surfactants or PVPyr. Another manner by which to modify plastic is to put small sized silica beads or particles in the citrate solution in the upper chamber. Due to the high density of silica relative to the gel and red blood cells, most of the silica will remain in the upper chamber either below the gel or embedded in it. Accordingly, these plastic modifications may be used to coat portions of the systems, and more particularly, portions of the densification chambers of any of the embodiments set forth herein.

In a different aspect, the invention provides for the production of square-shaped platelet-rich fibrin membranes to be used in conjunction with wound care, which exploits the mitogenic characteristics of platelet and provides platelet-derived growth factors (PDGF) and beta-thromboglobulin (BTG), and protective action of a solid-fibrin film. Growth factors, BTG, platelet factor 4 (PT4) and thrombospondin are all factors that may enhance cell proliferation on the solid-fibrin web. More particularly, protective action includes microaerophilic environment, anti-septic activity, and separation activity. The device, which can be used to carry out concurrent centrifugation and coagulation, comprises a rotor medical device shown in FIG. 38. The device comprises a disposable cartridge 352, which may be made of plastic or some other suitable material. Again, the plastic modification techniques discussed above apply to any of the embodiments set forth herein. The cylindrical cartridge has two concentric chambers, namely, an inner chamber 356 and an outer chamber 360.

The inner chamber 356 is cylindrical and defined by an inner filtering wall 364 as shown in FIGS. 38 and 39. Any of the filters or filtering devices discussed herein are suitable for use with this embodiment. The inner chamber 356 has a top end 368 and a bottom end 372, each of which has a rotor shaft 376 attached thereto. The rotor shaft 376 allows the cartridge 352 to be inserted and used in a centrifuge (not shown). At least one of these ends 368, 372 of the inner chamber 356 may have a port or suitable aperture 380 through which blood from a patient may be introduced or injected. As discussed above, in one embodiment the inner chamber 356 may be kept at a vacuum in order to facilitate standard venipuncture. The inner chamber 356 may contain an anticoagulant 232 to prevent blood entering therein from coagulating. The inner chamber 356 acts as the cell-separation chamber. The inner filtering wall 364 is a selectively centrifugable (mechanically supported) filter, which will accept a discrete amount of whole blood. The filtering activity of the filtering wall substantially prevents red and white blood cells from flowing therethrough. The filter does, however, allow plasma and platelets to flow through to the second chamber 360 when a predetermined centrifugal force, e.g., greater than 1000×g for a predetermined time, e.g., greater than 10 minutes is exerted.

The second chamber 360 is defined by an external wall 384, the internal filtering wall 364 as well as top and bottom walls. The second external chamber 384 may contain one or more coagulation activators 244 as well as one or more secondary active agents 248 discussed above. The second chamber 360 acts as the densification chamber. As shown in FIGS. 38-39, the internal and external chambers 356, 360 are concentric.

In operation, after blood has been introduced into the inner chamber 356, the device 352 is centrifuged. As discussed above, the centrifugation takes place at a predetermined force for a predetermined time such that the blood is separated into plasma and red blood cells. Again, the filtering wall 364 allows the platelet-rich plasma to pass therethrough, whereas the red blood cells clog the filter. Upon passing through the filter 364, the plasma contacts the coagulation activator 244 and/or secondary active agent 248, thereby resulting in concurrent coagulation and centrifugation, and the formation of the membrane. To enhance coagulation, it may be helpful to provide a mixing movement. The centrifugation taking place after the plasma has entered the second chamber usually occurs at about 1500 to 15,000×g for greater than 10 minutes in order to obtain a white resistant fibrin-platelet rich membrane. The membrane can be used in any of the tissue regeneration applications set forth herein, but may be particularly useful in conjunction with wound or burn care.

On the inner portion of the external chamber 360, one or more pins 388 may be present to enable the membrane to be drawn out vertically from the top of the device. All of the discussion pertaining to the surface of the densification chamber, applies here to the outer chamber 360 (e.g. using fabrics, bumps, grooves, etc.). In addition, the discussion pertaining to modification of plastic surfaces also applies here as well. The membrane may be extracted by crunching the device, or opening it in two parts. Typically, for sanitary reasons, the device is disposable. The device provides friendly operations and provides safe and sterile conditions.

Another aspect of the invention pertains to devices and methods, as well as modifications of the above devices and methods, which can be used to form molded, high-density fibrin and platelet networks by radial or axial centrifugation. This aspect also pertains to a method for metered liquid splitting into multiple aliquots for simultaneous molding of multiple networks. The clinical efficacy and ease-of-use of autologous fibrin and platelet networks are discussed above. There are several clinical applications for the regeneration of soft tissue (e.g., meniscus repair of the knee), in which it is desirable to form the network or membranes discussed above into a specific shape prior to implant. In the case of meniscus cartilage, the ideal shape would be a semi-circular wedge shape, similar to an orange section, which can be used to replace a severely damaged meniscus. The platelets present would provide needed vascularization for tissue regeneration and the fibrin would provide an absorbable cushion for load bearing.

Current practices for repairing soft tissue, such as cartilage, allow for only twenty percent of cases to be treated. Frequently in the remainder of the cases, the soft tissue is permanently removed and the patient suffers from compromised mobility. This syndrome is evident in professional athletes and is of great interest in sports medicine. Synthetic materials are available to form as a scaffold for new tissue to grow into, but have the disadvantages of causing adverse immune response and poor success due to lack of vascularization. A successful method would enable splitting the platelet-rich plasma into controlled volumes for simultaneously forming multiple forms and shapes used for a given procedure.

Figure 40A:
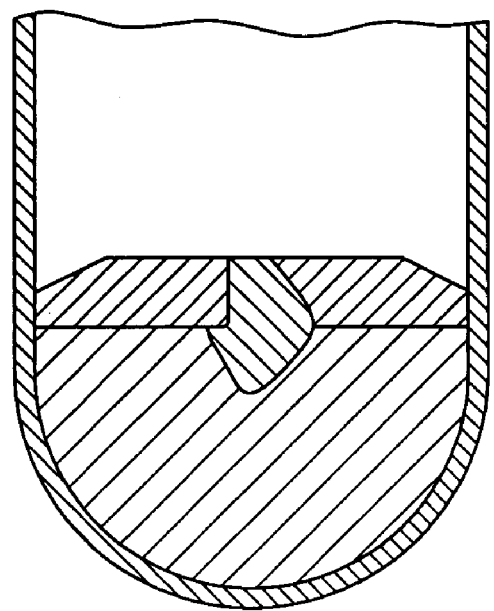
Figure 40B:
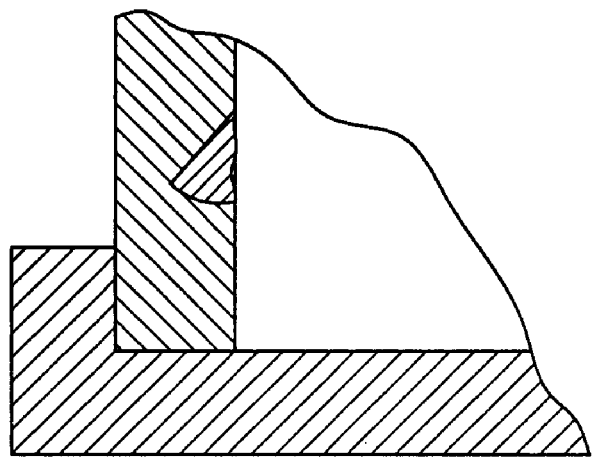

The mold system comprises a formed cavity defined by a shape of a desired part at the maximum point of centrifugal force in any of the centrifugation containers discussed above. The cavity may be formed at the bottom of a vessel when the centrifugation is performed in a radial centrifuge. Alternatively, the cavity may be defined in the cylindrical wall of vessel that is axially centrifuged. FIG. 40 shows examples of a mold oriented for use in a radial centrifugation as shown in FIG. 40(a) and a mold oriented for use in an axial centrifugation as shown in FIG. 40(b). The mold may be integral to the container or may be a separate part connected, coupled, extended or added to the vessel as shown in FIGS. 43-46. The cavity, if non-integral, may be of split design to allow molding of complex shapes and to provide for easy removal. The cavity may also contain a funneling feature to direct the flow of the fibrin/platelet mixture into the cavity as shown in FIG. 41. More particularly, FIG. 41 shows a mold 392 having a funnel 396 leading to a runner 400 which allows a substance to flow information to the cavity 404. The cross-sectional area of the funnel opening 396 will determine the relative amount of concentration of the fibrin/platelet monofilaments. A runner 400 may also be connected to the funnel 396 and cavity 404 as shown in FIG. 41, thereby allowing flow directly into the cavity 404 and minimizing any trimming of the molded part. As shown in FIG. 42, vent holes or passageways 408 may also be included into the mold frame 392 to allow the expression of gas and/or liquid out of the cavity 404 caused by the displacement of the entering fibrin. In other words, the vent holes 408 allow for the release of gases and liquids.

In procedures requiring multiple implants, particularly ones requiring different volume and density, one of the axial-centrifugation devices discussed above may be split into controlled volumes by inclusion of vertical vanes in the bottom as shown in FIGS. 43-47. In other words, one of the devices discussed above, e.g., a concentric chamber embodiment may be employed, but multiple cavities are used in each centrifuge vessel to simultaneously provide multiple-shaped objects. The relative amounts of platelet-rich plasma to be sent to each mold in the axial-spin design can be obtained by including vertical vanes 412 as depicted in FIGS. 43-47. The vanes 412 may extend the height of the device although they need not, and project toward the central axis but do not touch, thereby allowing free flow of the platelet-rich plasma between the volumes defined by the vanes.

FIG. 44 is a top plan view showing vanes B1 and B2. Vanes B1 and B2 do not touch, and vent 416 allows fluid connection between chambers W1 and W2 when the fluid is first added and the centrifuge is at rest. The cross-sectional area of chambers W1 and W2 may be proportional to the volume of the fluid to be sent to each mold. The liquid level, initially at rest, is equal in all compartments, thus the relative volumes are proportional to the cross-sectional area defined by the positioning of the vanes. Accordingly, the positioning of the vanes will determine the volume in each compartment. Consequently, larger "pie pieces" can be employed for deeper molds.

Once centrifuged, the volume in each compartment travels radially to the target mold. FIG. 45 depicts a three-chamber device having unequal "pie pieces." FIG. 47 shows a three-chamber device with each mold 420 set at a different radius, thereby subjecting the contents of each mold 420 to g force proportional to the radius. The number of chambers will depend on the particular application. The formed materials will have different densities depending on the radius of the mold 420. FIG. 46 shows molds in three different positions, namely, integral, connected and extending from the device. The positioning of the mold affects the density of the resulting membrane. Since the relative volume of each aliquot and the location of the cavities are predetermined, molded counter-weights can be added to provide proper balance. An example of a useful application of this feature would be the molding of a membrane at high density and a paste at low density.

In operation, platelet-rich plasma is added to a vessel, such as those discussed above, or is prepared by adding whole blood to a pre-processing chamber and transferring the platelet-rich plasma to a second vessel containing a suitable clot activator. The vessel is quickly placed in the centrifuge and spun at the desired g-force required for the application. This provides for the concurrent centrifugation and coagulation. The fibrin strand and platelets rapidly sediment toward the cavity and fill it. The fibrin strands are then cross-linked to form a stable network. Upon removal from the centrifuge, the molded part may be removed and any excess trimmed. For more complex shapes, a split cavity mold may be employed. As discussed above and shown in FIG. 41, a funneling pre-processor may be employed in the design to minimize blood volume required and to increase efficiency. Runners and vent holes as shown in FIGS. 41-42 may also be included to ensure the complete filling of the cavity and to facilitate handling of complex shapes, much like the runner system that is employed in plastic model kits for hobbyists.

FIGS. 47-49 show cross-sectional views of the device during operation. FIG. 47 shows the device at rest; the platelet-rich plasma 284 and coagulation activator 244 mix flows between chambers until a level fluid surface is achieved and the fluid is properly proportioned between chambers. FIG. 48 shows the device as the centrifuge starts; the liquid is formed into a vortex shape by the axial rotation. During centrifugation, the vanes 412 now prevent communication between channels and thereby maintain the proper dispensing to each mold. The walls 428 may be tapered towards the mold to act as concentrating funnels. As the centrifuge speed and resulting g-force increase, the parabolic vortex increases until all fluid is transferred to the molds. FIG. 49 shows the device at full centrifugation, at which point the molds are filled.

This system may also be used for platelet-poor plasma (PPP) to form substances comprising fibrin. In other words, it may be used in applications that require no platelets. Platelet-poor plasma may be formed by centrifuging a first tube at a higher g force, e.g. greater than 5,000×g, instead of 1,000×g. Also, the design can be used for non-autologous formation of the desired fibrin or fibrin/platelet network in cases where suitability of donor and recipient is established.

Overall, the molds provide complete and autologous patient compatibility. As a result, the fibrin-platelet network can be formed to precise molded shapes and densities. A multiplicity of shapes can be formed simultaneously, such as the left and right meniscus for the knee. In addition, a molding hammer, anvil and stirrup for an inner ear may be found using these molds, as well as a rotator cuff for a shoulder. Furthermore, elbow cartilage, parts of etepicondyle, parts of fingers, tarsus and carpus cartilage may also be formed. The formed membrane or network is also absorbable, stable and has growth factors to improve healing. For multiple shape applications, density of the parts can vary by setting the mold radius.

Another aspect of the invention pertains to devices and methods for controlling the distribution of platelets in a fibrin/platelet network utilizing differential centrifugal sedimentation. The clinical efficacy and ease-of-use of autologous fibrin and platelet networks are discussed above. The fibrin provides wound stasis and a medium for cell growth and mobility. Platelets, while initially contributing to wound stasis, also contain a variety of anti-inflammatory, growth and vascularization agents. As such, in many therapeutic procedures it is beneficial to concentrate the location of the platelets in the fibrin continuum. For example, in the case of chronic wounds, a concentration of platelets on the side of a membrane that contacts the wound would increase adhesion of the membrane to the wound and increase vascularization of the subdermal layer. For meniscus repair, it may be beneficial to have the platelets concentrated in the outermost region of the formed meniscus, namely, the "red zone," to increase vascularization of this region. For bone cement, it may be preferable that the platelets are evenly distributed throughout the continuum. Consequently, this aspect of the invention provides a manner by which to preferentially locate platelets in a fibrin matrix using centrifugal force.

Platelets sediment as a function of g-force while the formation of fibrin proceeds at a rate independent of g-force. More particularly, platelets sediment at constant velocity, and as a result, the platelets deposit at a constant rate until all have sedimented. Platelets are uniformly distributed throughout the platelet-rich plasma. As the plasma is subjected to a gravitational force, the platelets sediment at a constant velocity, the velocity increasing with increasing gravitational force. The time to complete the sedimentation is proportional to the height of the platelet-rich plasma that the uppermost platelets must traverse. Thus, for a 100 mm high column of platelets, the completion time for sedimentation is approximately 5 minutes at 6000×g or 15 minutes at 2000×g.

Fibrin monomers, on the other hand, form at a rate independent of gravitational force. For normal patients, this process is complete in about thirty minutes. Thus, the methods set forth herein solve the problem of developing a centrifugal force profile that will accommodate the two different rates of sedimentation, thereby resulting in preferential location of the platelets within the network. Preferential location of the platelets optimizes the tissue regeneration to fit each particular application, providing faster healing and higher success rates for the procedure. The method to preferentially locate the platelets involves adjusting the g-force during the sedimentation process to account for the difference in sedimentation rates of the platelets and the formation and subsequent sedimentation of the fibrin.

In one example, the platelet-rich plasma may be exposed to the coagulation activator, and then immediately centrifuged at about 4000 to 6000×g. Accordingly, the platelets will rapidly sediment in about 5 to 10 minutes and will then be layered on top with the fibrin that forms over the subsequent 25-35 minutes. The resulting structure will have the platelets concentrated on the surface that was initially formed and will diminish in the layers formed later. This application is particularly advantageous for meniscus repair and chronic wounds.

In another example, the platelet-rich plasma may be exposed to the coagulation activator, and then immediately centrifuged at greater than 2000×g. The platelet sedimentation and the fibrin formation may proceed at equivalent rates. Accordingly, the resulting network has platelets uniformly distributed throughout the network. This application is particularly advantageous for bone cement and for soft tissue growth in periodentistry.

In yet another example, the platelet-rich plasma may be exposed to the coagulation activator and immediately centrifuged. The speed of centrifugation, however, is cycled between alternative rates of about 1-2 minutes at about 4000-6000×g, then about 5-10 minutes at 1000-2000×g. The iteration may be performed about 5-10, resulting in a sandwich structure that has 10-20 distinct layers of alternating high concentration and low concentration platelets. This application is particularly advantageous for articulate cartilage repair, which prevents bones from rubbing together.

Consequently, controlling the rate at which the platelet-rich plasma and coagulation activator are centrifuged, as well as duration of the centrifugation, results in preferential location of the platelets. Controlling the location of the platelets optimizes the tissue regeneration depending upon the particular application, thereby providing faster healing and higher success rates of the procedure.

FIG. 56 shows another embodiment of the mold design. The molded insert 424 is generally made of a plastic or rubber material. The insert is introduced into and removable from a container 426 as shown in FIG. 56. Once platelet-rich plasma is situated in a container 426, a coagulation activator may be added thereto. Alternatively, a coagulation activator may be already be present in the plasma upon introduction. The insert has vanes 428 similar to those in FIGS. 42-49. The vanes 428 protrude in order to define chambers 430 in which a membrane may be molded or formed upon centrifugation. In other words, the vanes leave a space between a core 432 of the insert and the container when inserted, in which a cylindrical membrane may be formed using a radial centrifuge. Although the insert is shown with three vanes, the insert may be fabricated having one or more vanes. Alternatively, the insert could be split so that a rectangular membrane is formed between the two inserts. The advantage to using the molded insert 424 is that a flat bottom vessel with a swing head centrifuge is not required.

In another embodiment of the invention, methods and devices used to treat people suffering from cartilage diseases are provided. Fibrous cartilage tissue has a complex structure made in multi-layer organization of chondrocytes encapsulated in an amorphous fibrous tissue, the main component of which is collagen, plus ialuronic acid, and polysaccharides. The inner layer is the most compact one (i.e. it may be up to 25 times stiffer than outer layers), while the other two softer layers are recognized towards the surface. Pathological cases involving the articular cartilage tissue are common in humans and in animals, due to infections, auto-immune diseases (like arthritis), age-related degeneration and traumatic events. Today's cares are focused on pharmacological treatment of patients to stop infections, to reduce inflammation, or to stimulate the natural regeneration of autologous cartilage tissue. In painful cases, like treatment of knee meniscus breakage, surgical treatment is performed to eliminate the cartilage that is not replaced, leaving the patient's bone without protection. This embodiment provides methods to treat cartilage diseases.

The membranes and fibrin may be used as scaffolds to culture chondrocytes. More particularly, these methods could be applied to humans and to animal cells to produce biological active hard solid fibrin cushions, with autologous chondrocytes included, to replace damaged cartilages in vivo to support the mechanical stress and to start the biological recovery of the tissue. In one particular embodiment, starting from a biopsy of cartilage tissue that is digested enzymatically, as known by the ones skilled in the art, the chondrocytes are cultivated in monolayers with conventional protocol in a $CO_2$ incubator. The chondrocytes, once carefully detached from their supports, can be mixed with the PRP just before spinning the container at about 4,000 to 10,000×g in order to obtain "orientated" strong membrane that can be used to replace part of damaged cartilage in vivo. The centrifugal force applied may differentiate the chondrocytes in different kind of cartilage.

The fibrin scaffolds having the chondrocytes can be cultured for several days in a special bioreactor under sterile conditions (as described by R. Portner, Animal Cell Culture Group—Dortmund University). In this device the DMEM (Invitrogen) culture media, added with serum, TGF (Transforming Growth Factor—Cell Concept) IGF (Insulin like Growth Factor—Cell Concept) is continuously refreshed on to the scaffold in a flow chamber. This procedure may be conducted for 19 days. The scope is to produce real cartilage in vitro on the base and shape of the original fibrin. This new cartilage may be used to replace damaged cartilages in vitro.

In one method, a very strong autologous membrane may be formed using concurrent coagulation and centrifugation methods discussed above. More particularly, a thick membrane (e.g. a 3-mm thick and 24-mm in diameter) may be prepared according to Example 5 below. Of course, a wide variety of sizes of membranes may be made using any of the devices or methods discussed above. One particular membrane may be made in a sterile container (e.g., a flat bottom 25 ml glass flask filled with about 20 ml of autologous platelet-rich plasma (PRP) and spun at about 4500-5000×g for 30 minutes). In this step platelet poor plasma (PPP) could be used. Any of the other membrane formation techniques set forth above may also be employed.

After this, or any other membrane of the invention, has been formed, it may be thoroughly washed with sterile physiological solution and placed in a larger sterile flask containing the activator, to prepare a second layer of platelet-rich fibrin (PRF). In this step, a new amount of platelet-rich plasma is introduced, in complete sterility, in the new flask containing the strong membrane. A second flask may be submitted to a second centrifugation step in order to obtain a triple layer membrane. In one particular example, this centrifugation may take place at a rate of 1000×g for 20 minutes to form a 30 mm in diameter. Centrifugation may take place at any of the rates set forth above (namely, 500 to 15,000×g for greater than 10 minutes.) The resulting membrane could be used to implant where the cartilage is to be replaced. Again, the thickness and dimensions of the membrane are dictated by the conditions set forth above. The amount of blood and the type of flask will also change accordingly. The key is to expose a sterile membrane (formed by any of the processes set forth above) to additional coagulation activator, and subsequently centrifuge the contents in order to form a second layer of platelet-rich fibrin. Alternatively, an additional coagulation and centrifugation could form a third layer of membrane, and so on.

In a related method, cartilage tissue (autologous) is put in culture IN VITRO in a gel, according to the Alginate Recovered Chondrocyte (ARC) method, which is well-known to those having skill in the art. The gel in the ARC method could be replaced by autologous fibrin prepared according to the methods and devices set forth above. More specifically, during the second step of the preparation of platelet-rich fibrin, the selected chondrocytes strains can be added to the secondary container together with autologous fibrin and the mix could be brought to jellify at a low centrifugation rate, or with no centrifugal force applied at all.

The form and dimensions of the container in which the jellification takes place may be chosen according to the subsequent use of the "artificial cartilage" (i.e., the form of the cartilage to be replaced). The jellification may be performed in such a way that the gel is formed around the strong membrane prepared according to the preceding paragraph. This may be achieved by placing the strong membrane inside the container where the second clotting is taking place, in such a way that new gel will substantially surround the original strong membrane and the chondrocytes will be included in the gel. The sterile container having autologous chondrocytes, jellified autologous platelet-rich fibrin, and eventually the inner strong membrane, may be put to incubate in an appropriate atmosphere (temperature, O2, CO2 and R.H. levels), as it is known to people having skill in growing chondrocytes in vitro. This may give the new tissue grown in vitro on a fibrin gel scaffold. Once the tissue culture has the correct density of chondrocytes and fibrous tissue, a triple layered tissue will result in a membrane that is very strong inside and soft and ready to replace the sick tissue in the host. Appropriate additives will be added to the culture media in order to optimize the yield of the procedure. The use of stem cells can also be previewed, since these are the origin of all cells in the body, they can originate new chondrocytes in vitro, if properly treated as is known to skilled people.

Overall, this embodiment produces an implant to treat the above-described illnesses, while reducing the risks connected with use of synthetic or heterologous materials. The autologous chondrocytes will find in the membrane, enriched with platelet, the proper solid scaffold for proliferation in vitro and in vivo and to produce the chondrocyte matrix that is fundamental for the production of new cartilage. The resulting membrane is easy to prepare in a sterile cabinet and has the physical properties that allow it to be implanted directly in place in order to reduce the recovery time after surgery, and to facilitate the migration of chondrocytes that will build up new cartilage.

The embodiments and methods described herein may also be used in conjunction with collection of PRP from a plasmaphoresis machine. Many times during surgery a cell saver or phoresis machine is used to conserve blood by suctioning the pooled blood in a surgical site, separating the cells and reinfusing the cells into the patient. This technique, sometimes called "bloodless surgery," minimizes or eliminates the need for blood transfusions to replace lost blood, making the procedure safer and less expensive. Such equipment is made by Haemonetics (Braintree, Mass.) and Cobe (Colo.). These phoresis machines sometimes are used to separate platelets and plasma from the red cells. Access to the platelet and plasma port of these machines allows collection of PRP. If the PRP is added to the second tube, it is recalcified and can be simultaneously centrifuged and coagulated, in conjunction with the methods set forth above. This enables larger volumes of PRP to be obtained, while eliminating the first centrifugation step and collection device. A wide variety of solid-fibrin webs and membranes may be obtained therefrom, and used in the application herein.

The majority of centrifuges are designed to process a blood collection or second fibrin/platelet network tube having dimensions of about 16 mm×125 mm. Tubes of these dimensions tend to hold a maximum capacity of 15 mls. These tubes are nested in a centrifuge cup that is removable for cleaning purposes. The cups are tube-shaped and may have a collar to support the tube and cup during high-speed centrifugation (FIG. 52). Metal forming or injection molding of polymeric materials can integrally form the collar onto the tube. It can also be separately formed and adhered to the tube by adhesive, ultrasonic welding, spin welding, induction welding or other methods of material adhesion; these methods do not require the collar and tube materials to be the same, allowing greater choices of material selection. Alternatively, the tube may have a tapered outer diameter that narrows towards the lower, closed end and the collar may have a mating inverse taper in its inner diameter, such that the tube, when inserted into the collar, can only proceed to the point where the tube outer diameter and the collar inner diameter interfere, the distance from the tube's open end being preset during the forming operation. The collar should have an inner diameter that allows sufficient contact with the tube to support the tube during the high shear forces developed at centrifugation. The thickness of the collar, i.e. the height of the squat cylinder, is determined by the material properties of the collar and the forces the collar will be subjected to during centrifugation. The outer diameter of the collar should be sufficient to preclude the tube movement radially outward during centrifugation. The dimensions of the collar may be easily calculated using engineering computation or computerized finite element analysis.

The materials of construction are typically steel or engineering plastics of high strength. In many applications of fibrin and platelet networks, such as spinal fusion and plastic surgery, larger volumes of PRP and/or fibrin platelet networks than those obtainable with 16×125 mm tubes are desired. A method for obtaining significantly larger volumes of blood collected or fibrin/platelet comprises making the collecting or receiving tube larger by affixing a support collar thereto or integrally forming the collar thereon. The tube can be placed directly into the centrifuge rotor after removing the supporting cup. The material of construction of the tube may hold vacuum, accept a stopper, be compatible with blood and have sufficient strength to withstand centrifugation. Examples of suitable materials include, but are not limited to, metal, glass with a support collar attached by an adhesive, or a high strength barrier plastic such as polyethylene terapthalate (PET) or polyethylene napthalate (PEN). Such a tube may have a diameter of about 20 to 30 mm (e.g. 25 mm) and a length of 110 to 140 mm (e.g. 125 mm) and hold more than 20-30 mls. Larger tubes can be made by modifying the rotor to accept larger diameter tubes. This is also useful in diagnostic testing and other procedures in which larger specimen volumes than those obtainable with standard size tubes are desirable.

Delaying centrifugation and/or recalcification after PRP transfer may improve incorporation of fibrin, platelets and growth factors into graft materials. Delaying centrifugation and/or recalcification does not mean that the concurrent coagulation and centrifugation does not take place. Small particle size graft materials may be added to the PRP subsequent to transfer to the second tube or may at least be one of pre-filled into the secondary tube during the manufacturing process. These graft materials may comprise autologous bone, donor bone, animal bone, synthetic bone, tri-calcium phosphate, carbonate, sulphate and combinations thereof. Due to the density of the graft material and its small particle size, it may be difficult to incorporate the graft uniformly into the fibrin-platelet network or solid-fibrin web. This may be the result of graft's density being much higher than the PRP's density, and the graft material rapidly packing into the bottom of the tube during centrifugation. The small particle size of the packed graft material may not always allow the fibrin and platelets, which descend later during the centrifugation cycle, to easily penetrate the packed graft material's interstices. An alternative method to immediate centrifugation is to delay the centrifugation for a period of time, allowing fibrin monomers, platelets and growth factors to surround and penetrate the porous surface of the graft material, before subsequent cross linking takes place. The mixture may be mixed periodically or continuously during the delay period to improve the dispersion and coating of the individual graft particles. After an appropriate time determined by the particle size of the graft material, centrifugation may be initiated to pack the graft and stabilize the fibrin-platelet network by compressing the network by centrifugation during the crosslinking step of fibrin formation.

There may be a wide range of delays, depending on the particle size of the bone graft material: the larger the particle, the less the benefit of a delay. For autograft and human and animal grafts greater that 3 mm, no delay may be required to incorporate the graft into the fibrin-platelet network. For grafts greater than 0.5 mm and less than 3 mm, a 1 to 20 minute (e.g. 3 minute delay) allows good incorporation of the graft material while still allowing centrifugation during the cross-link process. For graft materials less than 0.5 mm, a 3 to 25 minute delay (e.g. 5 minutes delay) allows good incorporation and compression during cross-linking. Again, delaying the recalcification of the PRP allows the PRP to be absorbed into the graft prior to beginning the coagulation. In one example, the calcium is not pre-filled into the second tube but is added after a soaking period, 1-30 minutes, ideally 5-15 minutes.

In other instances, large volume graft materials are employed, such as bone rods for spinal fusion. In these instances, it is sometimes desirable to soak the graft material in the PRP prior to coagulation to effect deeper penetration of the plasma, platelets and/or growth factors in the porous surface and thereby improve the incorporation of the subsequent fibrin-platelet network into the graft material. This may be achieved by delaying the addition of the calcium or other cationic species that would displace the endogenous calcium bound by the chelating agent anticoagulant to the PRP after the transfer to the second tube. The calcium-coagulation activator may be added directly to the tube after the appropriate time delay dictated by the properties of the graft material and subsequently centrifugation during coagulation. Alternatively, the calcium-coagulation activator may be added by using a reservoir containing the calcium solution that is connected to the second tube and is activated by increasing the centrifugation speed, in a method similar to that of the single tube system embodiment.

It may also be desirable to spray PRP onto the surface of a wound and form the fibrin-platelet network in-situ. This procedure provides enhanced therapeutic value. The fibrin can act as an adhesive while the platelets provide improved healing by addition of their growth factors. Examples of procedures that employ this technique may include: adhering skin grafts to burn victims or chronic wounds; adhering skin to sub-dermal layers during plastic surgery such as face lifts; sealing oozing wounds following debridement of burn victims; and applying a topical haemostatic agent. One method of achieving the desired effect is to transfer the PRP to the recalcifying or secondary tube and then add a pump aerosol sprayer or air assisted sprayer to the tube and apply the recalcified PRP to the wound site. The PRP will then form a fibrin-platelet network in situ.

An alternative method would be to pump directly out of the first tube following red cell separation or to transfer the PRP into a tube that does not contain calcium-coagulation activator or other cationic species. The calcium may be added by addition of the solution to the fluid path during pumping by utilizing a separate fluid manifold or by flowing the PRP through a chamber that contains calcium crystals.

An alternative method may be to concentrate the platelets into the bottom of the second tube without calcium solution by centrifuging the PRP subsequent to transfer. The intake for the pumping system would draw from the bottom of the tube, applying platelets at higher concentrations for increased levels of growth factors. The intake stem can have a sliding diaphragm that seals the platelet concentrate below the diaphragm. The intake stem can have a stop that limits the initial position of the diaphragm, thereby setting the platelet concentration in the volume to be dispensed to a desired value (See FIG. 53). The stop is located a preset distance from the bottom of the intake that will yield the desired concentration of platelets in the volume of plasma below the diaphragm. The higher the stop is located on the intake stem, the lower the platelet concentration will be. Another embodiment is to place a high-energy clot-activating surface in the fluid path of the spray system. The surface will activate the plasma and form a clot with higher cross-link density, providing greater mechanical strength and reduced clotting time.

Other devices may be employed to facilitate the removal of the fibrin-platelet network, with and without graft material, from the secondary tube. After completion of the second centrifugation step, the fibrin-platelet network may be packed into the bottom of the second tube. Normally, the tube may be decanted into a sterile cup and the network is free to flow into the cup. At higher centrifuge speed required for more dense networks, the clot may be packed to tight for easy decanting. The packing may form a hermetic seal against the wall of the tube such that a vacuum is formed as the clot moves upon inversion, preventing further flow. This situation may be exacerbated by the addition of graft materials that are compacted during centrifugation, forming a dense packed matrix, much like the sintering of metal powders. It is therefore desirable to remove the network from the bottom of the tube, preferably as part of a delivery system, for addition of the network into a wound site, such as a bone cavity.

One method of facilitating the removal of the network is the inclusion of a cup with a perforated bottom into the second tube at the time of manufacture (See FIG. 54). The bottom is perforated (FIG. 54a) to allow the serum produced during centrifugation to drain during removal of the cup from the tube. The walls of the cup may vary in height ranging from shallow aspects (FIG. 54a) to the entire length of the tube (FIG. 54b). The lip of the cup may contain a method of linking to a delivery device. The method of linking may be threads, bayonet twist locks, clips or similar mechanisms. The walls of the cup may have grooves on its outer walls to prevent a vacuum during removal so that excessive removal force is avoided (FIG. 54d). The wall of the cup may have perforations so that the serum above the clot can flow through the walls, along the grooves and into the volume under the cup created during removal of the cup from the tube. The top of the cup may also link to a dispensing system operated by positive displacement of a piston through the cylindrical section of the cup; the operation may mimic a syringe (FIG. 54e) or ratcheting "caulk gun" mechanism (54f). The material of the cylindrical portion of the cup or dispensing cylinder may be radio-opaque to allow accurate dispensing using fluorometric technique. In FIG. 55, the second tube is cylindrical and has a stopper in either end of the cylinder. After centrifugation, the stoppers are removed and a piston displaces the formed network. This constitutes a cartridge system. Alternatively, the cup may be attached to the stopper by fibers such that the cup is extracted as the stopper is removed.

The membranes and fibrins produced by the methods disclosed herein may act as a scaffold to be used to culture cells, as discussed above. The fibrin matrix may be dense enough to act as a scaffold. The matrix may be formed in a slowly absorbed scaffold material such as a collagen sponge, a biodegradable polymer or a non-biodegradable polymer such as a abdominal aortic aneurysm graft. These combined scaffolding may provide additional mechanical strength and more uniform tissue regrowth than current scaffolding materials. In one example, the membrane obtained by the application of high centrifugal force, e.g. from about 4,000 to 10,000×g, may act as a scaffolding for adhesive cultures in vitro of dermal cells. These cultures are particularly useful to repair severe damages of the skin due to burns or to mechanical abrasion of the original tissue. These fibrin scaffolds naturally provide the cells in culture with growth factors, by the platelets, and with adhesive factors, by the solid-fibrin web. In order to obtain a good culture in vitro it may be advisable to start with the good density of epithelial cells in the culture media.

The membranes and solid-fibrin webs described herein may also be used to fuse stem cells thereon. More particularly, membranes and solid-fibrin webs may be used to cultivate pancreatic cells together with stem cells in a monolayer or in several layers of cells or membranes. For example, Medvinsky at the University of Edinburg, UK and X Wang at the University of Portland, Oreg., recently demonstrated that stem cells injected in the pancreas of diabetics mice fuse their genoma with ill pancreatic cells and generate several degrees of polyploids that are again active in producing insulin. Active growth factors present in the scaffolds and supports discussed herein may enable the growth of cells using conventional media, and the possibility of studying the fusion and the biochemical aspects and the cytological aspects.

In a different application the chondrocytes taken from a monolayer culture are immobilized in alginate beads, as known by the ones skilled in the art. These solid beads are compressed to a larger "tissue like" aggregate using the centrifugal force to "compress" these aggregates in order to regulate the pneumatic pressure and to stimulate the "tissue" according to the physiological stress in vivo. (Czermak P.—University of Applied Sciences, Giessen, Germany). During the centrifugation, PRP can be added to the alginate beads to prepare a compact bioactive aggregate ready to be implanted in place of a damaged cartilage, or to be cultivated in a bioreactor for several days in order to guide the cartilage growth.

EXAMPLES

Example 1

In a 5 ml glass container for antibiotics, being sealable under vacuum, made of transparent white glass, inert and 1 mm thick were introduced 100 mg of tranexamic acid, acting as fibrin stabilizer. The synthetic tranexamic acid, being more than 98% pure, is put on the market by the American Company Sigma Inc. Separately, a 1M $CaCl_2$ solution was prepared, by weighing on a precision balance 147.0 g of $CaCl_2.2H_2O$ (>99% pure), from the same American company Sigma Inc.

This salt was dissolved in exactly 1 liter of ultrapure non-pyrogenic distilled water, for a few minutes at room temperature, under frequent stirring. By using a precision piston dispenser, having a dispensing precision of ±5% (Eppendorf like), 80 μL of the activator solution were introduced in the glass container. In this step, at the same time as the dispensing, a filtering was carried out by using a 0.22 μm Millpore sterilizing filter, while carefully preventing possible contamination from powders or filaments of any kind. Finally the glass container was plugged with a rubber cap being pierceable and pluggable under vacuum, while minding not to completely plug the container, so as to allow the subsequent vacuum plugging and possibly a further sterilization by using gas. The container was then introduced into a suitable device for vacuum plugging, while preventing any possible contamination from solid particles in the atmosphere (ULPA or HEPA filtration in sterile chamber). A vacuum as high as 4 ml was applied, by using a membrane vacuum pump and a micrometric control, to the inner atmosphere of the device. In order to control the vacuum level in the inner atmosphere, a precision vacuum gauge was used (precision #1 mbar). Finally, without discharging the device, the container was plugged under vacuum, to be thereafter recovered for the use as described in the following Example.

Example 2

10 ml of venous blood were drawn from a patient according to the provisions of the qualitative standards for clinical analysis, e.g. by using VACUTAINER® sterile test-tubes by Becton-Dickinson, added with a 0.106 M sodium citrate solution. For this purpose also test-tubes added with disodium or dipotassium ethylenediaminetetraacetate can be used. The sample was carefully kept sterile during the blood drawing. Finally, the sample was gently shaken for wholly mixing the components, thereby ensuring the anticoagulating action of sodium citrate. The test-tube was then introduced in a suitable centrifuge, while carefully balancing the rotor weight in order to prevent the same centrifuge to be damaged. Once the lid is sealed, the sample was centrifuged at 3500 rpm for 15 minutes, thereby separating the red cells (being thicker) from the citrated plasma (supernatant). In this case the plasma yield, mainly depending upon the characteristics of the donor blood, was as high as 55%. The test-tube containing the separated plasma was kept plugged in sterile conditions and was placed vertically in a stand for recovering the plasma itself, in this step care was taken not to shake the test-tube, in order to prevent the mixing of the two phases separated in the centrifugation. The outer portion of the test-tube cap was then sterilized by using denatured alcohol and then a sterile needle, being connected to a sterile syringe, was introduced in the test-tube cap. The needle was brought up to 3-4 mm apart from the separating meniscus of the two phases, and 4 ml of plasma were drawn. By using the same needle, the cap of the container according to the present invention, which had been prepared as described in Example 1, was pierced, having been previously sterilized by using alcohol. As soon as the needle pierced the cap, the citrated plasma contained in the syringe was completely sucked into the container. This was gently shaken and, after about 2 minutes at 37° C., a clot of sterile autologous fibrin glue was obtained, ready to be immediately used.

Example 3

About 18 ml of venous blood were drawn from a 49 year-old patient by using 5 ml sodium citrate VACUTAINER® test-tubes by Becton-Dickinson, taking care to shake gently just after the drawing of the sample. The so taken blood was immediately subjected to centrifugation (15 min. at 2500 rpm) to separate the plasma. The plasma (12 ml) was carefully transferred into two 10 ml test-tubes, containing 120 μL of $CaCl_2$ (10 g/100 ml) each, which had been prepared as described in Example 1, but without using tranexamic acid. After mixing the plasma with the activator, the test-tubes were centrifuged for 30 min. at 3000 rpm, finally obtaining two massive fibrin samples which were inserted, with all sterility precautions, within 2-3 hours from preparation, in the large vesicular mandibular cavity resulting from extraction of impacted left canine and right second incisor, as well as from abscission of the cyst present in the central area of the incisor teeth. Finally the gingival edges were closed with eight stitches. A radiographic check 15 days after showed the fibrin still in its position, apparently intact. Histology 7 months after proved the complete replacement of the fibrin with bony tissue, with a better post-operative course than with traditional methods, requiring over 12 months to achieve the same result. Since no antifibrinolytic agent had been used for the preparation of autologous fibrin, it can be stated in this case that said additive was useful for the specific purpose.

Example 4

To produce an adhesive fibrin glue 12 ml of plasma, obtained as in Example 3, were transferred, with all the measures in order to preserve sterility, into a 20 ml container according to the present invention, prepared as described in Example 1.

After careful stirring, the mixed plasma was poured on a sterile glass slide, of the kind used in chemical laboratories, where the plasma was mixed with sterile and very pure calcium carbonate of coralline origin (BIOCORAL™•NOTEBS S.A. France), or with calcium fluoride (>98% Sigma Inc.). These calcium salts are both well known to the skilled in the art as stimulators of fibroblasts.

By mixing one part of the plasma with one part of calcium carbonate, (e.g.; 2 ml with 500 mg) a malleable, sterile and adhesive paste was obtained and used as a filler for subgingival spaces or different cavities after abscission of infected mucous sacs. The paste, positioned so as to fill the empty spaces, formed in a few minutes a solid fibrin web acting as a haemostatic plug and created an autologous biological substrate supporting the mucous edges in position and where later migration of connectival cells started.

Example 5

To obtain a membrane of fibrin glue 20 ml of plasma, obtained as in Example 3, were put in a 25 ml, flat-bottomed container according to the present invention prepared as in Example 1. After the usual careful stirring, the container was centrifuged for 40 min. at 4000 rpm with a swing-out rotor. At the end of the centrifuging operation, from the bottom of the test tube a white-colored, very compact and tensile-strong membrane was recovered, having the same size as the bottom of the test-tube (24 mm diam.) and thickness of 3 mm. This autologous membrane, owing to its compactness and strength, was used as a holding and separating membrane in dental and general surgery, as a substitute for porous synthetic membranes. The obtained membrane can be stored sterile for several days at 4° C.

Example 6

To obtain large-sized membranes of fibrin glue about 200 ml of citrated plasma were drawn from a patient, collected and separated in a double transfusion bag. The plasma was subjected to cryoprecipitation by freezing at −80° C. for 12 hours, defreezing being carried overnight at 4° C. (this procedure is well known to those skilled in the art). The same morning the plasma obtained by this procedure was subjected to centrifugation for 15 min. at 5000 rpm at 4° C. to obtain about 20 ml of cryoprecipitate. After careful removal of the supernatant by using a pressing device (e.g. XP100 of the company Jouan S.A. France) the cryoprecipitate was taken up with 20 ml of whole plasma of the same patient. The resulting 40 ml were put in a 35 mm diameter, flat-bottomed sterile polypropylene container according to the present invention, containing the suitable quantity of activator, as in Example 1. After careful shaking, the container was centrifuged for 40 min. at 5000 rpm to obtain a membrane as in Example 5, but more compact and tensile-strong owing to the higher content of fibrin. Said membrane too can be stored in sterile form for several days at 4° C.

The membrane obtained by the method described in Example 5, in addition to utilization described in Example 4, can be used as a substrate for the culture in vitro of dermal cells of the same patient, in order to obtain grafts to be transplanted in case of very serious scalds.

Membranes of a good quality useful for the above mentioned purposes can be obtained also from whole separated plasma directly transferred into the container according to the present invention. The obtained membrane will be thinner than the above described one, but still useful for surgical uses and as a substrate for cellular growth.

Example 7

To obtain spray fibrin starting from a cryoprecipitate as in Example 5, 20 ml of cryoprecipitate were taken up with 10 ml of whole plasma at room temperature and gently shaken, to complete dissolution. The resulting plasma was carefully transferred into a 50 ml container according to the present invention prepared as in Example 1, shaking gently for a perfect mixing of the components. After 120 sec. at room temperature, the test-tube was connected to a Venturi-type sterile air compressor, known to those skilled in the art, to be uniformly distributed on the surface of a bleeding organ being subjected to surgery (lung, heart, spleen, arterious anastomosis). The concentrated plasma, containing concentrated fibrinogen, thrombin, calcium ions and other coagulation enzymes, distributed over the organ, coagulated within a few seconds, owing also to tissue coagulation activating enzymes present in the endothelium of the patient creating a fibrin film having a protective haemostatic function. The surgical operation was therefore concluded with the reduction of internal hemorrhages and so avoiding further blood transfusions or complications.

Example 8

The membrane obtained by the method described in Example 5 will also incorporate autologous platelet if platelet-rich plasma (PRP) is used as a starter blood component. To obtain PRP from whole blood, blood samples may be centrifuged at 1000×g for 10-15 min. The following steps will be similar to the ones describe in the above-mentioned example.

The membrane obtained with this application method could be used as an active substrate to study in vitro the phenomenon of stem cells fusion described by Wang and Vassillopoulos (Nature-Vol 422-2003, 24$^{th}$ of Apr.). This study discloses the use of stem cells that grown in the presence of hepatocytes in mice liver, and fuse their genomes to create a brand new cell able to re-generate the damaged or defective tissue.

Due to the presence of platelets, providers of growth factor, and other stimulating agents, the membrane obtained as described above could be used as a support to study in vitro this very important phenomenon and eventually use the obtained generation of new cells to be introduced in vivo (like what has been done for the condrocytes or for the epithelial cells).

Example 9

All the following procedure is operated under a Laminar Flow Cabinet in sterile conditions. Starting from a solid bioptic sample the dermal tissue was treated with a homogenizer to separate little cell agglomerates keeping their single cell integrity intact. After washing the homogenate with 40 mM sterile PBS (Phosphate Buffer Solution pH 7.3—Gibco) the cells were centrifuged at 500-1000×g for 7-15 min. in a PP tube to recover the pellet. The wash was repeated twice. The cells obtained were then digested at 37° C. for 20 min. with a solution of tripsin 0.05%/EDTA 0.02% to eliminate the collagen structure that supports the cells.

Subsequently, the cells were well washed with sterile PBS to eliminate the collagenase. The cells were then re-suspended in a culture media (for example M199, HAM-F12, or another, known to the ones skilled in the art) and homogeneously distributed on the surface of a fibrin membrane. The density of the cells on the surface of the fibrin scaffold may be important for the good result of the culture of epithelial cells. For example, the best results can be obtained with a density of 1 to $3 \times 10^4$ cells/cm$^2$ of membrane, where they normally adhere in 15-60 min. after distribution, and after 2-5 hours they are completely flat. The culture may be kept up to 5 days in a controlled atmosphere of 5% CO$^2$, R.H. 98% at 37° C., regularly controlling the development of the culture, and eventually changing the culture media every 2 to 3 days, if necessary. In case of a cylindrical container a proper roller system is used on a 24 hour base, inside the CO$^2$ incubator, so that the cultured media continuously washes the membrane surface feeding the cells in culture.

The culture should be carried out in a proper sterile container, with a venting system that allows exchanges of gases, but keeps the sterility of the inside. The fibrin membrane should form on the inside of the container to perfectly adhere to the inner surface of the flask during all the culture time.

After verifying the development of the culture in vitro (for example using a contrast phase microscope), the membrane, with the cells on the upper surface, is carefully recovered and it is ready to implant under sterile conditions on the patient's wound or burn, eventually keeping it in place with stitches.

We claim:

1. A device for use in axial centrifugation, the device comprising:
   a container configured for axial centrifugation, the container including
      a primary chamber that can receive blood including an anticoagulant;
      a secondary chamber containing a coagulator; and
      a filter separating the primary chamber from the secondary chamber,
   the filter substantially preventing red and white blood cells, originating from blood drawn into the primary chamber, from entering the secondary chamber under a centrifugal force of about 1000×G or greater, but substantially permitting plasma and platelets originating from the blood to flow into the secondary chamber under a centrifugal force of about 1000×G or greater.

2. The device of claim 1, wherein the primary chamber contains an anti-coagulant.

3. The device of claim 1, wherein the coagulator comprises calcium.

4. The device of claim 3, wherein the coagulator comprises at least one calcium chloride, calcium fluoride, calcium carbonate, calcium gluconate, calcium fumarate, calcium pyruvate, an organic calcium salt and combinations thereof.

5. A device for use in axial centrifugation, the device comprising:
   a container configured for axial centrifugation, the container including
   (a) a primary chamber that can receive blood, wherein the primary chamber includes a separation medium comprising at least one of a silicone gel, a polyester gel, a thixotropic gel and a combination thereof,
   (b) a secondary chamber containing a coagulator,
   (c) a diaphragm that separates the primary chamber from the secondary chamber wherein the diaphragm has at least one vent that is plugged with the separation medium wherein said separation medium-plugged diaphragm prevents fluid communication between the primary and secondary chambers prior to centrifugation, wherein the separation medium moves into the primary chamber during centrifugation of about 1000×G or greater to provide fluid communication between the primary and secondary chambers through the diaphragm through the at least one vent, wherein the separation medium forms a barrier in the primary chamber that substantially prevents red and white blood cells, originating from the blood drawn into the primary chamber, from entering the secondary chamber during centrifugation and wherein the plasma and platelet enter the secondary chamber during centrifugation.

6. The device of claim 5, wherein the separation medium substantially prevents red and white blood cells, originating from blood drawn into the primary chamber, from entering the secondary chamber after centrifugation.

7. The device of claim 5, wherein the coagulator comprises at least one of calcium chloride, calcium fluoride, calcium carbonate, calcium gluconate, calcium fumarate, calcium pyruvate, an organic calcium salt and combinations thereof.

* * * * *